(12) United States Patent
Edmiston et al.

(10) Patent No.: US 12,208,007 B2
(45) Date of Patent: Jan. 28, 2025

(54) HELICAL CARDIAC ANCHORS FOR MINIMALLY INVASIVE HEART VALVE REPAIR

(71) Applicant: NeoChord, Inc., St. Louis Park, MN (US)

(72) Inventors: Daryl Edmiston, Draper, UT (US); Tyler Nordmann, Maple Grove, MN (US); Graham Garvin, Redwood City, CA (US); Dan Johnson, Minneapolis, MN (US); Max Bock-Aronson, Minneapolis, MN (US); Andy Freeman, St. Louis Park, MN (US); Ryan Um, St. Louis Park, MN (US); Randall Beyreis, Corcoran, MN (US); Brady Hatcher, Rogers, MN (US)

(73) Assignee: NeoChord, Inc., St. Louis Park, MN (US)

( * ) Notice: Subject to any disclaimer, the term of this patent is extended or adjusted under 35 U.S.C. 154(b) by 308 days.

(21) Appl. No.: 17/150,733

(22) Filed: Jan. 15, 2021

(65) Prior Publication Data

US 2021/0220138 A1 Jul. 22, 2021

Related U.S. Application Data

(60) Provisional application No. 62/987,140, filed on Mar. 9, 2020, provisional application No. 62/962,054, filed on Jan. 16, 2020.

(51) Int. Cl.
*A61F 2/24* (2006.01)
*A61B 17/04* (2006.01)

(52) U.S. Cl.
CPC .... *A61F 2/2457* (2013.01); *A61B 2017/0443* (2013.01); *A61B 2017/0454* (2013.01);
(Continued)

(58) Field of Classification Search
CPC ............ A61F 2/2457; A61F 2220/0016; A61F 2230/0091; A61B 2017/0443;
(Continued)

(56) References Cited

U.S. PATENT DOCUMENTS 2,751,908 A 6/1956 Wallace
3,664,330 A 5/1972 Deutsch
(Continued)

FOREIGN PATENT DOCUMENTS

EP 1039851 B1 7/2005
EP 1637091 A2 3/2006
(Continued)

OTHER PUBLICATIONS

US 6,197,052 B1, 03/2001, Cosgrove et al. (withdrawn)
(Continued)

*Primary Examiner* — Matthew J Lawson
*Assistant Examiner* — Cassidy N Stuhlsatz
(74) *Attorney, Agent, or Firm* — MERCHANT & GOULD P.C.

(57) ABSTRACT

An anchor assembly is configured to implant a cardiac anchor into a heart wall of a patient to anchor a suture configured to extend from a valve leaflet of the heart as an artificial chordae. The anchor assembly can include an anchor hub defining an open interior and a helical coil extending distally from the anchor hub and having a sharpened tip configured to embed the helical coil into the heart wall upon rotation of the helical coil. A spring can be disposed within the open interior of the anchor hub. Compressing the spring distally can create an open space within the open interior of the anchor hub for a suture extending through the anchor hub to slide freely and releasing com-
(Continued)

pression on the spring can cause the spring to expand in a proximal direction to clamp the suture within the open interior of the anchor hub.

17 Claims, 33 Drawing Sheets

(52) U.S. Cl.
CPC ................ *A61F 2220/0016* (2013.01); *A61F 2230/0091* (2013.01)

(58) Field of Classification Search
CPC .... A61B 2017/0454; A61B 2017/0409; A61B 17/0401
See application file for complete search history.

(56) References Cited

U.S. PATENT DOCUMENTS

| | | |
|---|---|---|
| 3,667,474 A | 6/1972 | Lapkin |
| 3,842,840 A | 10/1974 | Schweizer |
| 4,258,716 A | 3/1981 | Sutherland |
| 4,351,345 A | 9/1982 | Carney |
| 4,759,348 A | 7/1988 | Cawood |
| 4,836,204 A | 6/1989 | Landymore et al. |
| 4,935,027 A | 6/1990 | Yoon |
| 4,957,498 A | 9/1990 | Caspari |
| 4,967,498 A | 9/1990 | Caspari |
| 4,960,424 A | 10/1990 | Grooters |
| 4,967,798 A | 11/1990 | Hammer |
| 4,972,874 A | 11/1990 | Jackson |
| 5,053,013 A | 10/1991 | Ensminger |
| 5,059,201 A | 10/1991 | Asnis |
| 5,211,650 A | 5/1993 | Noda |
| 5,297,536 A | 3/1994 | Wilk |
| 5,304,185 A | 4/1994 | Taylor |
| 5,312,423 A | 5/1994 | Rosenbluth et al. |
| 5,336,229 A | 8/1994 | Noda |
| 5,383,877 A | 1/1995 | Clarke |
| 5,431,666 A | 7/1995 | Sauer et al. |
| 5,452,733 A | 9/1995 | Sterman |
| 5,474,519 A | 12/1995 | Bloomer |
| 5,547,455 A | 8/1996 | McKenna et al. |
| 5,556,411 A | 9/1996 | Taoda et al. |
| 5,571,215 A | 11/1996 | Sterman |
| 5,601,578 A | 2/1997 | Murphy |
| 5,626,607 A | 5/1997 | Malecki |
| 5,653,716 A | 8/1997 | Malo et al. |
| 5,662,704 A | 9/1997 | Gross |
| 5,665,100 A | 9/1997 | Yoon |
| 5,667,472 A | 9/1997 | Finn et al. |
| 5,667,473 A | 9/1997 | Finn et al. |
| 5,667,478 A | 9/1997 | McFarlin et al. |
| 5,693,091 A | 12/1997 | Larson, Jr. et al. |
| 5,728,113 A | 3/1998 | Sherts |
| 5,762,458 A | 6/1998 | Wang et al. |
| 5,762,613 A | 6/1998 | Sutton et al. |
| 5,766,163 A | 6/1998 | Mueller et al. |
| 5,769,791 A | 6/1998 | Benaron et al. |
| 5,772,597 A | 6/1998 | Goldberger et al. |
| 5,772,672 A | 6/1998 | Toy et al. |
| 5,785,658 A | 7/1998 | Benaron et al. |
| 5,797,960 A | 8/1998 | Stevens et al. |
| 5,830,231 A | 11/1998 | Geiges, Jr. |
| 5,839,639 A | 11/1998 | Sauer et al. |
| 5,857,961 A | 1/1999 | Vanden Hoek et al. |
| 5,897,564 A | 4/1999 | Schulze et al. |
| 5,908,428 A | 6/1999 | Scirica et al. |
| 5,908,429 A | 6/1999 | Yoon |
| 5,919,128 A | 7/1999 | Fitch |
| 5,961,440 A | 10/1999 | Schweich, Jr. |
| 5,972,004 A | 10/1999 | Williamson et al. |
| 5,972,030 A | 10/1999 | Garrison et al. |
| 5,984,939 A | 11/1999 | Yoon |
| 5,993,466 A | 11/1999 | Yoon |
| 5,993,467 A | 11/1999 | Yoon |
| 6,022,360 A | 2/2000 | Reimels et al. |
| 6,045,497 A | 4/2000 | Schweich, Jr. |
| 6,050,936 A | 4/2000 | Schweich, Jr. |
| 6,053,933 A | 4/2000 | Balazs et al. |
| 6,059,715 A | 5/2000 | Schweich, Jr. |
| 6,074,417 A | 6/2000 | Peredo |
| 6,077,214 A | 6/2000 | Mortier et al. |
| 6,117,144 A | 9/2000 | Nobles et al. |
| 6,129,683 A | 10/2000 | Sutton et al. |
| 6,149,660 A | 11/2000 | Laufer et al. |
| 6,152,934 A | 11/2000 | Harper et al. |
| 6,162,168 A | 12/2000 | Schweich, Jr. |
| 6,162,233 A | 12/2000 | Williamson |
| 6,162,234 A | 12/2000 | Freedland et al. |
| 6,165,119 A | 12/2000 | Schweich, Jr. |
| 6,165,120 A | 12/2000 | Schweich, Jr. |
| 6,165,183 A | 12/2000 | Kuehn et al. |
| 6,178,346 B1 | 1/2001 | Amundson et al. |
| 6,179,195 B1 | 1/2001 | Adams et al. |
| 6,183,411 B1 | 2/2001 | Mortier et al. |
| 6,190,357 B1 | 2/2001 | Ferrari et al. |
| 6,234,079 B1 | 5/2001 | Chertkow |
| 6,234,995 B1 | 5/2001 | Peacock, III |
| 6,245,079 B1 | 6/2001 | Nobles et al. |
| 6,260,552 B1 | 7/2001 | Mortier et al. |
| 6,261,222 B1 | 7/2001 | Schweich, Jr. |
| 6,264,602 B1 | 7/2001 | Mortier et al. |
| 6,269,819 B1 | 8/2001 | Oz et al. |
| 6,270,508 B1 | 8/2001 | KIleman et al. |
| 6,283,993 B1 | 9/2001 | Cosgrove et al. |
| 6,312,447 B1 | 11/2001 | Grimes |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,355,050 B1 | 3/2002 | Andreas et al. |
| 6,401,720 B1 | 6/2002 | Stevens et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,419,626 B1 | 7/2002 | Yoon |
| 6,436,107 B1 | 8/2002 | Wang et al. |
| 6,443,922 B1 | 9/2002 | Roberts et al. |
| 6,451,054 B1 | 9/2002 | Stevens |
| 6,461,366 B1 | 10/2002 | Seguin |
| 6,508,777 B1 | 1/2003 | Macoviak et al. |
| 6,514,194 B2 | 2/2003 | Schweich, Jr. et al. |
| 6,533,796 B1 | 3/2003 | Sauer et al. |
| 6,537,198 B1 | 3/2003 | Vidlund et al. |
| 6,537,314 B2 | 3/2003 | Langberg et al. |
| 6,551,331 B2 | 4/2003 | Nobles et al. |
| 6,558,416 B2 | 5/2003 | Cosgrove et al. |
| 6,562,052 B2 | 5/2003 | Nobles et al. |
| 6,564,805 B2 | 5/2003 | Garrison et al. |
| 6,582,388 B1 | 6/2003 | Coleman et al. |
| 6,585,727 B1 | 7/2003 | Cashman et al. |
| 6,589,160 B2 | 7/2003 | Schweich, Jr. et al. |
| 6,602,288 B1 | 8/2003 | Cosgrove et al. |
| 6,616,684 B1 | 9/2003 | Vidlund et al. |
| 6,619,291 B2 | 9/2003 | Hlavka et al. |
| 6,622,730 B2 | 9/2003 | Ekvall et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,629,984 B1 | 10/2003 | Chan |
| 6,645,205 B2 | 11/2003 | Ginn |
| 6,679,268 B2 | 1/2004 | Stevens et al. |
| 6,692,605 B2 | 2/2004 | Kerr et al. |
| 6,695,866 B1 | 2/2004 | Kuehn et al. |
| 6,709,456 B2 | 3/2004 | Langberg et al. |
| 6,718,985 B2 | 4/2004 | Hlavka et al. |
| 6,723,038 B1 | 4/2004 | Schroeder et al. |
| 6,733,509 B2 | 5/2004 | Nobles et al. |
| 6,740,107 B2 | 5/2004 | Loeb et al. |
| 6,743,239 B1 | 6/2004 | Kuehn et al. |
| 6,746,471 B2 | 6/2004 | Mortier et al. |

(56) References Cited

U.S. PATENT DOCUMENTS

| | | |
|---|---|---|
| 6,752,713 B2 | 6/2004 | Johnson, Jr. |
| 6,752,813 B2 | 6/2004 | Goldfarb et al. |
| 6,755,777 B2 | 6/2004 | Schweich, Jr. et al. |
| 6,764,510 B2 | 7/2004 | Vidlund et al. |
| 6,770,083 B2 | 8/2004 | Seguin |
| 6,770,084 B1 | 8/2004 | Bain et al. |
| 6,793,618 B2 | 9/2004 | Schweich, Jr. et al. |
| 6,802,860 B2 | 10/2004 | Cosgrove et al. |
| 6,808,488 B2 | 10/2004 | Mortier et al. |
| 6,810,882 B2 | 11/2004 | Langberg et al. |
| 6,840,246 B2 | 1/2005 | Downing |
| 6,858,003 B2 | 2/2005 | Evans et al. |
| 6,875,224 B2 | 4/2005 | Grimes |
| 6,893,448 B2 | 5/2005 | O'Quinn et al. |
| 6,896,686 B2 | 5/2005 | Weber |
| 6,908,424 B2 | 6/2005 | Mortier et al. |
| 6,918,917 B1 | 7/2005 | Nguyen et al. |
| 6,921,407 B2 | 7/2005 | Nguyen et al. |
| 6,929,715 B2 | 8/2005 | Fladda et al. |
| 6,936,054 B2 | 8/2005 | Chu |
| 6,955,175 B2 | 10/2005 | Stevens et al. |
| 6,962,605 B2 | 11/2005 | Cosgrove et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,991,635 B2 | 1/2006 | Takamoto et al. |
| 6,997,950 B2 | 2/2006 | Chawla |
| 7,004,176 B2 | 2/2006 | Lau |
| 7,004,952 B2 | 2/2006 | Nobles et al. |
| 7,011,669 B2 | 3/2006 | Kimblad |
| 7,044,905 B2 | 5/2006 | Vidlund et al. |
| 7,048,754 B2 | 5/2006 | Martin et al. |
| 7,077,862 B2 | 7/2006 | Vidlund et al. |
| 7,083,628 B2 | 8/2006 | Bachman |
| 7,083,638 B2 | 8/2006 | Foerster |
| 7,090,686 B2 | 8/2006 | Nobles et al. |
| 7,094,244 B2 | 8/2006 | Schreck |
| 7,100,614 B2 | 9/2006 | Stevens et al. |
| 7,112,207 B2 | 9/2006 | Allen et al. |
| 7,112,219 B2 | 9/2006 | Vidlund et al. |
| 7,115,110 B2 | 10/2006 | Frazier et al. |
| 7,118,583 B2 | 10/2006 | O'Quinn et al. |
| 7,122,040 B2 | 10/2006 | Hill et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,217,240 B2 | 5/2007 | Snow |
| 7,226,467 B2 | 6/2007 | Lucatero et al. |
| 7,247,134 B2 | 7/2007 | Vidlund et al. |
| 7,250,028 B2 | 7/2007 | Julian et al. |
| 7,288,097 B2 | 10/2007 | Seguin |
| 7,294,148 B2 | 11/2007 | McCarthy |
| 7,381,210 B2 | 6/2008 | Zarbatany et al. |
| 7,431,692 B2 | 10/2008 | Zollinger |
| 7,464,712 B2 | 12/2008 | Oz et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,386 B1 | 12/2009 | Gammie |
| 7,666,204 B2 | 2/2010 | Thornton et al. |
| 7,815,654 B2 | 10/2010 | Chu |
| 7,879,048 B2 | 2/2011 | Bain et al. |
| 7,887,552 B2 | 2/2011 | Bachman |
| 8,303,622 B2 | 11/2012 | Alkhatib |
| 8,465,500 B2 | 6/2013 | Speziali |
| 8,512,362 B2 | 8/2013 | Ewers et al. |
| 8,545,551 B2 | 10/2013 | Loulmet |
| 8,758,393 B2 | 6/2014 | Zentgraf |
| 8,771,296 B2 | 7/2014 | Nobles et al. |
| 8,938,283 B2 | 1/2015 | Zentgraf et al. |
| 8,968,338 B2 | 3/2015 | Speziali |
| 9,044,221 B2 | 6/2015 | Zengraf et al. |
| 9,192,374 B2 | 11/2015 | Zentgraf |
| 9,364,213 B2 | 6/2016 | Speziali |
| 9,393,080 B2 | 7/2016 | Zentgraf et al. |
| 9,517,337 B2 | 12/2016 | Ollivier |
| 9,572,556 B2 | 2/2017 | Skinlo et al. |
| 9,572,566 B2 | 2/2017 | Skinlo et al. |
| 9,668,860 B2 | 6/2017 | Kudlik et al. |
| 9,700,300 B2 | 7/2017 | Speziali |
| 9,877,833 B1 | 1/2018 | Bishop et al. |
| 10,058,321 B2 | 8/2018 | Sampson et al. |
| 10,065,032 B2 | 9/2018 | Ollivier |
| 10,080,659 B1 | 9/2018 | Zentgraf et al. |
| 10,112,045 B2 | 10/2018 | Anderson et al. |
| 10,130,474 B2 | 11/2018 | Zentgraf et al. |
| 10,213,306 B2 | 2/2019 | Colli |
| 10,314,586 B2 | 6/2019 | Greenberg et al. |
| 10,327,743 B2 | 6/2019 | St. Goar et al. |
| 10,328,272 B2 | 6/2019 | Delanely, Jr. et al. |
| 10,391,306 B2 | 8/2019 | Ma et al. |
| 10,420,645 B2 | 9/2019 | Del Nido et al. |
| 10,499,941 B2 | 12/2019 | Suri |
| 10,507,018 B2 | 12/2019 | Zentgraf |
| 10,548,733 B2 | 2/2020 | Purcell et al. |
| 10,582,924 B2 | 3/2020 | Speziali |
| 10,588,620 B2 | 3/2020 | Caffes et al. |
| 10,653,524 B2 | 5/2020 | Khairkhahan et al. |
| 10,695,178 B2 | 6/2020 | Zentgraf et al. |
| 10,709,433 B2 | 7/2020 | Flanagan et al. |
| 10,765,715 B2 | 9/2020 | Kang et al. |
| 10,856,987 B2 | 12/2020 | Cabiri et al. |
| 10,925,731 B2 | 2/2021 | Bishop et al. |
| 10,966,709 B2 | 4/2021 | Caffes et al. |
| 11,173,030 B2 | 11/2021 | Garvin et al. |
| 11,253,360 B2 | 2/2022 | Smirnov et al. |
| 11,376,126 B2 | 7/2022 | Anderson et al. |
| 2001/0005787 A1 | 6/2001 | Oz |
| 2001/0016675 A1 | 8/2001 | Mortier et al. |
| 2001/0021872 A1 | 9/2001 | Bailey et al. |
| 2002/0013571 A1 | 1/2002 | Goldfarb et al. |
| 2002/0020732 A1 | 2/2002 | Adams et al. |
| 2002/0029080 A1 | 3/2002 | Mortier et al. |
| 2002/0049402 A1 | 4/2002 | Peacock, III |
| 2002/0077524 A1 | 6/2002 | Schweich, Jr. |
| 2002/0091382 A1 | 7/2002 | Hooven |
| 2002/0169359 A1 | 11/2002 | McCarthy |
| 2002/0173694 A1 | 11/2002 | Mortier et al. |
| 2002/0183766 A1 | 12/2002 | Seguin |
| 2002/0183787 A1 | 12/2002 | Wahr et al. |
| 2003/0004562 A1 | 1/2003 | DiCarlo |
| 2003/0032979 A1 | 2/2003 | Mortier et al. |
| 2003/0050529 A1 | 3/2003 | Vidlund et al. |
| 2003/0050693 A1 | 3/2003 | Quijano |
| 2003/0078599 A1 | 4/2003 | O'Quinn et al. |
| 2003/0078600 A1 | 4/2003 | O'Quinn et al. |
| 2003/0105519 A1 | 6/2003 | Fasol |
| 2003/0120341 A1 | 6/2003 | Shennib et al. |
| 2003/0130731 A1 | 7/2003 | Vidlund et al. |
| 2003/0163029 A1 | 8/2003 | Sonnenschein et al. |
| 2003/0166992 A1 | 9/2003 | Schweich, Jr. |
| 2003/0167071 A1 | 9/2003 | Martin et al. |
| 2003/0171641 A1 | 9/2003 | Schweich, Jr. |
| 2003/0181928 A1 | 9/2003 | Vidlund et al. |
| 2003/0187457 A1 | 10/2003 | Weber |
| 2003/0195529 A1 | 10/2003 | Takamoto et al. |
| 2003/0199975 A1 | 10/2003 | Gabbay |
| 2004/0003819 A1 | 1/2004 | St. Goar |
| 2004/0030382 A1 | 2/2004 | St. Goar |
| 2004/0039442 A1 | 2/2004 | St. Goar |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049552 A1 | 3/2004 | Motoyama |
| 2004/0087975 A1 | 5/2004 | Lucatero et al. |
| 2004/0087978 A1 | 5/2004 | Velez et al. |
| 2004/0092962 A1 | 5/2004 | Thornton et al. |
| 2004/0093023 A1 | 5/2004 | Allen et al. |
| 2004/0097805 A1 | 5/2004 | Verard et al. |
| 2004/0116767 A1 | 6/2004 | Lebovic |
| 2004/0122448 A1 | 6/2004 | Levine |
| 2004/0127983 A1 | 7/2004 | Mortier et al. |
| 2004/0133063 A1 | 7/2004 | McCarthy et al. |

(56) References Cited

U.S. PATENT DOCUMENTS

| | | |
|---|---|---|
| 2004/0167374 A1 | 8/2004 | Schweich et al. |
| 2004/0167539 A1 | 8/2004 | Kuehn et al. |
| 2004/0220593 A1 | 11/2004 | Grennhalgh |
| 2004/0225300 A1 | 11/2004 | Goldfarb et al. |
| 2004/0225304 A1 | 11/2004 | Vidlund et al. |
| 2004/0236353 A1 | 11/2004 | Bain et al. |
| 2004/0236354 A1 | 11/2004 | Seguin |
| 2004/0236373 A1 | 11/2004 | Anspach, III |
| 2004/0243229 A1 | 12/2004 | Vidlund et al. |
| 2004/0249367 A1 | 12/2004 | Saadat et al. |
| 2004/0267083 A1 | 12/2004 | McCarthy |
| 2005/0004668 A1 | 1/2005 | Aklog et al. |
| 2005/0021055 A1 | 1/2005 | Toubia et al. |
| 2005/0021056 A1 | 1/2005 | St. Goar |
| 2005/0021057 A1 | 1/2005 | St. Goar |
| 2005/0033446 A1 | 2/2005 | Deem et al. |
| 2005/0044365 A1 | 2/2005 | Bachman |
| 2005/0065396 A1 | 3/2005 | Mortier et al. |
| 2005/0075723 A1 | 4/2005 | Schroeder et al. |
| 2005/0075727 A1 | 4/2005 | Wheatley |
| 2005/0101975 A1 | 5/2005 | Nguyen et al. |
| 2005/0125011 A1 | 6/2005 | Spence et al. |
| 2005/0131277 A1 | 6/2005 | Schweich, Jr. |
| 2005/0131533 A1 | 6/2005 | Alfieri et al. |
| 2005/0143620 A1 | 6/2005 | Mortier et al. |
| 2005/0148815 A1 | 7/2005 | Mortier et al. |
| 2005/0149014 A1 | 7/2005 | Hauck et al. |
| 2005/0154402 A1 | 7/2005 | Sauer et al. |
| 2005/0165419 A1 | 7/2005 | Sauer et al. |
| 2005/0171601 A1 | 8/2005 | Cosgrove |
| 2005/0216039 A1 | 9/2005 | Lederman |
| 2005/0240202 A1 | 10/2005 | Shennib et al. |
| 2005/0245932 A1 | 11/2005 | Fanton |
| 2005/0250987 A1 | 11/2005 | Ewers et al. |
| 2005/0251187 A1 | 11/2005 | Beane et al. |
| 2005/0251201 A1 | 11/2005 | Roue et al. |
| 2005/0251210 A1* | 11/2005 | Westra ............... A61B 17/0469 606/232 |
| 2006/0020275 A1 | 1/2006 | Goldfarb et al. |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0058871 A1 | 3/2006 | Zakay et al. |
| 2006/0074484 A1 | 4/2006 | Huber |
| 2006/0074485 A1 | 4/2006 | Realyvasquez |
| 2006/0089671 A1 | 4/2006 | Goldfarb et al. |
| 2006/0100699 A1 | 5/2006 | Vidlund et al. |
| 2006/0106305 A1 | 5/2006 | Lau |
| 2006/0106405 A1 | 5/2006 | Fann et al. |
| 2006/0106422 A1* | 5/2006 | Del Rio ............. A61B 17/0401 606/232 |
| 2006/0127509 A1 | 6/2006 | Eckman |
| 2006/0135993 A1 | 6/2006 | Seguin |
| 2006/0149123 A1 | 7/2006 | Vidlund et al. |
| 2006/0161040 A1 | 7/2006 | McCarthy |
| 2006/0161193 A1 | 7/2006 | Beane et al. |
| 2006/0184203 A1 | 8/2006 | Martin et al. |
| 2006/0195012 A1 | 8/2006 | Mortier et al. |
| 2006/0195134 A1 | 8/2006 | Crittenden |
| 2006/0195183 A1 | 8/2006 | Navia et al. |
| 2006/0212071 A1 | 9/2006 | Ginn et al. |
| 2006/0241340 A1 | 10/2006 | Vidlund |
| 2006/0287657 A1 | 12/2006 | Bachman |
| 2007/0002627 A1 | 1/2007 | Youn |
| 2007/0027451 A1 | 2/2007 | Desinger et al. |
| 2007/0038293 A1 | 2/2007 | St. Goar et al. |
| 2007/0049952 A1 | 3/2007 | Weiss |
| 2007/0050022 A1 | 3/2007 | Vidlund et al. |
| 2007/0055303 A1 | 3/2007 | Vidlund et al. |
| 2007/0088375 A1 | 4/2007 | Beane et al. |
| 2007/0100356 A1 | 5/2007 | Lucatero et al. |
| 2007/0112244 A1 | 5/2007 | McCarthy |
| 2007/0118151 A1 | 5/2007 | Davidson |
| 2007/0118154 A1 | 5/2007 | Crabtree |
| 2007/0118155 A1 | 5/2007 | Goldfarb et al. |
| 2007/0118213 A1 | 5/2007 | Loulmet |
| 2007/0129737 A1 | 6/2007 | Goldfarb et al. |
| 2007/0179511 A1 | 8/2007 | Paolitto |
| 2007/0197858 A1 | 8/2007 | Goldfarb et al. |
| 2007/0203391 A1 | 8/2007 | Bloom et al. |
| 2007/0213582 A1 | 9/2007 | Zollinger et al. |
| 2007/0232941 A1 | 10/2007 | Rabinovich |
| 2007/0239272 A1 | 10/2007 | Navia et al. |
| 2007/0265643 A1 | 11/2007 | Beane et al. |
| 2007/0299468 A1 | 12/2007 | Viola |
| 2008/0004485 A1 | 1/2008 | Moreschi |
| 2008/0027468 A1 | 1/2008 | Fenton |
| 2008/0051703 A1 | 2/2008 | Thornton et al. |
| 2008/0065011 A1 | 3/2008 | Marchand et al. |
| 2008/0065156 A1 | 3/2008 | Hauser et al. |
| 2008/0065205 A1 | 3/2008 | Nguyen et al. |
| 2008/0086138 A1 | 4/2008 | Stone |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb et al. |
| 2008/0109069 A1 | 5/2008 | Coleman et al. |
| 2008/0125860 A1 | 5/2008 | Webler et al. |
| 2008/0125861 A1 | 5/2008 | Webler et al. |
| 2008/0167714 A1 | 7/2008 | St. Goar |
| 2008/0183194 A1 | 7/2008 | Goldfarb et al. |
| 2008/0188873 A1 | 8/2008 | Speziali |
| 2008/0195126 A1 | 8/2008 | Solem |
| 2008/0195200 A1 | 8/2008 | Vidlund et al. |
| 2008/0208006 A1 | 8/2008 | Farr |
| 2008/0228223 A1 | 9/2008 | Alkhatib |
| 2008/0228266 A1* | 9/2008 | McNamara ........... A61F 2/2445 623/2.36 |
| 2008/0243245 A1 | 10/2008 | Thamber et al. |
| 2009/0062819 A1 | 3/2009 | Burkhart et al. |
| 2009/0093670 A1 | 4/2009 | Annest et al. |
| 2009/0105729 A1 | 4/2009 | Zentgraf |
| 2009/0105751 A1 | 4/2009 | Zentgraf |
| 2009/0125038 A1 | 5/2009 | Ewers et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. |
| 2009/0192598 A1 | 7/2009 | Lattouf et al. |
| 2009/0259304 A1 | 10/2009 | O'Beirne et al. |
| 2009/0326578 A1 | 12/2009 | Ewers et al. |
| 2010/0030061 A1 | 2/2010 | Canfield et al. |
| 2010/0030242 A1 | 2/2010 | Nobles et al. |
| 2010/0042147 A1 | 2/2010 | Janovsky et al. |
| 2010/0121349 A1 | 5/2010 | Meier |
| 2010/0160726 A1 | 6/2010 | Windheuser |
| 2010/0161041 A1 | 6/2010 | Maisano et al. |
| 2010/0174297 A1 | 7/2010 | Speziali |
| 2010/0185172 A1 | 7/2010 | Fabro |
| 2010/0217283 A1 | 8/2010 | St. Goar |
| 2010/0298929 A1 | 11/2010 | Thornton et al. |
| 2011/0011917 A1 | 1/2011 | Loulmet |
| 2011/0106245 A1 | 5/2011 | Miller et al. |
| 2011/0112576 A1 | 5/2011 | Nguyen |
| 2011/0202127 A1 | 8/2011 | Mauch et al. |
| 2011/0288635 A1 | 11/2011 | Miller et al. |
| 2012/0071922 A1 | 3/2012 | Shanley et al. |
| 2012/0184971 A1 | 7/2012 | Zentgraf et al. |
| 2013/0018393 A1 | 1/2013 | Bengtson |
| 2013/0035757 A1 | 2/2013 | Zentgraf et al. |
| 2013/0079873 A1 | 3/2013 | Migliazza et al. |
| 2013/0085529 A1 | 4/2013 | Housman |
| 2013/0090672 A1* | 4/2013 | Butler ................. A61B 34/70 606/151 |
| 2013/0096672 A1 | 4/2013 | Reich et al. |
| 2013/0119108 A1 | 5/2013 | Altman et al. |
| 2013/0150710 A1 | 6/2013 | Zentgraf et al. |
| 2013/0158600 A1 | 6/2013 | Conklin et al. |
| 2013/0197575 A1 | 8/2013 | Karapetian et al. |
| 2014/0031926 A1 | 1/2014 | Kudlik et al. |
| 2014/0039324 A1 | 2/2014 | Speziali |
| 2014/0276764 A1 | 9/2014 | Shuman et al. |
| 2014/0364875 A1 | 12/2014 | Zentgraf |
| 2015/0119934 A1 | 4/2015 | Shluzas et al. |
| 2015/0148821 A1 | 5/2015 | Speziali |

(56) References Cited

U.S. PATENT DOCUMENTS

| | | |
|---|---|---|
| 2015/0190207 A1 | 7/2015 | Zentgraf et al. |
| 2015/0313620 A1 | 11/2015 | Suri |
| 2015/0313713 A1 | 11/2015 | Zentgraf et al. |
| 2015/0351741 A1 | 12/2015 | Hawkins |
| 2015/0351910 A1 | 12/2015 | Gilmore et al. |
| 2015/0366556 A1 | 12/2015 | Khairkhahan et al. |
| 2016/0058557 A1 | 3/2016 | Reich et al. |
| 2016/0106420 A1 | 4/2016 | Foerster et al. |
| 2016/0143737 A1 | 5/2016 | Zentgraf et al. |
| 2016/0158008 A1 | 6/2016 | Miller et al. |
| 2017/0086975 A1* | 3/2017 | Gilmore ............ A61B 17/0401 |
| 2017/0157391 A1 | 6/2017 | Ollivier |
| 2017/0189006 A1* | 7/2017 | Shluzas .................. A61B 5/00 |
| 2017/0245994 A1 | 8/2017 | Khairkhahan et al. |
| 2017/0252032 A1 | 9/2017 | Nikolai et al. |
| 2017/0258465 A1 | 9/2017 | Maisano |
| 2017/0290582 A1 | 10/2017 | Speziali |
| 2018/0064535 A1 | 3/2018 | Gilmore et al. |
| 2018/0161035 A1 | 6/2018 | Greenberg et al. |
| 2018/0185153 A1 | 7/2018 | Bishop et al. |
| 2018/0280138 A1 | 10/2018 | Colli |
| 2018/0289483 A1 | 10/2018 | Speziali et al. |
| 2019/0053902 A1 | 2/2019 | Zentgraf et al. |
| 2019/0133766 A1 | 5/2019 | Zentgraf et al. |
| 2019/0175344 A1* | 6/2019 | Khairkhahan ........ A61F 2/2454 |
| 2019/0216601 A1 | 7/2019 | Purcell et al. |
| 2019/0224012 A1 | 7/2019 | Colli |
| 2019/0240023 A1* | 8/2019 | Spence .............. A61B 17/0401 |
| 2019/0290260 A1 | 9/2019 | Caffes et al. |
| 2019/0343507 A1 | 11/2019 | Chavan |
| 2019/0343626 A1 | 11/2019 | Smirnov et al. |
| 2019/0343633 A1 | 11/2019 | Garvin et al. |
| 2019/0343634 A1 | 11/2019 | Garvin et al. |
| 2019/0381325 A1 | 12/2019 | Regnier et al. |
| 2020/0093478 A1 | 3/2020 | Caffes et al. |
| 2020/0121314 A1 | 4/2020 | Speziali |
| 2020/0138430 A1 | 5/2020 | Zentgraf |
| 2020/0222186 A1 | 7/2020 | Edmiston et al. |
| 2020/0281582 A1 | 9/2020 | Caffes et al. |
| 2020/0297489 A1 | 9/2020 | Bishop et al. |
| 2020/0330228 A1 | 10/2020 | Anderson et al. |
| 2020/0368022 A1 | 11/2020 | Zentgraf et al. |
| 2020/0383784 A1 | 12/2020 | Albes |
| 2022/0061991 A1 | 3/2022 | Garvin et al. |

FOREIGN PATENT DOCUMENTS

| | | | |
|---|---|---|---|
| EP | 1845861 A2 | 10/2007 | |
| EP | 1408850 B1 | 9/2009 | |
| EP | 2628451 A2 * | 8/2013 | ......... A61B 17/0401 |
| EP | 3441045 A1 | 2/2019 | |
| IL | 223448 A | 3/2017 | |
| JP | H 04307052 A | 10/1992 | |
| JP | 06142114 | 5/1994 | |
| JP | 2004-531337 | 10/2004 | |
| JP | 2007-535342 | 12/2007 | |
| WO | WO 1999/000059 A1 | 1/1999 | |
| WO | WO 1999/030647 A1 | 6/1999 | |
| WO | WO 2000/006026 A2 | 2/2000 | |
| WO | WO 2000/006027 A2 | 2/2000 | |
| WO | WO 2000/006028 A1 | 2/2000 | |
| WO | WO 2000/016700 A1 | 3/2000 | |
| WO | WO 2001/066018 A1 | 9/2001 | |
| WO | WO 2001/095809 A1 | 12/2001 | |
| WO | WO 2003/001893 A2 | 1/2003 | |
| WO | WO 2003/059209 A2 | 7/2003 | |
| WO | WO 2003/079937 A2 | 10/2003 | |
| WO | WO 2003/082157 A2 | 10/2003 | |
| WO | WO 2003/082158 A1 | 10/2003 | |
| WO | WO 2004/021893 A1 | 3/2004 | |
| WO | WO 2004/043265 A2 | 5/2004 | |
| WO | WO 2005/039428 A2 | 5/2005 | |
| WO | WO 2005/087140 A1 | 9/2005 | |
| WO | WO 2005/094525 A2 | 10/2005 | |
| WO | WO 2006/012750 A1 | 2/2006 | |
| WO | WO 2006/032051 A2 | 3/2006 | |
| WO | WO 2006/065966 A2 | 6/2006 | |
| WO | WO 2006/078694 A2 | 7/2006 | |
| WO | WO 2006/116310 A2 | 11/2006 | |
| WO | WO 2006/127509 A2 | 11/2006 | |
| WO | WO 2007/002627 A1 | 1/2007 | |
| WO | WO 2007/027451 A2 | 3/2007 | |
| WO | WO 2007/062128 A2 | 5/2007 | |
| WO | WO 2007/081418 A1 | 7/2007 | |
| WO | WO 2007/117612 A1 | 10/2007 | |
| WO | WO 2008/010738 A2 | 1/2008 | |
| WO | WO 2009/052528 A2 | 4/2009 | |
| WO | WO 2011/070477 A1 | 6/2011 | |
| WO | WO 2011/137336 A1 | 11/2011 | |
| WO | WO 2012/167120 A1 | 12/2012 | |
| WO | WO-2018126188 A1 * | 7/2018 | ......... A61B 17/0401 |
| WO | WO 2018/236766 A1 | 12/2018 | |
| WO | WO 2019/183626 A1 | 9/2019 | |
| WO | WO 2019/217638 A1 | 11/2019 | |

OTHER PUBLICATIONS

Interactive Cardio Vascular and Thoracic Surgery; Abstracts; Suppl 3 to vol. 7 (Sep. 2008) 52 pages.
Machine translation of JP 06142114.
Port Access System for Mitral Valve Repair Proves Its Value in Study; MedGadget Jul. 9, 2009 (2 pages).
PCT/US2021/070046, Search Report and Written Opinion dated Jul. 9, 2021, 9 pages.
Application and File history for U.S. Appl. No. 16/406,764, filed May 8, 2019. Inventors: Garvin et al.
Application and File history for U.S. Appl. No. 17/524,499, filed Nov. 11, 2021. Inventors: Garvin et al.
Application and File history for U.S. Appl. No. 16/406,736, filed May 8, 2019. Inventors: Smirnov et al.
Application and File history for U.S. Appl. No. 16/406,799, filed May 8, 2019 Inventors: Garvin et al.
Application and File history for U.S. Appl. No. 16/564,887, filed Sep. 9, 2019. Inventors: Caffes et al.
Application and File history for U.S. Appl. No. 16/745,074, filed Jan. 16, 2020. Inventors: Edmiston et al.
Application and File history for U.S. Appl. No. 16/850,827, filed Apr. 16, 2020. Inventors: Anderson et al.
Application and File history for U.S. Appl. No. 16/363,701, filed Mar. 25, 2019. Inventors: Caffes et al.

* cited by examiner

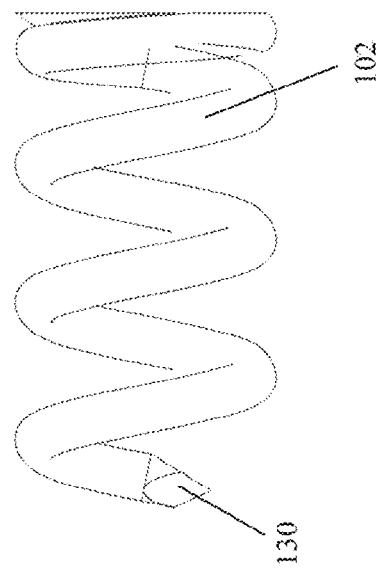
Fig. 3B
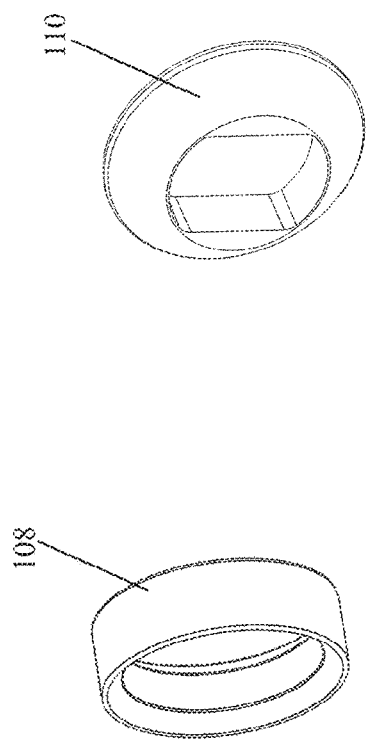
Fig. 3E
Fig. 3D
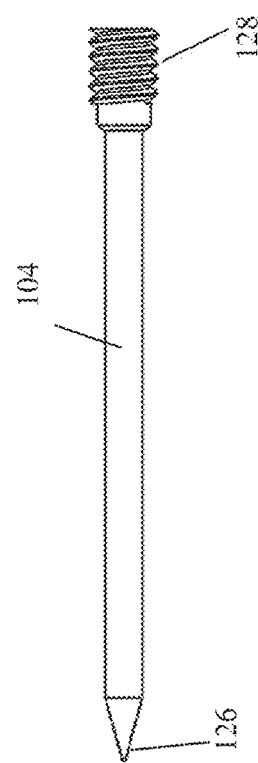
Fig. 3A
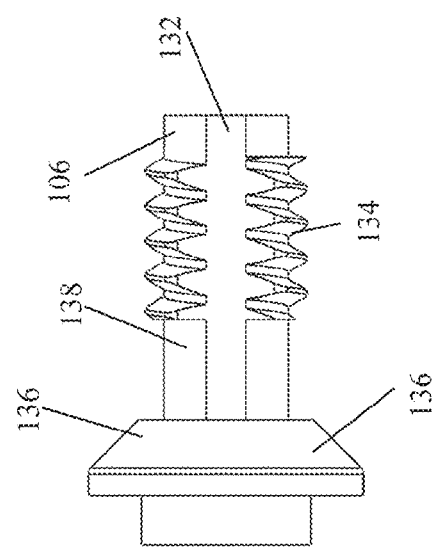
Fig. 3C

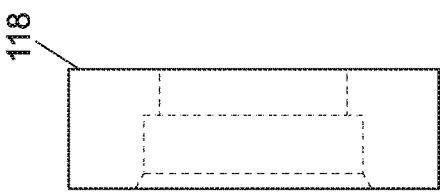
*Fig. 3I*
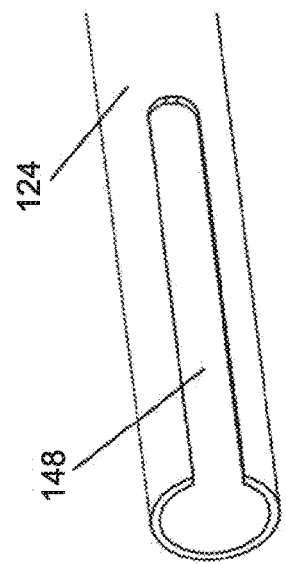
*Fig. 3L*
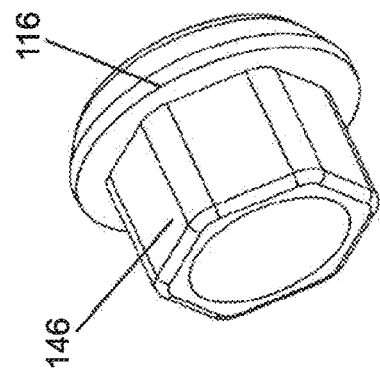
*Fig. 3H*
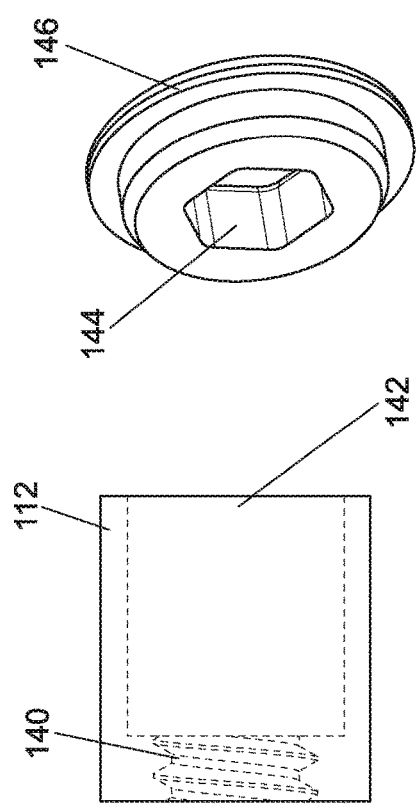
*Fig. 3G*
*Fig. 3F*
*Fig. 3K*
*Fig. 3J*

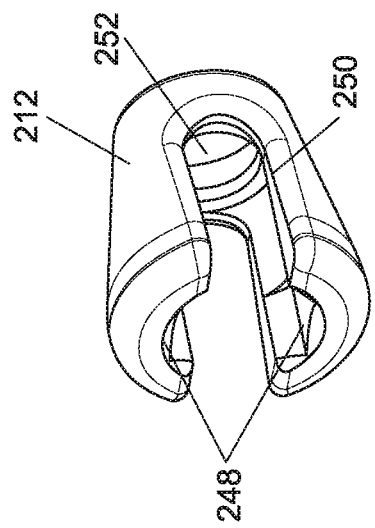
*Fig. 6C*
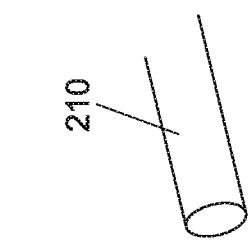
*Fig. 6F*
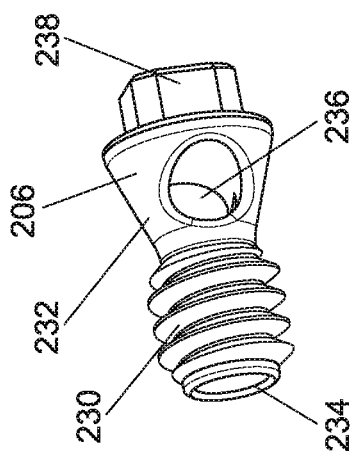
*Fig. 6B*
*Fig. 6E*
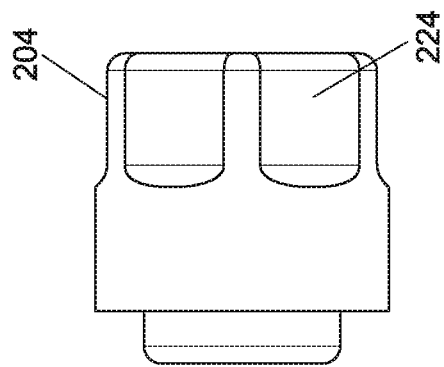
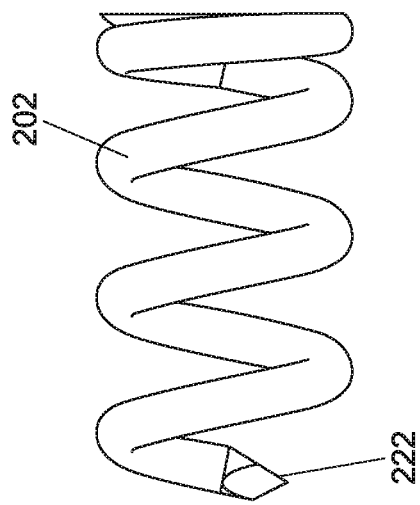
*Fig. 6A*
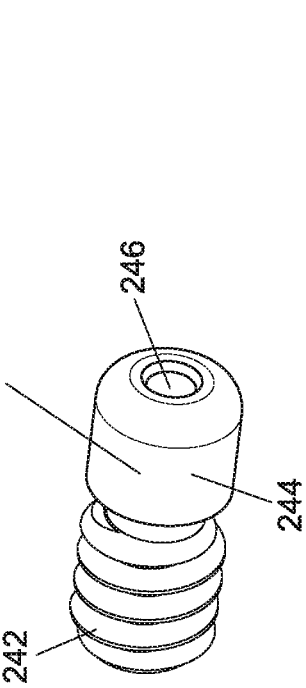
*Fig. 6D*

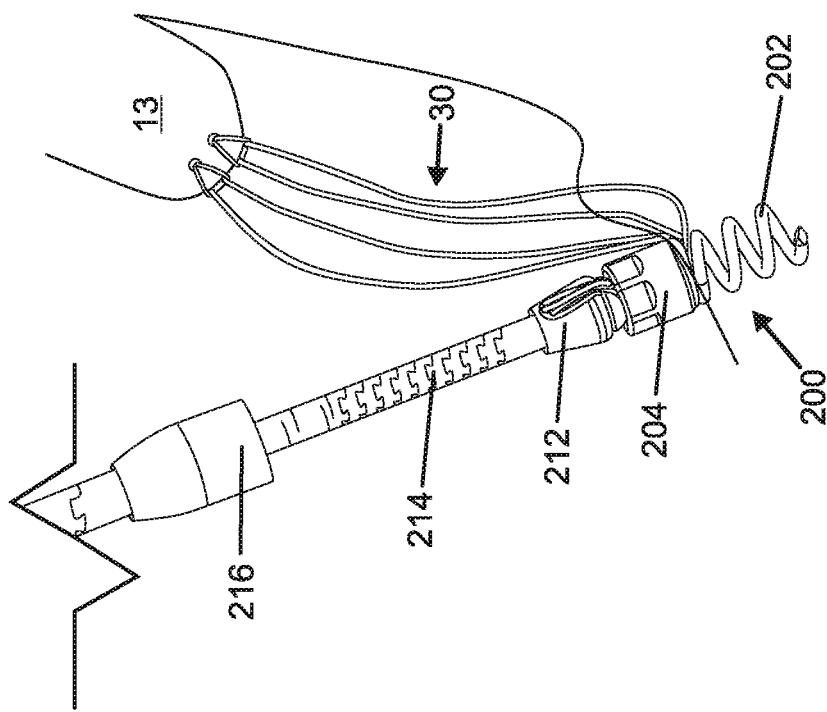
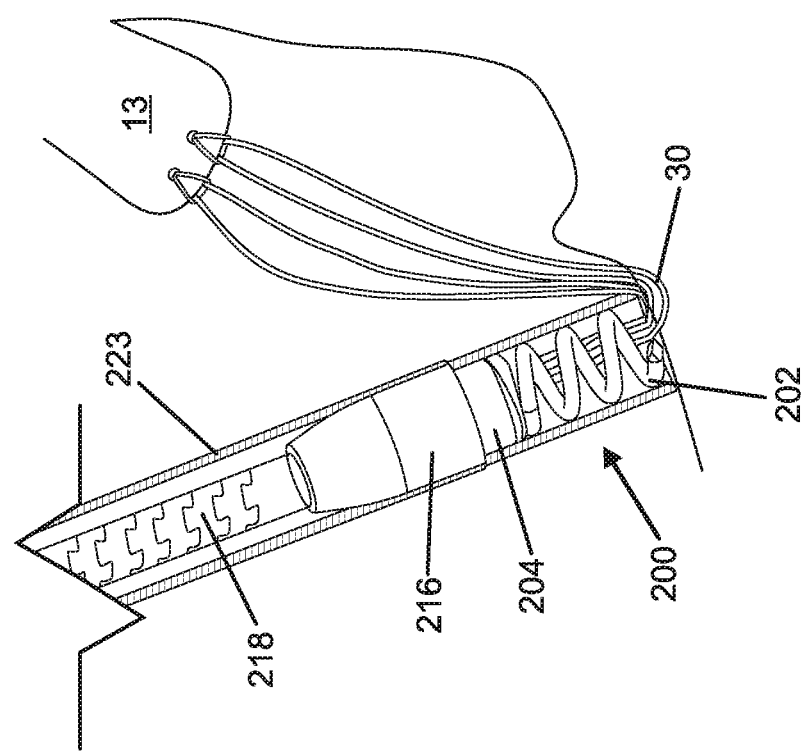
Fig. 7A
Fig. 7B

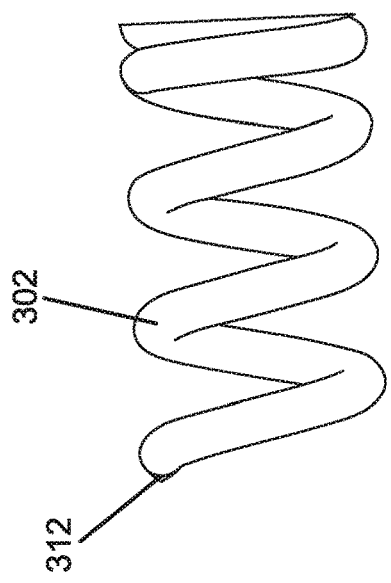
Fig. 9B
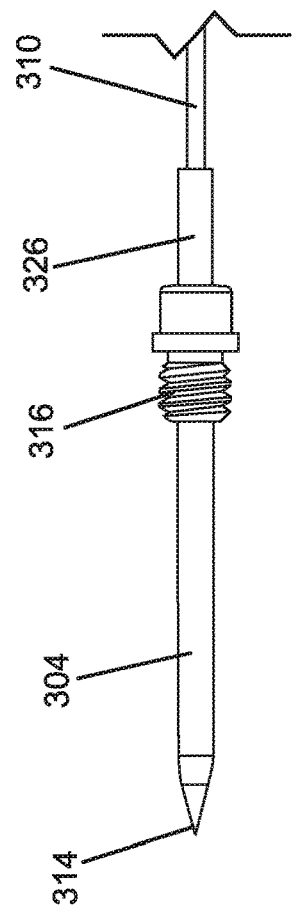
Fig. 9A
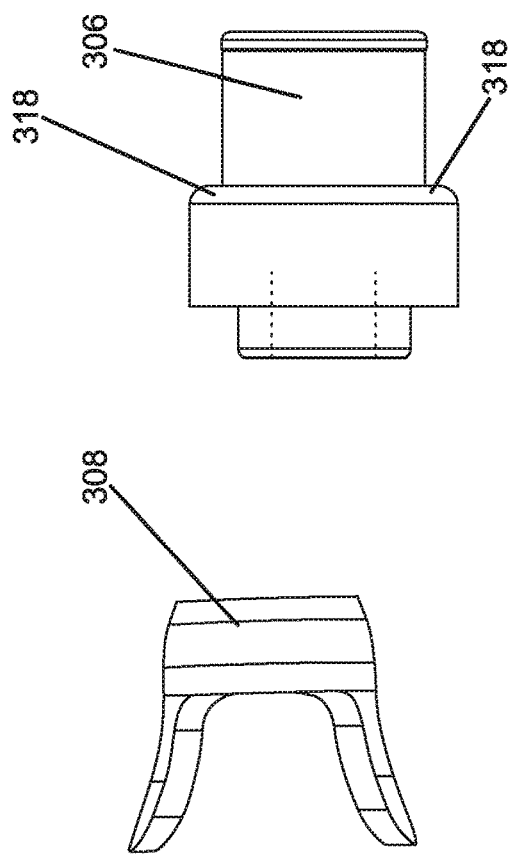
Fig. 9D
Fig. 9C
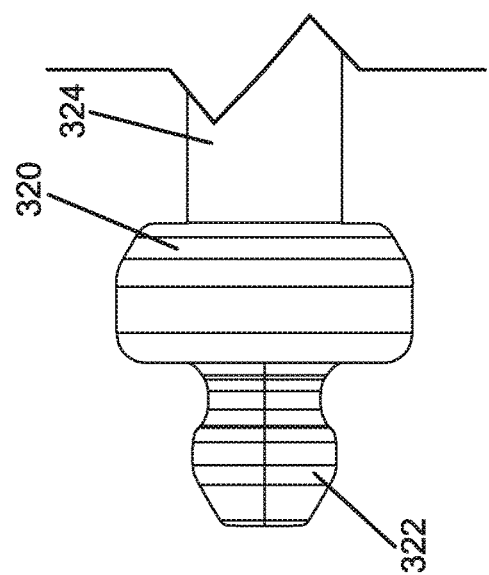
Fig. 9E

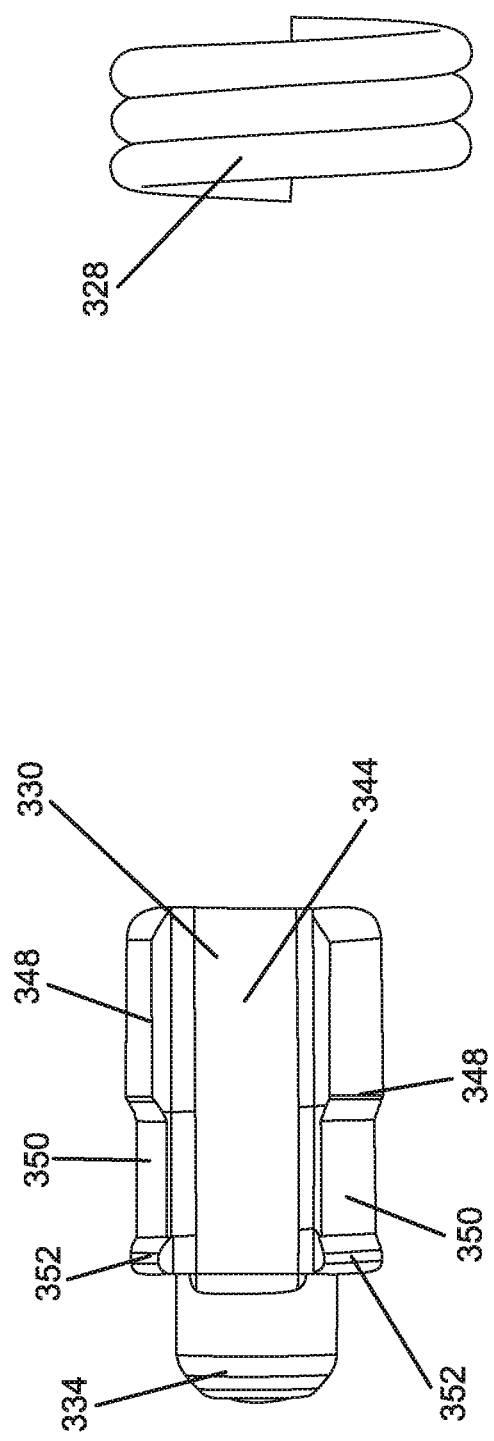
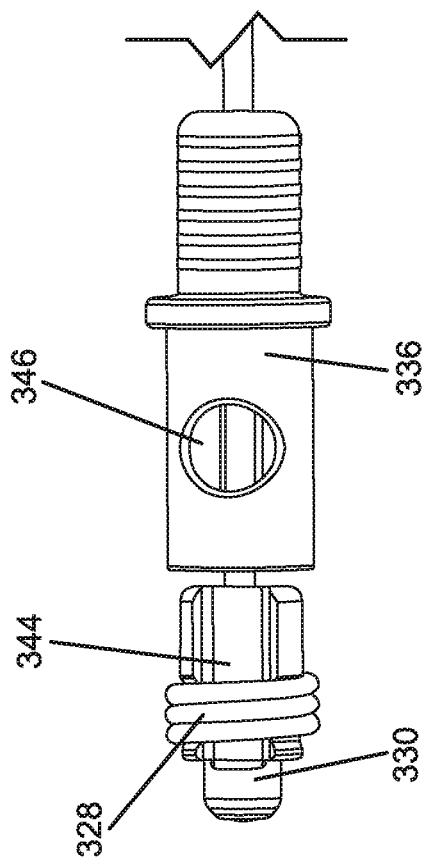
Fig. 9F
Fig. 9G
Fig. 9H

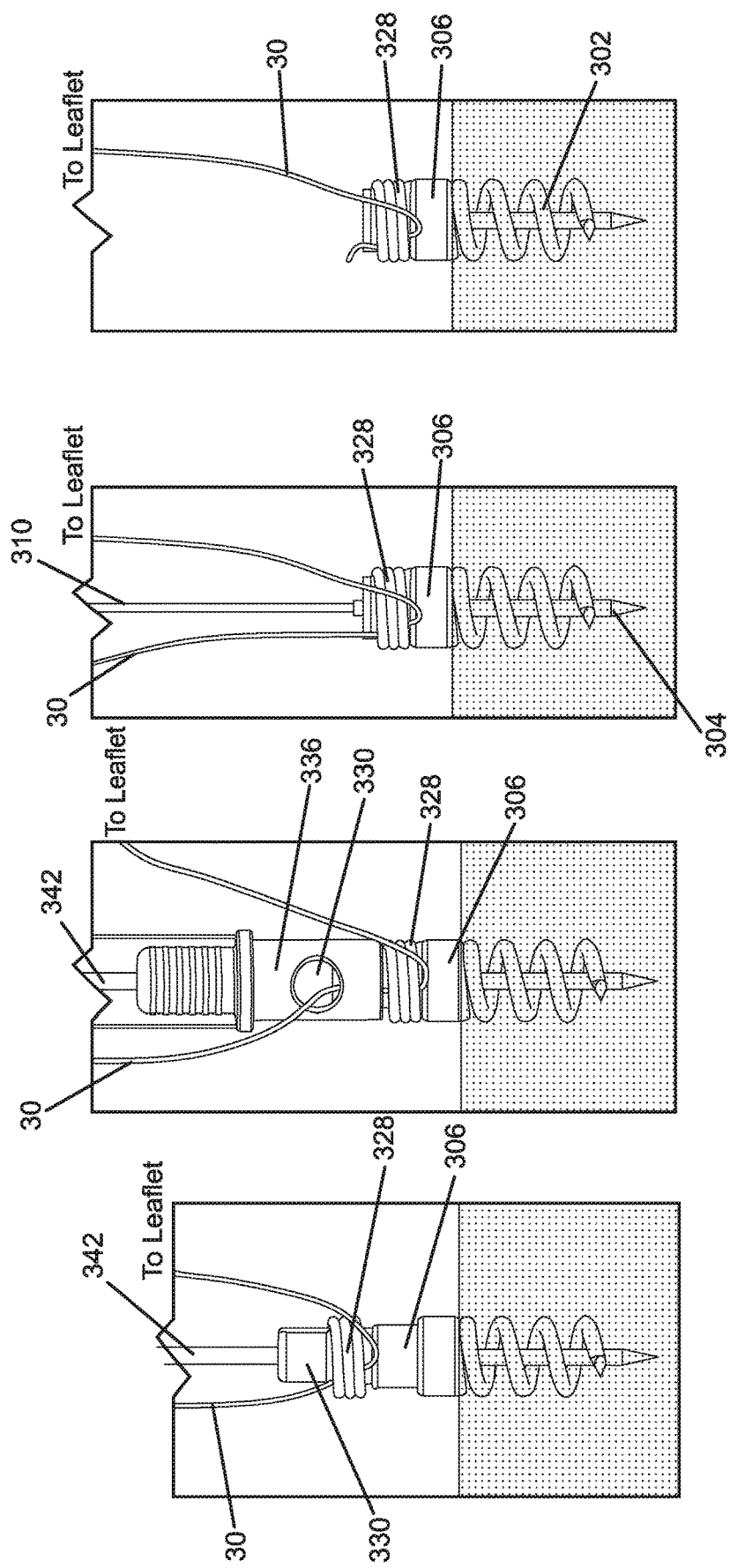

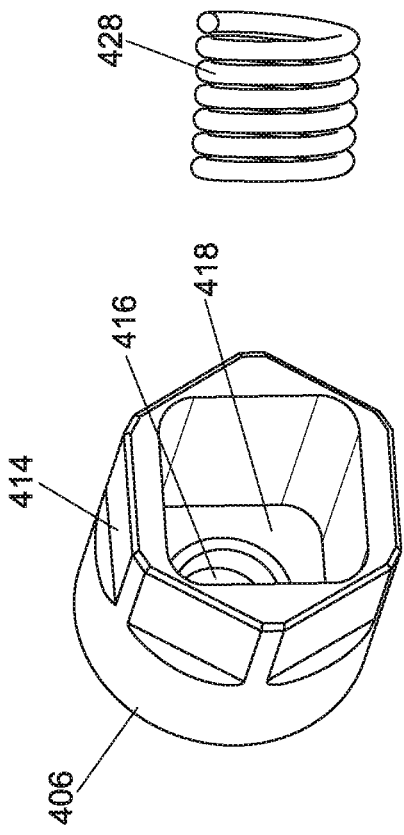
Fig. 12B
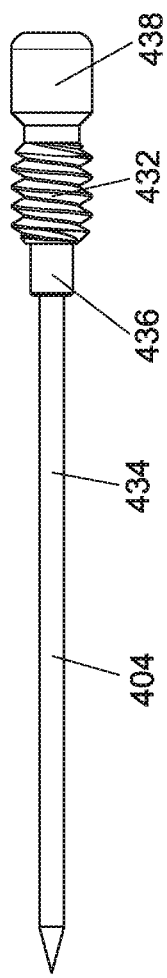
Fig. 12C
Fig. 12F
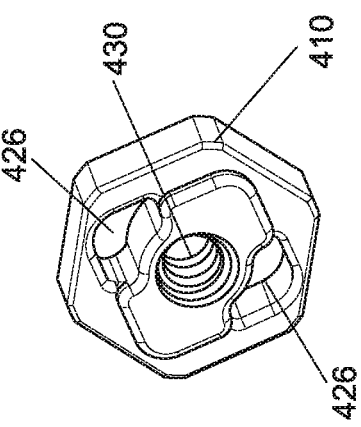
Fig. 12E
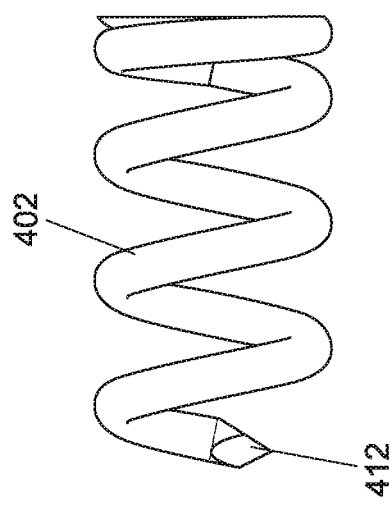
Fig. 12A
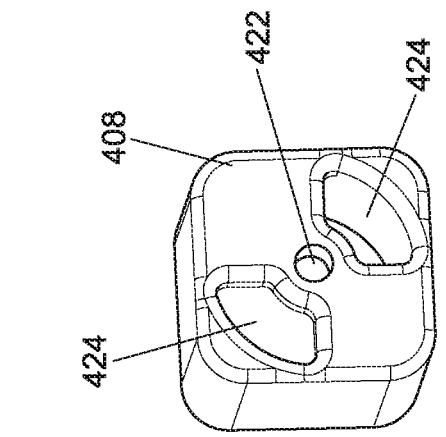
Fig. 12D

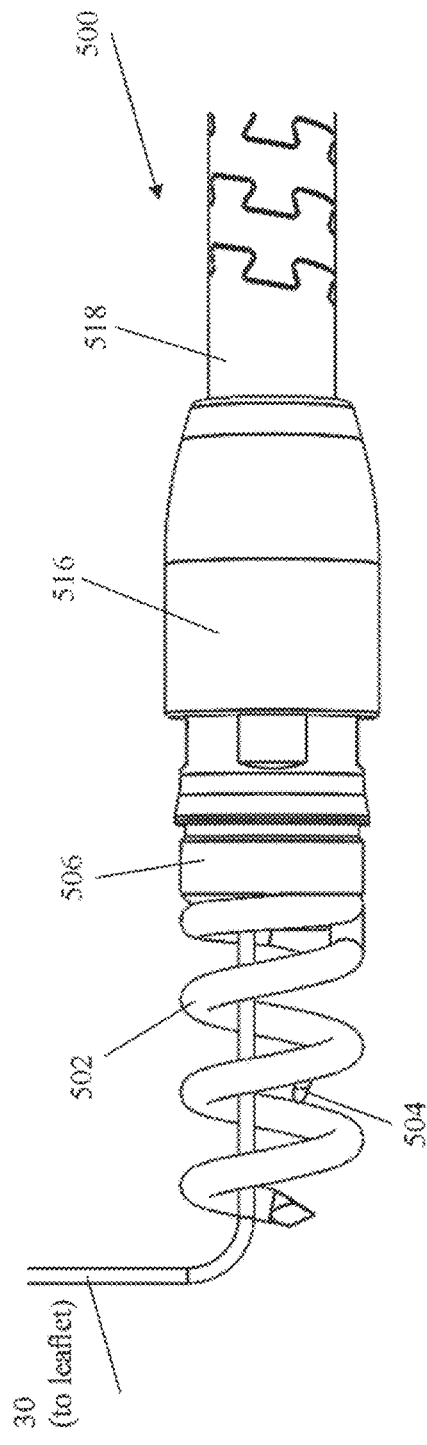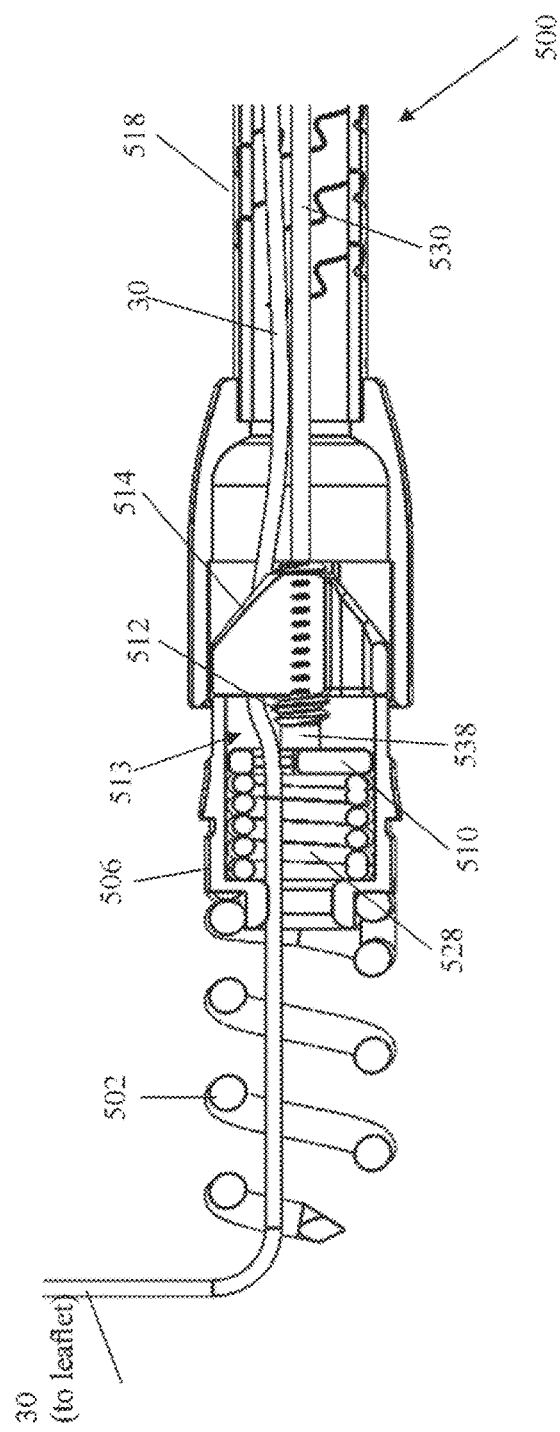
Fig. 13A
Fig. 13B

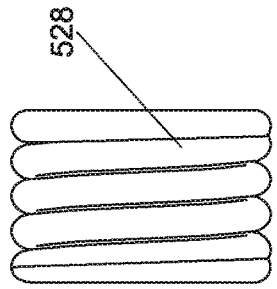
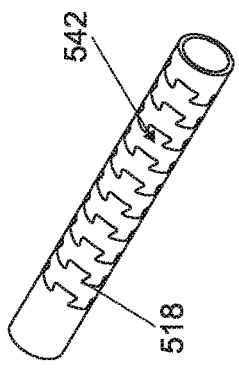
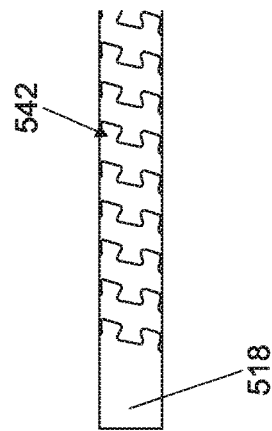
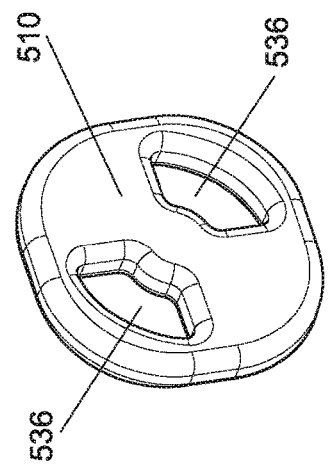
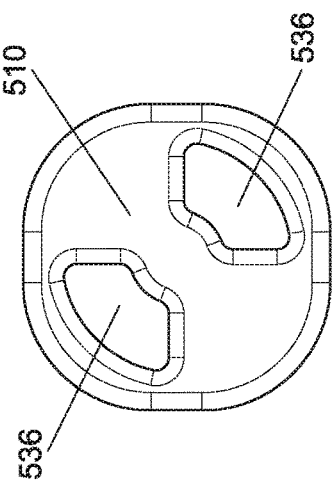
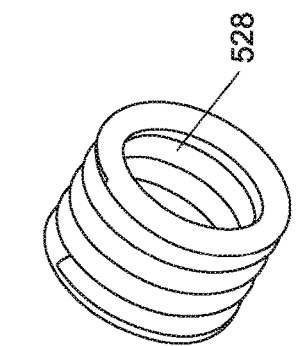
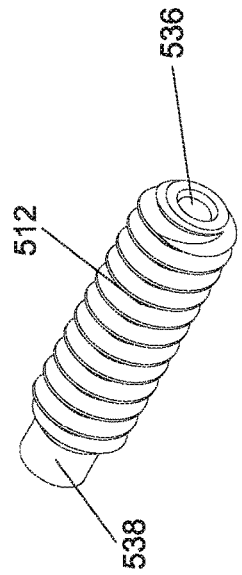
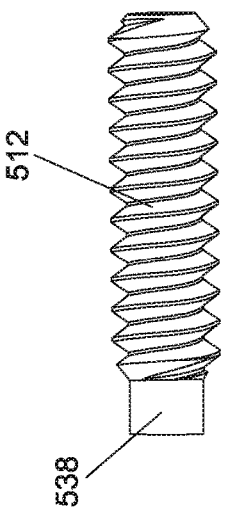
Fig. 14K  Fig. 14N
Fig. 14P
Fig. 14J  Fig. 14M
Fig. 14I  Fig. 14L  Fig. 14O

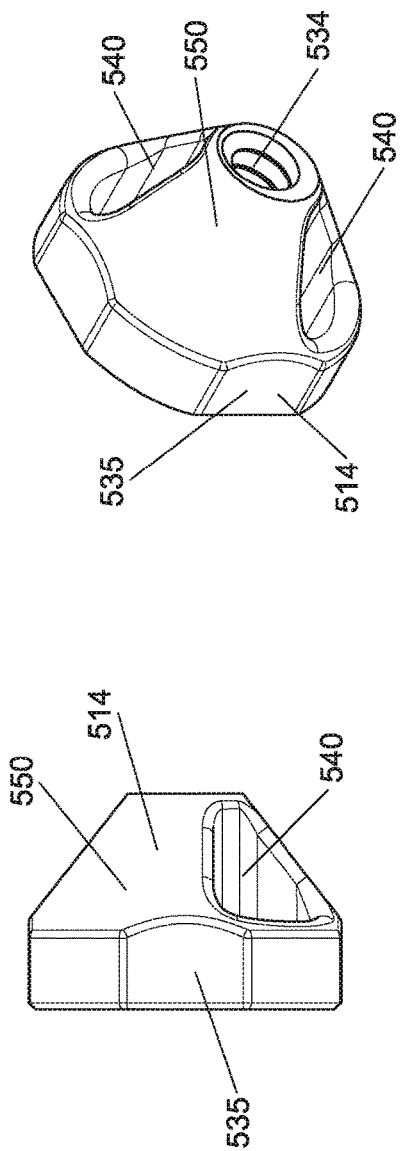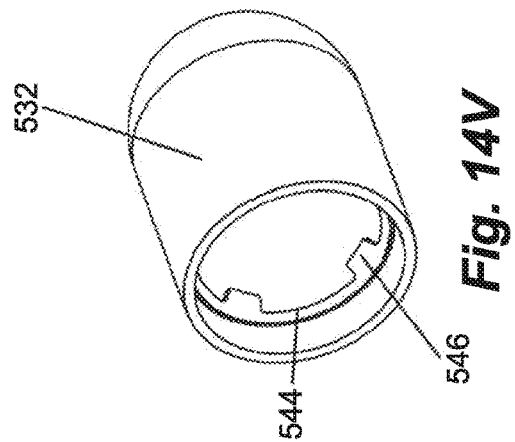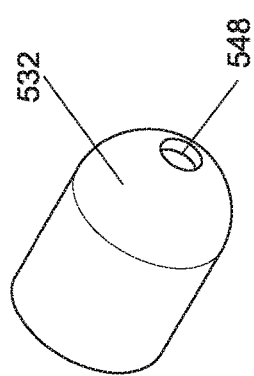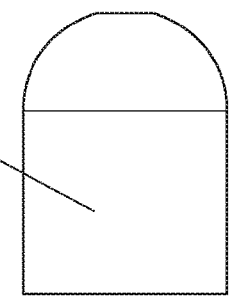
Fig. 14R
Fig. 14V
Fig. 14S
Fig. 14U
Fig. 14Q
Fig. 14T

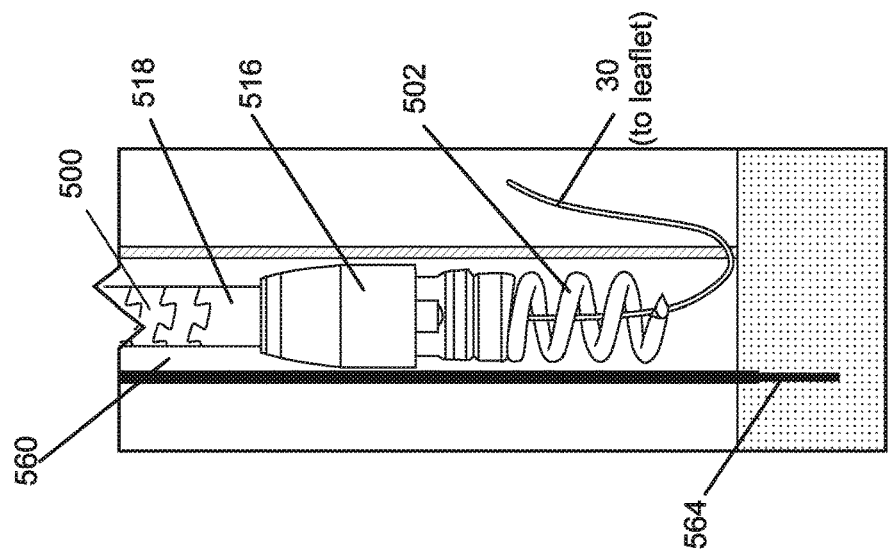
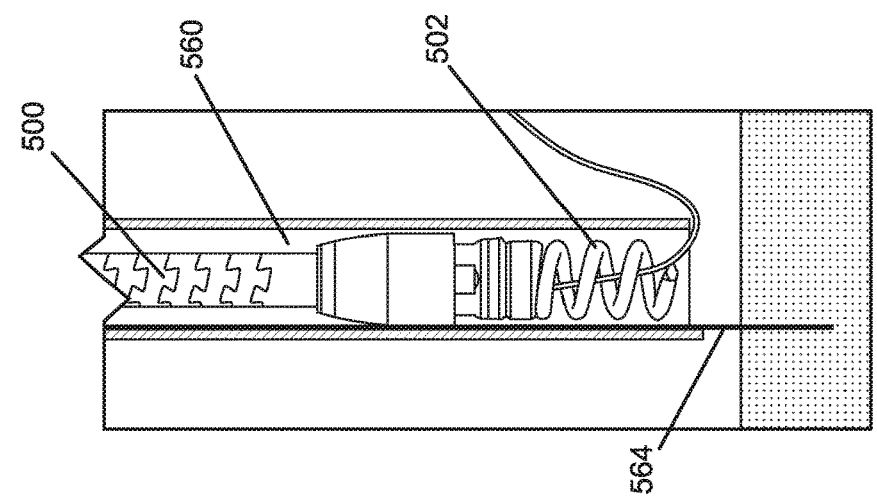
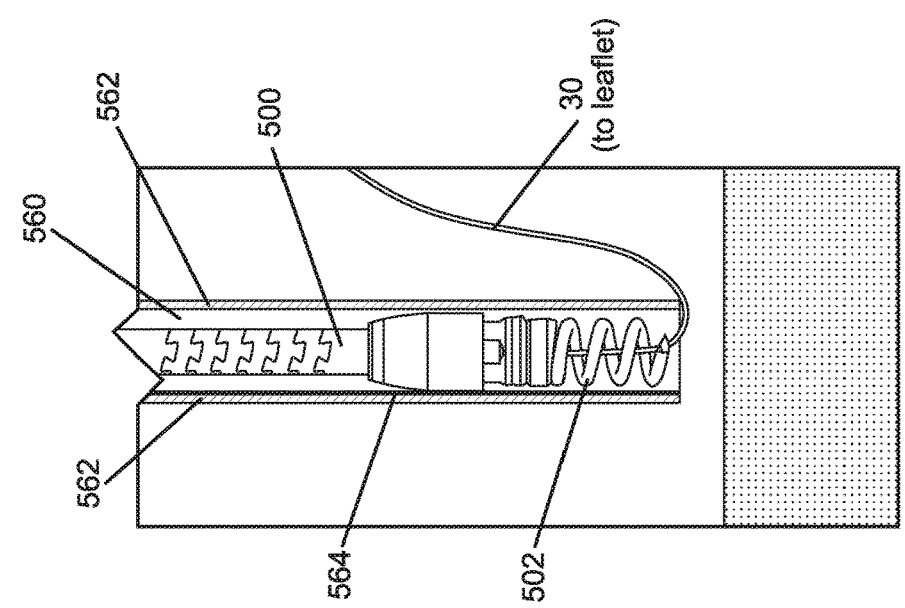

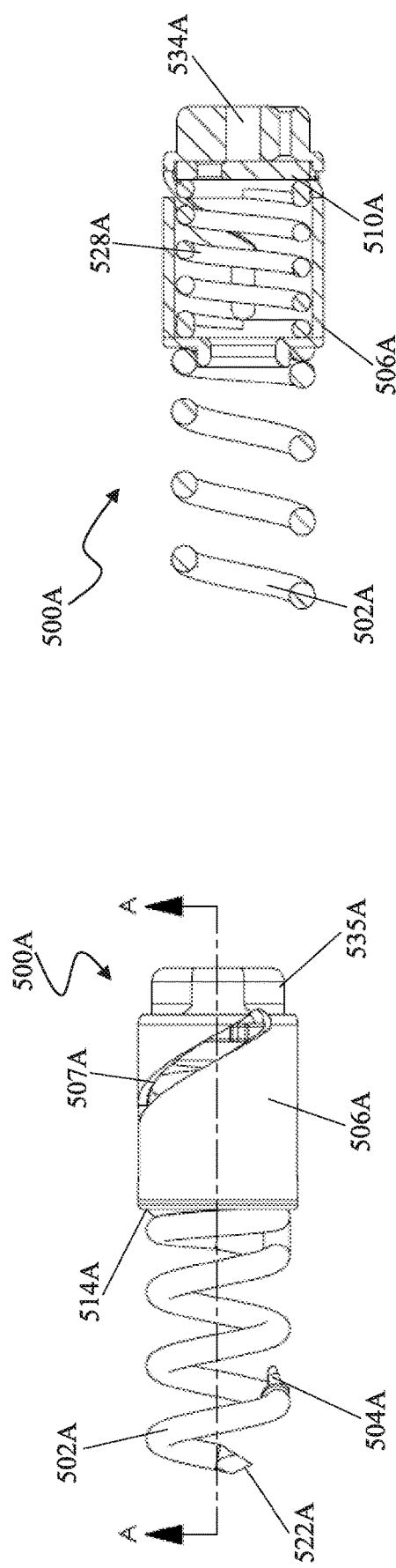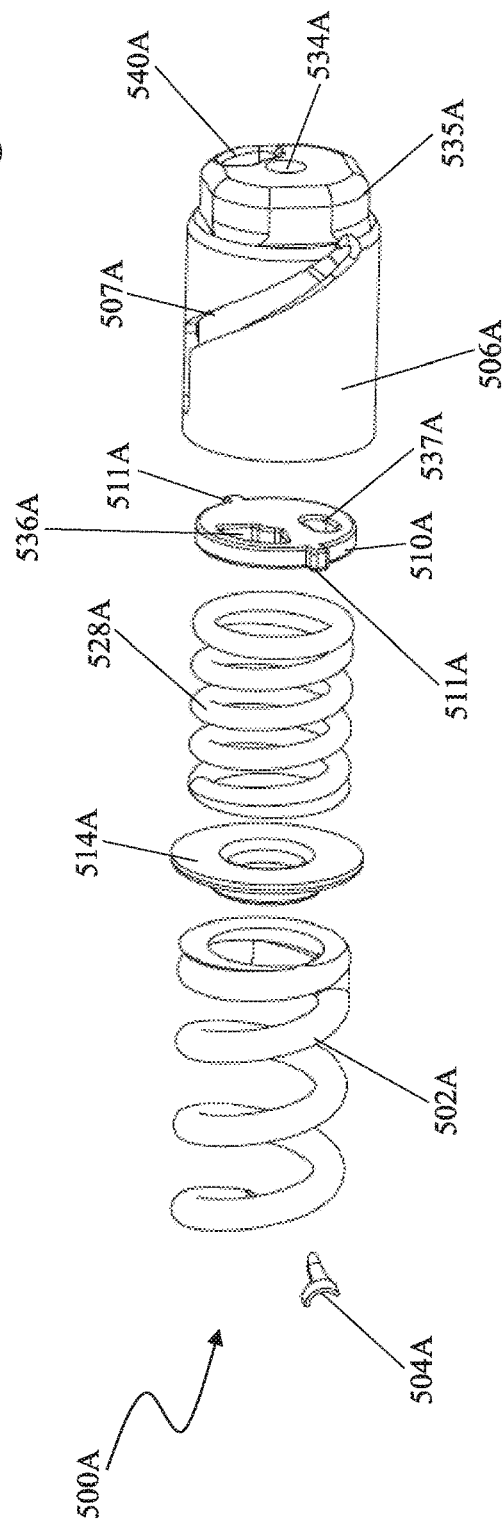
Fig. 16A
Fig. 16B
Fig. 16C

HELICAL CARDIAC ANCHORS FOR MINIMALLY INVASIVE HEART VALVE REPAIR

RELATED APPLICATIONS

The present application claims the benefit of U.S. Provisional Application No. 62/962,054 filed Jan. 16, 2020 and U.S. Provisional Application No. 62/987,140 filed Mar. 9, 2020, both of which are hereby incorporated herein by reference in their entireties.

TECHNICAL FIELD

The present invention relates to minimally invasive delivery of a suture into the heart. More particularly, the disclosed embodiments relate to inserting and anchoring one or more sutures as artificial chordae tendineae for a flailing or prolapsing leaflet in a beating heart.

BACKGROUND

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae results in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle.

This technique for implantation of artificial chordae was traditionally done by an open heart operation generally carried out through a median sternotomy and requiring cardiopulmonary bypass with aortic cross-clamp and cardioplegic arrest of the heart. Using such open heart techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of an artificial chordae through the atriotomy for attachment within the heart. However, these invasive open heart procedures in which the heart is stopped beating produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of such open heart techniques.

Techniques for minimally invasive thoracoscopic repair of heart valves while the heart is still beating have also been developed. U.S. Pat. No. 8,465,500 to Speziali, which is incorporated by reference herein, discloses a thoracoscopic heart valve repair method and apparatus. Instead of requiring open heart surgery on a stopped heart, the thoracoscopic heart valve repair methods and apparatus taught by Speziali utilize fiber optic technology in conjunction with transesophageal echocardiography (TEE) as a visualization technique during a minimally invasive surgical procedure that can be utilized on a beating heart. More recent versions of these techniques are disclosed in U.S. Pat. Nos. 8,758,393 and 9,192,374 to Zentgraf, which are also incorporated by reference herein and disclose an integrated device that can enter the heart chamber, navigate to the leaflet, capture the leaflet, confirm proper capture, and deliver a suture as part of a mitral valve regurgitation (MR) repair. In some procedures, these minimally invasive repairs are generally performed through a small, between the ribs access point followed by a puncture into the ventricle through the apex of the heart. Although far less invasive and risky for the patient than an open heart procedure, these procedures still require significant recovery time and pain.

Some systems have therefore been proposed that utilize a catheter routed through the patient's vasculature to enter the heart and attach a suture to a heart valve leaflet as an artificial chordae. While generally less invasive than the approaches discussed above, transcatheter heart valve repair can provide additional challenges. For example, with all artificial chordae replacement procedures, in addition to inserting a suture through a leaflet, the suture must also be anchored at a second location, such as at a papillary muscle in the heart, with a suture length, and tension and positioning of the suture should be adjustable to enable the valve to function naturally. If the suture is too short and/or has too much tension, the valve leaflets may not properly close. Conversely, if the suture is too long and/or does not have enough tension, the valve leaflets may still be subject to prolapse. Proper and secure anchoring of the suture at the second position away from the leaflet is therefore a critical aspect of any heart valve repair procedure for inserting an artificial chordae. In the case of transcatheter procedures, such anchoring can be difficult because it can be difficult for the flexible catheter required for routing through the patient's vasculature to apply sufficient force to stably insert traditional suture anchors into the heart wall, e.g., the myocardium.

SUMMARY

Disclosed herein are various embodiments of cardiac anchors configured to be inserted into a heart wall of a patient to anchor a suture as an artificial chordae under an appropriate tension for proper valve function. Such cardiac anchors are particularly suitable for use in intravascular, transcatheter procedures.

In an embodiment, an anchor assembly is configured to implant a cardiac anchor into a heart wall of a patient to anchor a suture configured to extend from a valve leaflet of the heart as an artificial chordae. The anchor assembly can include an anchor hub defining an open interior and a helical coil extending distally from the anchor hub and having a sharpened tip configured to embed the helical coil into the heart wall upon rotation of the helical coil. A spring can be disposed within the open interior of the anchor hub. Compressing the spring distally can create an open space within the open interior of the anchor hub for a suture extending through the anchor hub to slide freely and releasing compression on the spring can cause the spring to expand in a proximal direction to clamp the suture within the open interior of the anchor hub.

In an embodiment, an anchor assembly is configured to implant a cardiac anchor into a heart wall of a patient to anchor a suture configured to extend from a valve leaflet of the heart as an artificial chordae. Anchor assembly can include an anchor base and a helical coil extending distally from the anchor base and having a sharpened tip configured to embed the helical coil into the heart wall upon rotation of the helical coil. In some embodiments, a stabilizing needle can extend longitudinally through and distally beyond the helical coil and have a sharpened tip configured to pierce the heart wall to stabilize the helical coil for insertion of the helical coil into the heart wall. A suture clamp can be configured to be rotated to clamp a suture under tension between the suture clamp and the anchor base. In embodiments, the suture clamp can include an anchor washer movable along a body of the anchor base and configured to have a suture inserted through a space between the anchor washer and the body of the anchor base and an anchor clamp nut threadedly attached to the anchor base. Rotation of the anchor clamp nut in a first direction can move the anchor clamp nut distally to clamp a suture inserted through the space between the anchor washer and the body of the anchor base between the anchor base and the anchor washer and between the anchor clamp nut and the anchor washer.

In an embodiment, an anchor assembly is configured to implant a cardiac anchor into a heart wall of a patient to anchor a suture configured to extend from a valve leaflet of the heart as an artificial chordae. The anchor assembly can include a suture anchor including an anchor hub, a helical coil extending distally from the anchor hub and having a sharpened tip configured to embed the helical coil into the heart wall upon rotation of the helical coil, and a suture lock threadedly attached to a proximal end of the anchor hub. The assembly can include an anchor hub driver having a drive end configured to mate with the anchor hub and an anchor hub driver tube configured to be rotated to rotate the suture anchor for insertion into the heart wall. The assembly can further include a suture lock driver having a drive end configured to mate with the suture lock and a suture lock driver tube, such that rotation of the suture lock driver in a first direction moves the suture lock distally to clamp a suture between the suture lock and the anchor hub. In embodiments, the suture lock can include a suture locking wedge including a threaded distal portion configured to interface with a threaded distal portion of the anchor hub and a tapered clamping surface configured to clamp the suture between a chamfered interior surface of the anchor hub and the tapered clamping surface of the suture locking wedge.

In an embodiment, an anchor assembly is configured to implant a cardiac anchor into a heart wall of a patient to anchor a suture configured to extend from a valve leaflet of the heart as an artificial chordae. The anchor assembly can include a suture anchor including an anchor hub, a helical coil extending distally from the anchor hub and having a sharpened tip configured to embed the helical coil into the heart wall upon rotation of the helical coil. In some embodiments, a stabilizing needle extending longitudinally through and distally beyond the helical coil has a sharpened tip configured to pierce the heart wall to stabilize the helical coil for insertion of the helical coil into the heart wall. An anchor delivery assembly can include an anchor driver configured to mate with the anchor hub to rotate the suture anchor for insertion into the heart wall. A suture lock delivery system can include a lock carrier configured to mate with the anchor hub and to carry a suture lock and a pusher movable with respect to the lock carrier. The pusher can be configured to push the suture lock off of the lock carrier and onto the anchor hub to clamp a suture between the suture lock and the anchor hub. In embodiments, the suture lock is configured as a spring.

In an embodiment, an anchor assembly is configured to implant a cardiac anchor into a heart wall of a patient to anchor a suture configured to extend from a valve leaflet of the heart as an artificial chordae. The anchor assembly can include an anchor hub defining an open interior and a proximal end cap covering the open interior. A helical coil can extend distally from the anchor base and have a sharpened tip configured to embed the helical coil into the heart wall upon rotation of the helical coil. In some embodiments, a stabilizing needle can extend longitudinally through and distally beyond the anchor hub and the helical coil. The stabilizing needle can have a sharpened tip configured to pierce the heart wall to stabilize the helical coil for insertion of the helical coil into the heart wall and a threaded proximal portion rotatingly attached to the end cap of the anchor hub. A piston chamber can be disposed within the open interior of the anchor hub, with the piston chamber and the end cap each having one or more openings enabling one or more sutures to pass through the piston chamber and the end cap. A spring can be disposed within the piston chamber between a proximal end of the piston chamber and a distal end of the anchor hub such that the spring biases the piston chamber proximally towards the end cap. Rotation of the stabilizing needle in a first direction can move the piston chamber distally to compress the spring to provide space between the piston chamber and the end cap for a suture to move freely and rotation of the stabilizing needle in a second direction can move the piston chamber proximally to clamp the suture between the piston chamber and the end cap.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 3A-3L depict the various components of the anchor system of FIGS. 2A-2F.

FIGS. 6A-6J depict the various components of the anchor system of FIGS. 5A-5C.

FIGS. 7A-7D schematically depict a procedure for anchoring an artificial chordae according to an embodiment.

FIGS. 9A-9H depict the various components of the anchor system of FIGS. 8A-8G.

FIGS. 10A-10J schematically depict a procedure for anchoring an artificial chordae according to an embodiment.

FIGS. 12A-12F depict the various components of the anchor system of FIGS. 11A-11C.

FIGS. 13A-13B depict various view of an anchor system for an artificial chordae according to an embodiment.

FIGS. 15A-15H schematically depict a procedure for anchoring an artificial chordae according to an embodiment.

FIGS. 16A-16E depict various views of an anchor system for an artificial chordae according to an embodiment.

Figure 1:
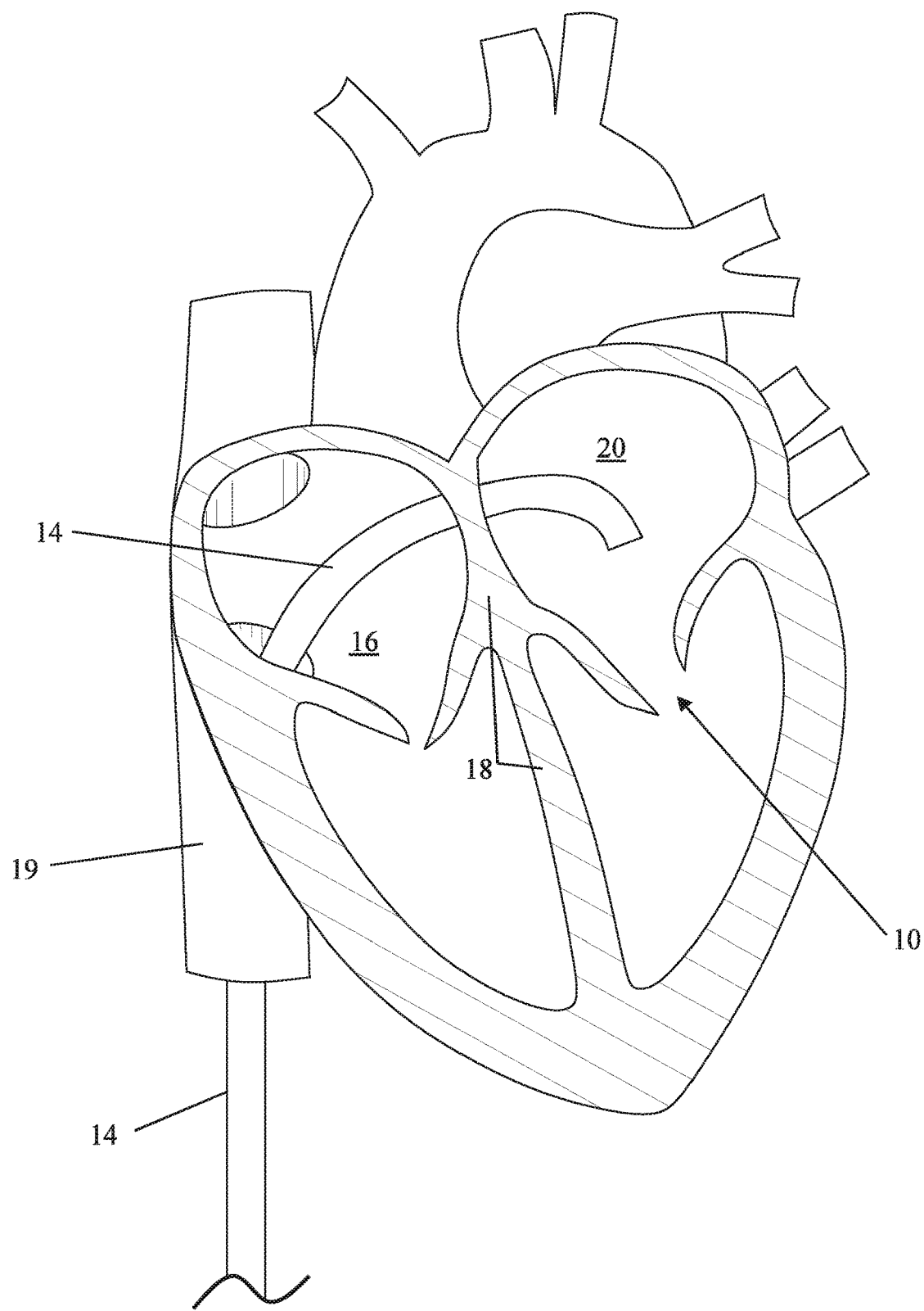
FIG. 1 is a schematic representation of a method for inserting a leaflet capture catheter into a beating heart of a patient according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The present disclosure is generally directed to inserting and anchoring one or more sutures as artificial chordae into one or more heart valve leaflets through an intravascular, transcatheter approach. A heart valve leaflet may be captured and a suture inserted through the leaflet in any manner known in the art. Examples of such leaflet capture catheters are disclosed in copending U.S. Patent Publication No. 2019/0290260 and U.S. patent application Ser. No. 16/564,887, each of which is hereby incorporated by reference herein. Other transcatheter procedures for inserting an artificial chordae are disclosed in U.S. Patent Publication No. 2016/0143737 and U.S. patent application Ser. No. 16/745,074, each of which is hereby incorporated by reference herein.

In each of the below described embodiments, access into the heart to the valve being repaired can be gained through an intravascular, transcatheter approach. If the valve being repaired is the mitral valve, the valve may further be accessed transseptally. FIG. 1 depicts a schematic representation of an embodiment of an access approach for a heart valve repair system accessing the mitral valve 10. FIG. 1 depicts a guide catheter 14 accessing the interior of the heart via the femoral vein. In some embodiments, such a system can further include an outer guide catheter and an inner guide catheter. In such embodiments, the outer guide catheter can be inserted into the femoral vein at the patient's groin and advanced through the femoral vein into the inferior vena cava 19 and then into the right atrium 16. In various embodiments, the outer guide catheter can be steerable in a single plane and can have an outer diameter of about or less than about 30 French, such as, for example 24 French. The septum 18 can then be punctured using an appropriate puncture tool and the outer guide catheter advanced into the septum 18 or through the septum 18 into the left atrium 20. The inner guide catheter can then be axially advanced through the outer guide catheter into the left atrium 20. In some embodiments, the inner guide catheter can have two plans of steerability and can be maneuvered along with and/or beyond the outer guide catheter to establish a stable position superior to the mitral valve 10 and to provide a desired trajectory for operation of a leaflet capture catheter to repair the valve. In other embodiments, anchors as described herein may be implanted through other intravascular approaches as well as non-intravascular approaches.

FIGS. 2A-2F depict various views of an anchor assembly 100 for anchoring a suture as an artificial chordae in a heart wall of a patient and FIGS. 3A-3L depict the various components thereof. Anchor assembly 100 includes an anchor coil 102 that embeds the anchor assembly 100 into heart tissue and, in some embodiments, a central stabilizing needle 104 extending longitudinally through the coil 102 to stabilize the anchor assembly 100 while the coil 102 is driven into the tissue. An anchor base 106 can connected to the anchor coil 102 and the stabilizing needle 104. Anchor assembly 100 can further include a plurality of suture clamping components, including an anchor washer 108, an anchor clamp ring 110, an anchor clamp nut 112, an anchor clamp nut cap 114, an anchor clamp nut driver 116 and an anchor cap 118, which will be described in more detail below. An anchor sheath 124 is used to deliver and cover the anchor assembly 100 before it is deployed and the components of the anchor assembly 100 are actuated with an anchor tether 120 and an anchor driver tube 122 as will also be described in more detail below.

Referring to FIG. 3A, stabilizing needle 104 can include a sharp tip 126 capable of piercing the tissue of the heart wall. By piercing the heart wall with stabilizing needle 104, the anchor assembly is stably held in position to enable the anchor coil 102 to be embedded into the heart wall to anchor the assembly by rotating anchor assembly 100. A proximal threaded end 128 of the stabilizing needle 104 can be configured to be to be connected to anchor base 106. The proximal threaded end 128 can also be drilled out to provide a hollow interior configured to enable the tether 120 to be attached thereto such as, for example, by laser welding. In other embodiments, anchor assembly 100 can be provided without stabilizing needle 104. In some such embodiments, a stabilizing needle can alternatively be provided with an anchor delivery catheter, as described below with respect to FIGS. 15A-15H.

Anchor coil 102 includes a distal tip 130 for piercing the tissue of the heart wall. In embodiments, the anchor coil 102 is configured to be rotated clockwise to screw into the tissue. Anchor coil 102 can further be provided with anti-backout features, such as one or more barbs, that prevent rotation of anchor coil 102 due to natural heart rhythms from backing the coil out of the tissue. The anchor coil 102 can be connected to the anchor base 106 such as, for example, by laser welding.

The inside diameter of the anchor base 106 can be drilled out to create a hollow passage 132 to receive the proximal portion of the stabilizing needle, including an internally and externally threaded portion 134 that internally interfaces with the proximal threaded end 128 of the stabilizing needle 104. A chamfer surface 136 of anchor base 106 that is longitudinally angled with respect to the assembly functions as one of the clamping surfaces for clamping the suture.

The anchor washer 108 is not threaded or welded to any component. The washer 108 can float rotationally and axially unconstrained on the shaft 138 of the anchor base. Anchor washer 108 functions to clamp the suture between the anchor base 106 and the anchor clamp ring 110. The anchor clamp ring 110 is similarly not threaded or welded onto any component and can axially float on the anchor base shaft 138 but is rotationally constrained on the anchor base 106. Anchor clamp ring 110 is prevented from rotating because it interfaces directly with the suture (which does not rotate) but is pushed down by the anchor clamp nut 112 (which rotates while threading down on the anchor base). In embodiments, anchor clamp ring 110 can be prevented from rotating by cutting off the outer threads on two sides of the anchor base 106. The anchor clamp nut 112 includes internal threading 140 to rotationally attach the anchor clamp nut 112 to the external threading of threaded portion 134 of anchor base 106. As the anchor clamp nut 112 is rotated counter-clockwise, it moves down along the threading of threaded portion 134 to clamp the suture. The anchor clamp nut cap 114 interfaces with an open proximal end 142 of the anchor clamp nut 112 and can be attached, e.g., by laser welding, after the anchor clamp nut 112 is threaded on to the anchor base 106 to lock the anchor clamp nut 112 on and prevent removal of the anchor clamp nut 112 from the anchor base 106. After the anchor clamp nut cap 114 is attached to the anchor clamp nut 112, the anchor clamp driver 116 can be attached such as by laser welding onto the anchor clamp nut cap 114 with a drive end 146 (e.g., a hex drive) of the anchor clamp driver 116 interfacing with a correspondingly shaped aperture 144 in the anchor clamp nut cap 114. Rotation of the anchor clamp driver 116 therefore rotates the anchor clamp nut 112. The anchor cap 118 can be attached to the anchor base 106, such as by laser welding, after the anchor washer 108, anchor clamp ring 110 and anchor clamp nut 112 have been assembled with anchor base 106, which locks anchor clamp nut 112 onto anchor base 106 to eliminate the risk of accidentally threading the anchor clamp nut 112 back off of the anchor base 106.

The anchor tether 120 can be a flexible, generally cylindrical component that can travel through the anchor driver tube 122 and the anchor base 106 and be attached to the stabilizing needle 104 by, for example, laser welding. In one embodiment, tether 120 is a Nitinol wire. The anchor 100 is driven into tissue by twisting the anchor tether 120 clockwise, with the torque being transferred from the anchor tether 120 to the stabilizing needle 104 and the anchor base 106 to which the anchor coil 102 is attached, thus causing rotation of the anchor coil 102 to embed the coil into tissue. In embodiments that do not utilize a stabilizing needle 104 as part of the anchor assembly, the anchor tether 120 can attach to and directly rotate the anchor base 106.

Figure 2A:
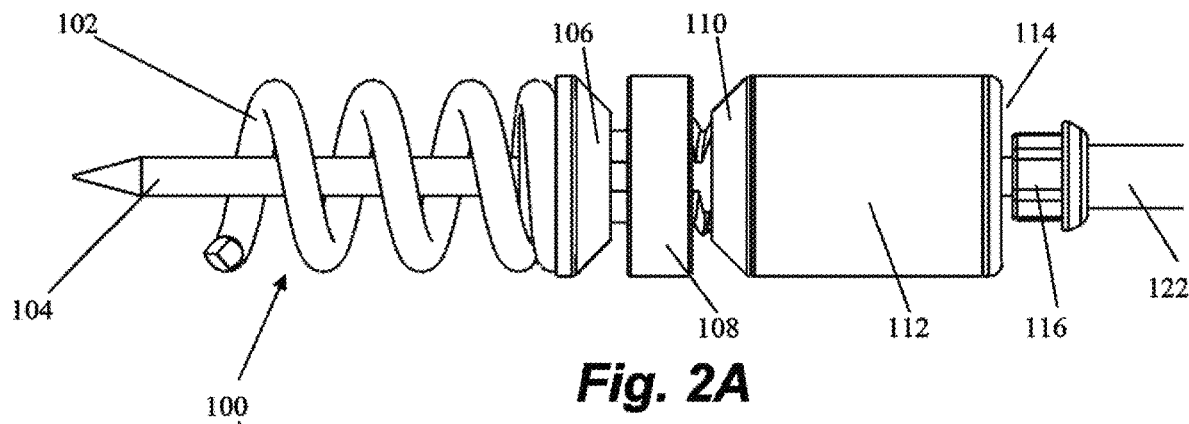
FIGS. 2A-2F depict various views of an anchor system for an artificial chordae according to an embodiment.
Figure 2B:
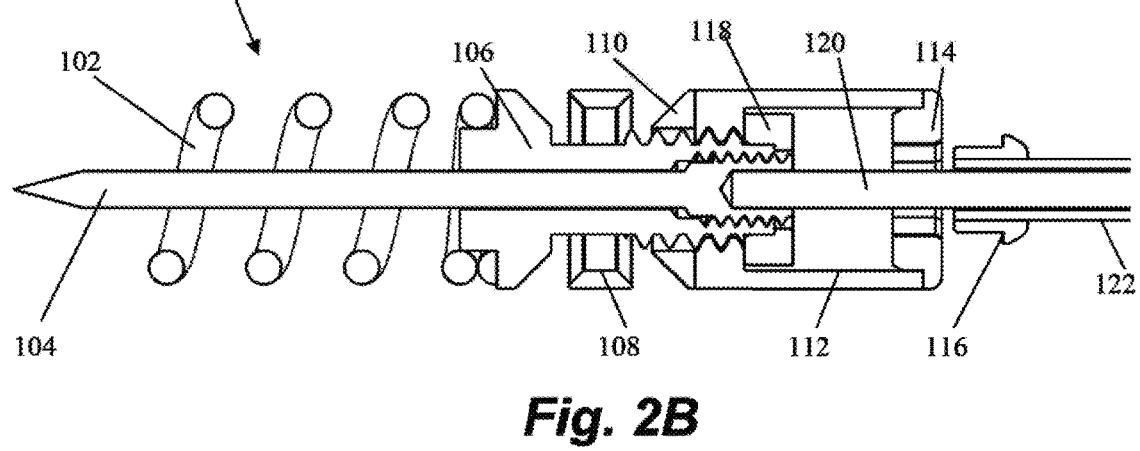
Figure 2C:
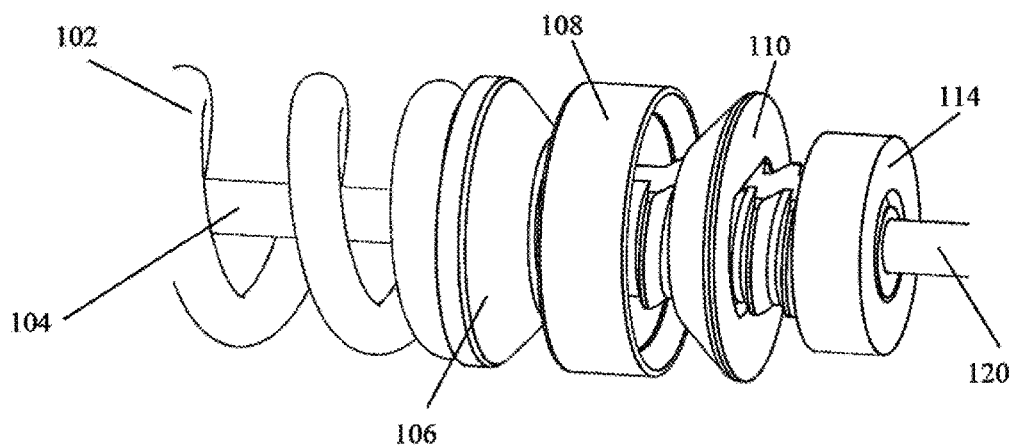
Figure 2D:
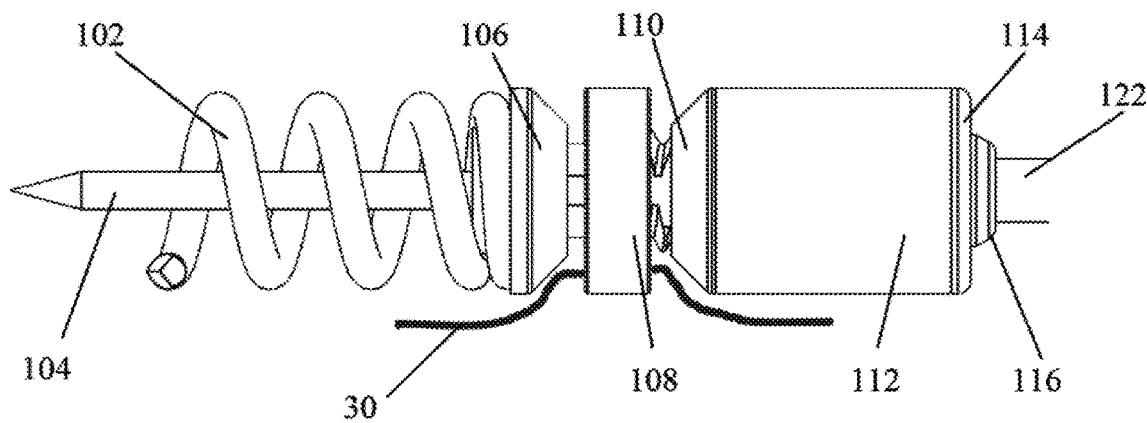
Figure 2E:
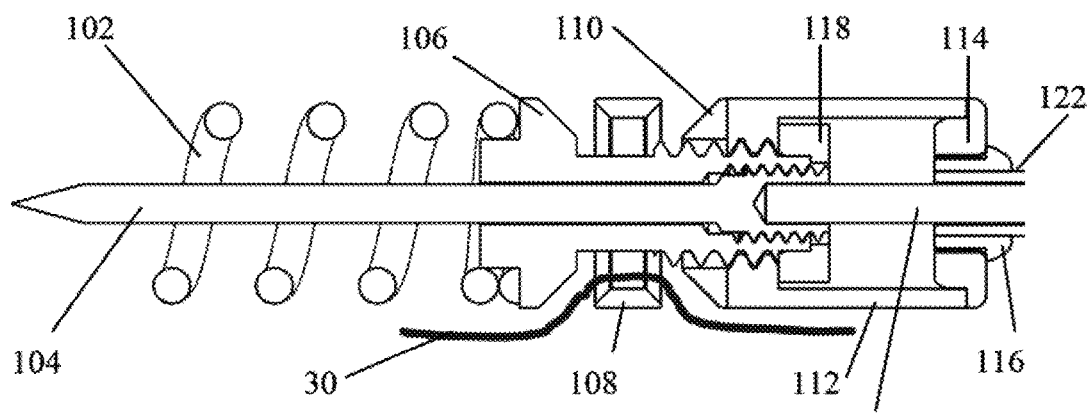
Figure 2F:
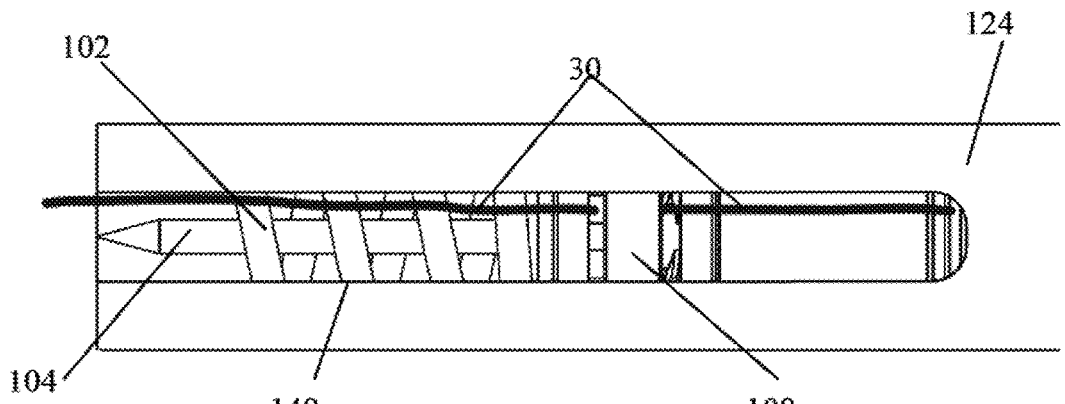

The anchor driver tube 122 is attached to the anchor clamp nut cap 114 such that rotation of the anchor driver tube 122 causes rotation of the anchor clamp nut 112 to move the anchor clamp nut 112 along the threaded portion 134 of the anchor base 106 to clamp the suture between the anchor base 106, anchor washer 108 and anchor clamp ring 110. As can be seen in FIGS. 2D-2F, the suture 30 is threaded through the anchor washer 108 and is clamped therein between chamfer surface 136 of anchor base 106 and anchor clamp ring 110. The anchor sheath 124 covers the anchor coil 102 before the anchor 100 is deployed. The anchor sheath 124 can include a slit 148 on one side of anchor sheath 124 that enables the suture to access the anchor locking components and then enter the anchor sheath proximal to the anchor. Following seating of the anchor in the heart wall, the anchor driver tube 122 and anchor cap 118 and then the tether 120 and stabilizing needle 104 can be withdrawn by twisting the tether counter-clockwise.

Referring to FIGS. 2D-2F, the routing of suture 30 through anchor assembly 100 is depicted. After suture 30 is inserted into a valve leaflet, suture 30 is threaded through anchor washer 108 outside of the body. The anchor 100 is inserted into anchor sheath 124 and delivered into the heart such that the suture 30 extends through anchor sheath 124 back out of the body to enable suture 30 tension to be adjusted from outside the body. As the anchor clamp nut 112 is tightened, the suture is clamped between the chamfer surface 136 of anchor base and the distal side of anchor washer 108 and between the anchor clamp ring 110 and the proximal side of anchor washer 108 to securely hold the suture 30 at a desired tension. Although depicted as a single suture 30, it should be understood that a plurality of sutures could be locked in this manner.

Figure 4B:
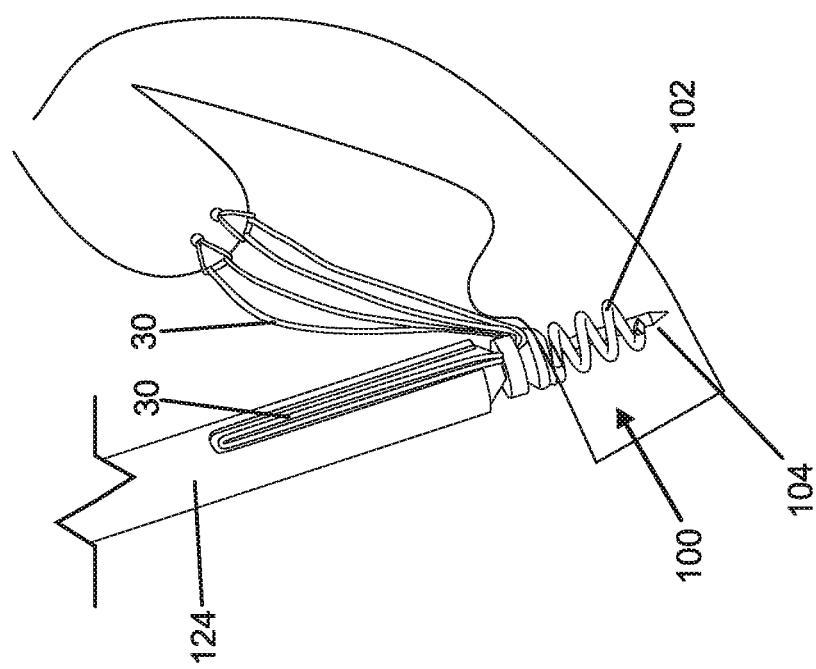
FIGS. 4A-4C schematically depict a procedure for anchoring an artificial chordae according to an embodiment.
Figure 4A:
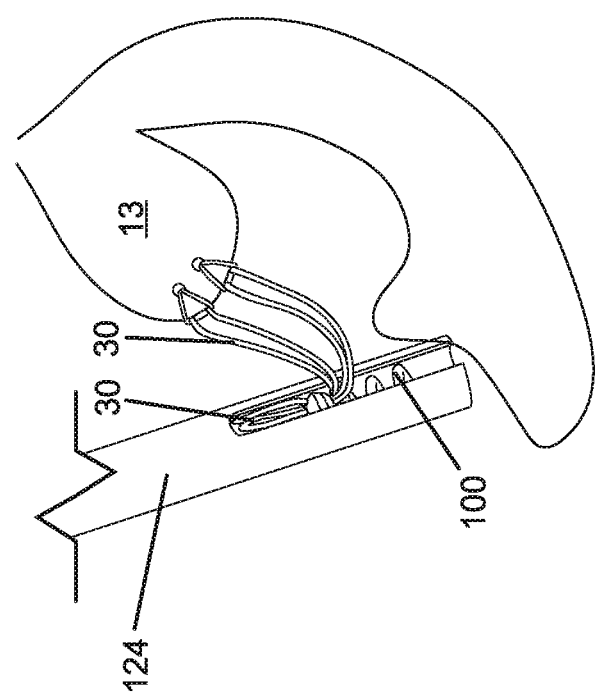
Figure 4C:
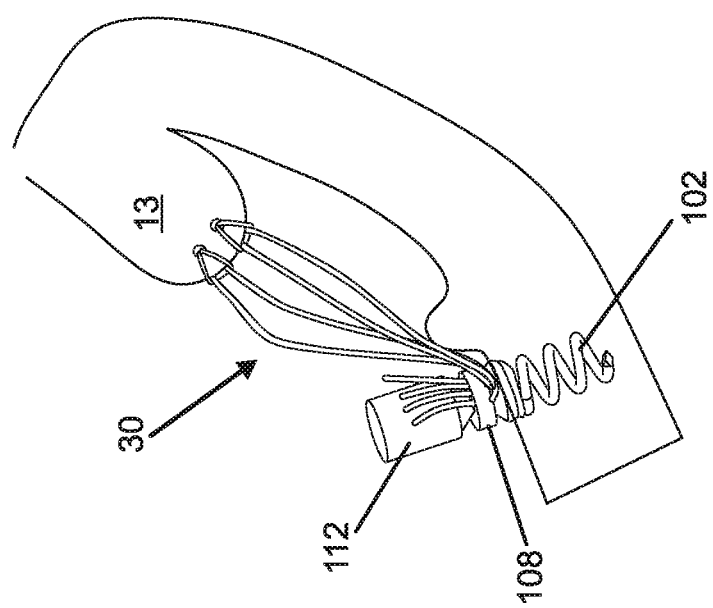

FIGS. 4A-4C depict schematic representations of various steps of a method of repairing a heart valve according to another embodiment that utilizes anchor system 100. After the sutures 30 are inserted into the leaflet 13, they can be threaded through anchor washer 108 of anchor 100 outside of the body. The anchor 100 can then be inserted into anchor delivery catheter or sheath 124 and positioned adjacent the heart wall. The stabilizing needle 104 first pierces the tissue to stabilize the anchor while the coil 102 is driven into the tissue by rotating the anchor 100 as described above. After the anchor 600 has been inserted, the sutures can be tensioned and then locked by rotating an anchor clamp nut 112 to clamp down on the sutures 30. The stabilizing needle 104 can then be removed and the sutures ends severed as depicted in FIG. 4C.

Figure 5A:
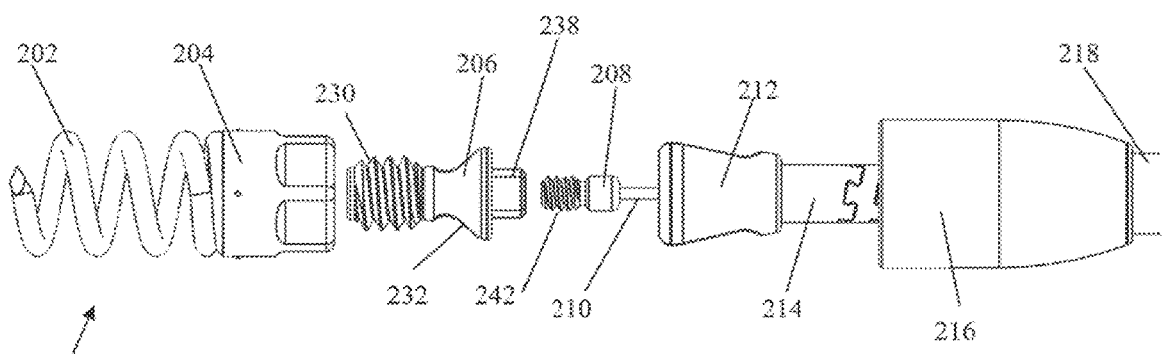
FIGS. 5A-5C depict various views of an anchor system for an artificial chordae according to an embodiment.
Figure 5B:
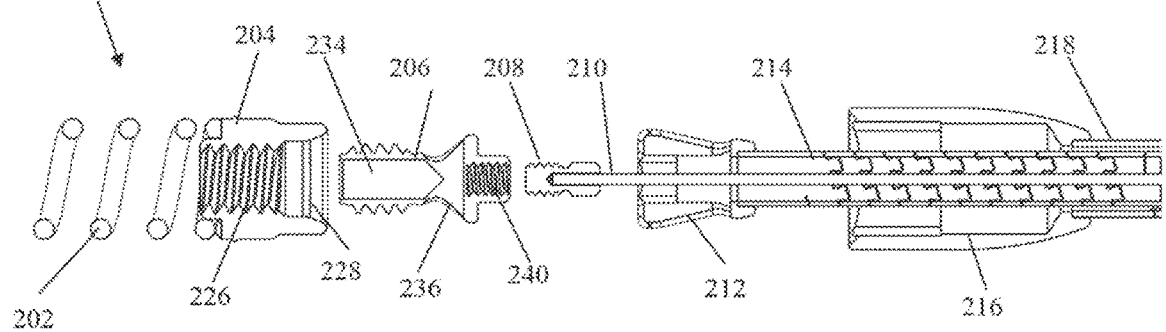
Figure 5C:
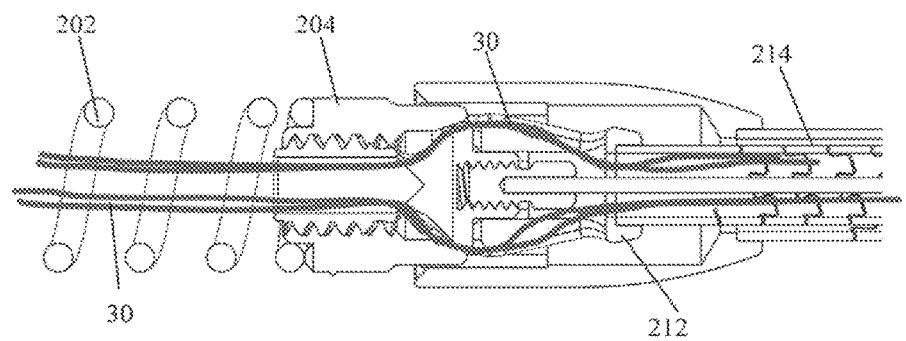
Figure 6H:
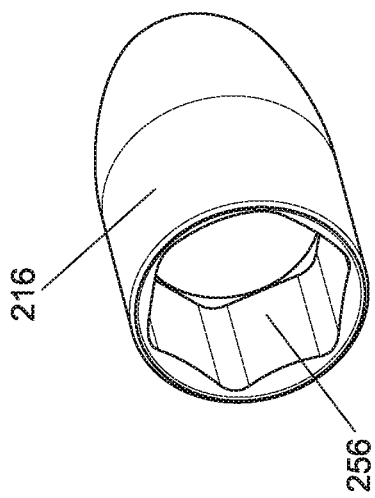
Figure 6J:
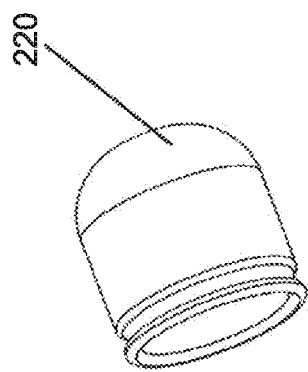
Figure 6G:
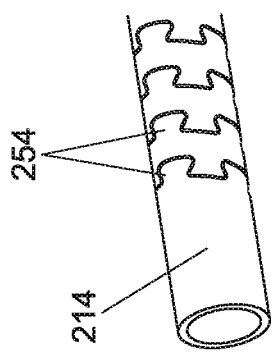
Figure 6I:
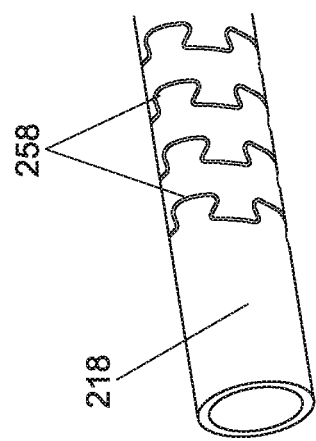

FIGS. 5A-5C depict various views of an anchor assembly 200 for anchoring a suture as an artificial chordae in a heart wall of a patient and FIGS. 6A-6J depict the various components thereof. Anchor assembly 200 includes an anchor coil 202 configured to embed the anchor into the tissue of the heart wall and a suture locking system that locks one or more sutures at a set tension for proper valve function.

Anchor coil 202 includes a sharpened distal tip 222 configured to pierce the tissue and is configured to be embedded into the heart wall by clockwise rotation and can be used with anti-backout features, such as one or more barbs. The anchor coil 202 is connected to the anchor hub 204, such as, for example, by laser welding. The anchor hub 204 includes a proximal drive end 224 such, as for, example a hex drive configured to interface with an anchor hub driver 216 to enable rotation of the hub 204 and coil 202. As can be seen in FIG. 5B, the anchor hub 204 can further include an interior threaded portion 226 at a distal portion of the anchor hub 204 and an interior chamfered chamber 228 at a proximal portion thereof.

Suture locking wedge 206 includes a distal threaded portion 230 configured to interface with the interior threaded portion 226 of anchor hub 204. A tapered outer surface 232 of suture locking wedge 206 interfaces with the interior chamfered chamber 228 of the anchor hub to lock the suture between the two surfaces. A hollow longitudinal chamber 234 extends from distal threaded portion 230 of suture locking wedge 206 and is in communication with a cross aperture 236 through tapered outer surface 232. As can be seen in FIG. 5C, this enables one or more sutures 30 to extend proximally up through anchor coil 202, through the hollow chamber 234 and out of the cross apertures 236 of anchor base and back proximally through the device. At the distal end, suture locking wedge 206 can further include a drive end 238, such as a hex drive, to interface with a suture lock driver 212. The center of the drive end 238 can include internal threading 240 to interface with a threaded distal end 242 of tether crimp 208. Proximal portion 244 of tether crimp includes a drilled out hollow chamber that is crimped onto the tether 210. In an embodiment, tether 210 is a Nitinol wire that is, for example, 0.015 inches in diameter. The tether crimp 208 and tether 210 are fastened to the suture locking wedge 206 to ensure that the anchor is not prematurely released.

Suture lock driver 212 has a drive end 248 with an internal geometry, e.g., hex, matching that of the drive end 238 of the suture locking wedge 206. In embodiments, the two components interface with a slip fit. Suture lock driver 212 further includes two open sides 250 that enable sutures to enter suture lock driver 212 and exit out of a proximal aperture 252. Suture lock driver 212 is connected to suture lock driver tube 214 such as, for example, by laser welding. Suture lock driver 212 can be rotated clockwise via suture lock driver tube 214 to move the suture locking wedge 206 distally to clamp the suture 30 between the suture locking wedge 206 and the anchor hub 204. In some embodiments, suture lock driver tube 214 can be laser cut at lines 254 to provided added flexibility for maneuvering the device through the vasculature and to reduce torque buildup on the distal portion of the system.

Anchor hub driver 216 includes a drive end 256 with an internal geometry, e.g., hex, matching that of the drive end 224 of the anchor hub 204. Rotating of the anchor hub driver 216 via the anchor hub driver tube 218 in a clockwise direction rotates the anchor hub 204 and the anchor coil 202 to embed the anchor coil 202 into the heart tissue. Applying a counter-force on the anchor hub 204 with the anchor hub driver 216 can also provide a counter-torque when applying a final torque to the suture locking wedge 206 with the suture lock driver 212 to lock the sutures within the anchor hub 204 with the suture locking wedge 206. In embodiments, the anchor hub driver tube 218 can also be connected to the anchor hub driver 216 by laser welding and can be laser cut along lines 258 to provide added flexibility. A covering dome 220 can be provided to mate with the anchor hub 204 and cover the sutures once the sutures have been tensioned, locked, and cut. In embodiments, the covering dome 220 can be covered with ePTFE to encourage tissue ingrowth and discourage thrombosis.

Referring to FIG. 5C, the routing of sutures 30 through anchor system is depicted (in which a pair of sutures is depicted, by fewer or greater sutures could be employed). After each suture 30 is deployed into a leaflet, the ends of the suture 30 are threaded through anchor system 200 such that they extend back through anchor coil 202 and anchor hub 204, into the distal chamber 234 and out of the cross aperture 236 of the suture locking wedge 206, and back through suture lock driver 212, suture lock drive tube 214 and anchor hub drive tube 218 to be able to be tensioned from outside of the body. When the suture locking wedge 206 is advanced distally, the sutures 30 are clamped between the tapered surface 232 of the suture locking wedge 206 and the chamfered chamber 228 of the anchor hub 204 to lock the suture at a desired tension.

Figure 7C:
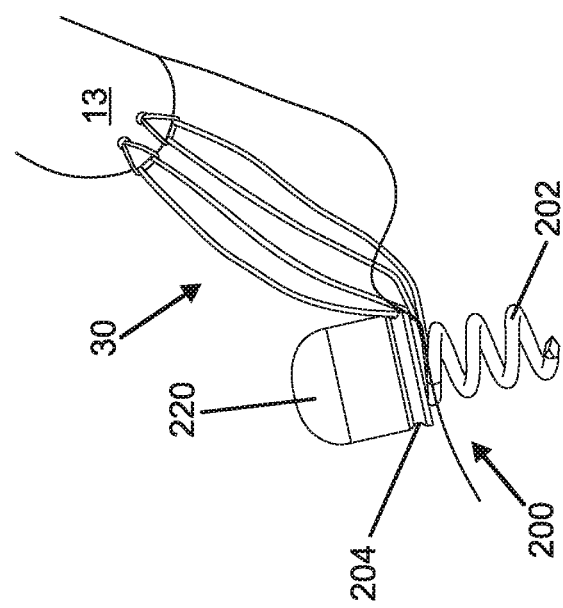
Figure 7D:
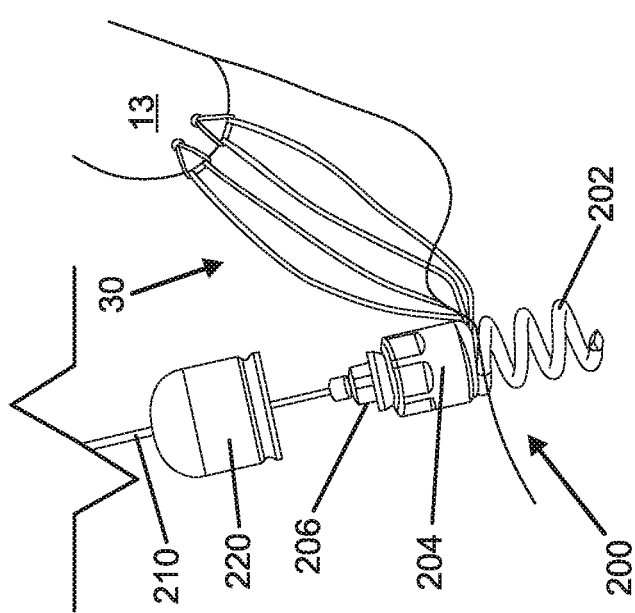

FIGS. 7A-7D depict schematic representations of various steps of a method of repairing a heart valve according to another embodiment that also utilizes anchor system 200. After sutures 30 are inserted into the leaflet 13, the sutures 30 can be threaded through the anchor coil 202 and anchor body 704 of anchor exterior to the body. Anchor catheter 223 can then be used to deliver the anchor system 200 to the heart wall. The anchor hub driver 216 can then be used with the anchor hub driver tube 218 to rotate the anchor to 200 embed the coil 202 into the heart wall. As the coil 202 advances, the suture 30 slides through the coil and to the anchor hub 204 once the coil is full inserted into the tissue. The anchor hub driver 216 and anchor hub driver tube 218 can then be withdrawn above as depicted in FIG. 7B. The sutures can then be preliminarily tensioned and locked by rotating suture lock driver 212 clockwise with suture lock driver tube 214 to advance suture locking wedge 206 (see FIG. 7C) to clamp the suture in anchor hub 204 as described above. In embodiments, if the tension is not appropriate the suture locking wedge 206 can be unlocked and the sutures re-tensioned. Once desired tension is achieved and the suture locking wedge 206 is preliminarily locked, the anchor hub driver 216 can be brought back down to apply a counter torque while applying a strong torque to the suture locking wedge 206 with the suture lock driver 212 for final locking. The suture lock driver 212 and anchor hub driver 216 can then be withdrawn, leaving tether 210 extending from the anchor 200 back out of the heart. The free ends of the suture 30 can then be severed and a suture cover 220 can be advanced along the tether 210 to be seated on the anchor hub 204 to cover sutures 30. The tether 210 can then be severed and withdrawn from the body, leaving the anchor 200 in place.

FIGS. 8A-8I depict various views of an anchor assembly for anchoring a suture as an artificial chordae in a heart wall of a patient and FIGS. 9A-9H depict the various components thereof. Anchor assembly includes an anchor delivery assembly 301 and suture lock assembly 303. Once the anchor delivery assembly 301 is used to embed the anchor in the heart wall, the anchor delivery assembly 301 is withdrawn and the suture lock assembly 303 is used to deliver and lock the sutures to the anchor.

Anchor delivery assembly 301 includes an anchor coil 302 with a central stabilization needle 304 in some embodiments extending longitudinally through the anchor coil 302. Stabilization needle 304 provides stability against the ventricular wall during anchor deployment and also provides the attachment to the tether 310 that extends out of the body and is used to rotate the anchor assembly. Needle 304 includes a sharpened distal tip 314 configured to penetrate the heart tissue and a threaded portion 316 that releasably secures the needle 304 within internal threads in the anchor hub 306. Anchor coil 302 connects to anchor hub 306, such as, for example, by welding, and can include an anti-backout feature. Anti-backout feature can be configured as a barb 308 positioned around coil 302 that keeps the coil 302 from rotating back out of the tissue due to the natural rhythm of the heart. In embodiments, barb 308 can be welded onto the coil 302. Coil 302 includes a sharpened distal tip 312 configured to penetrate the tissue in the heart. In other embodiments, anchor assembly can be provided without stabilizing needle 304. In some such embodiments, a stabilizing needle can alternatively be provided with an anchor delivery catheter, as described below with respect to FIGS. 15A-15H.

Figure 8A:
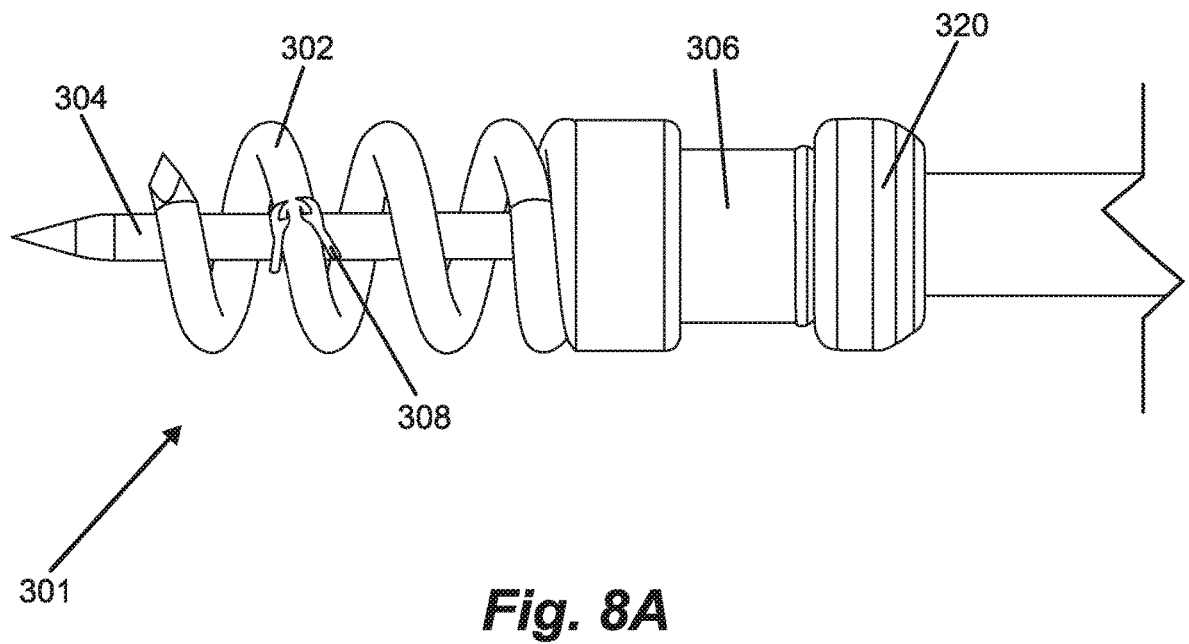
FIGS. 8A-8I depict various views of an anchor system for an artificial chordae according to an embodiment.
Figure 8B:
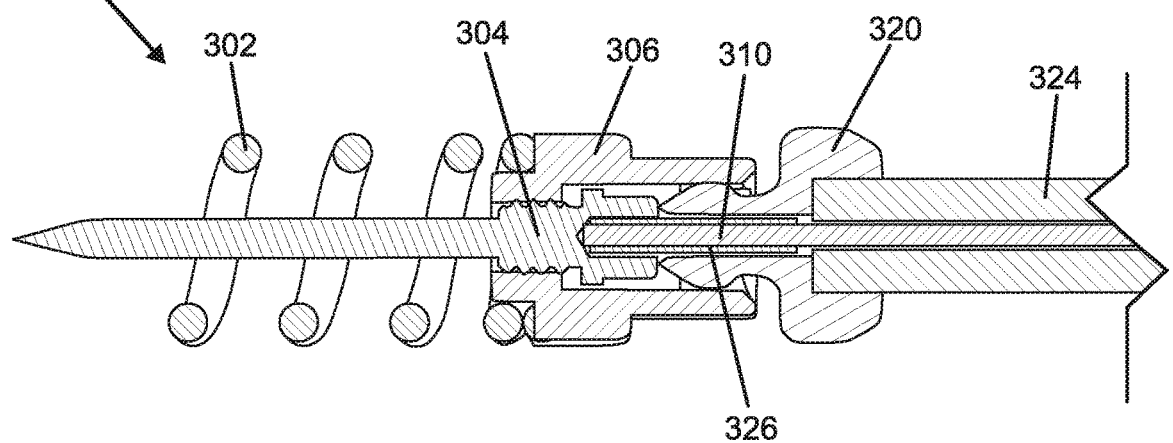
Figure 8C:
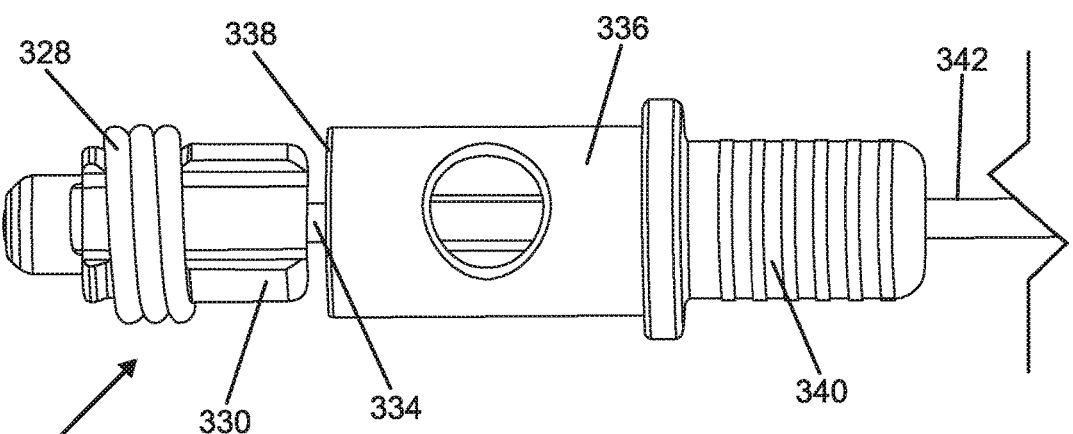
Figure 8D:
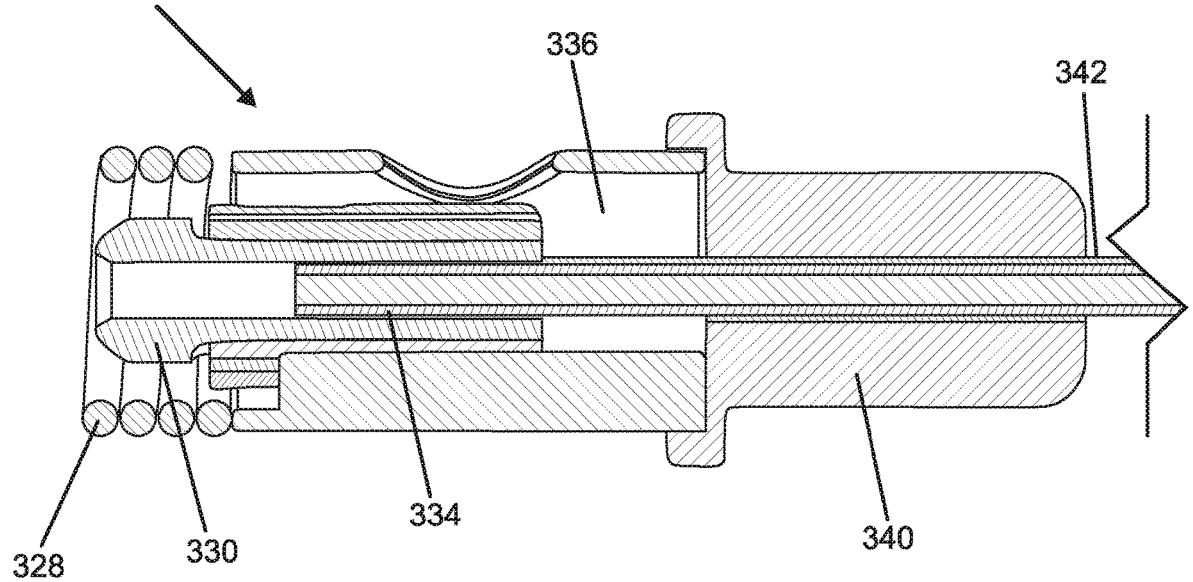
Figure 8E:
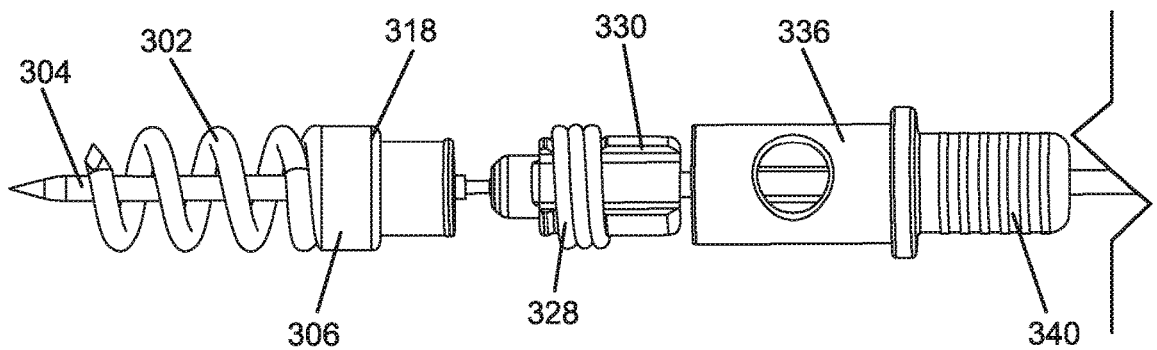
Figure 8F:
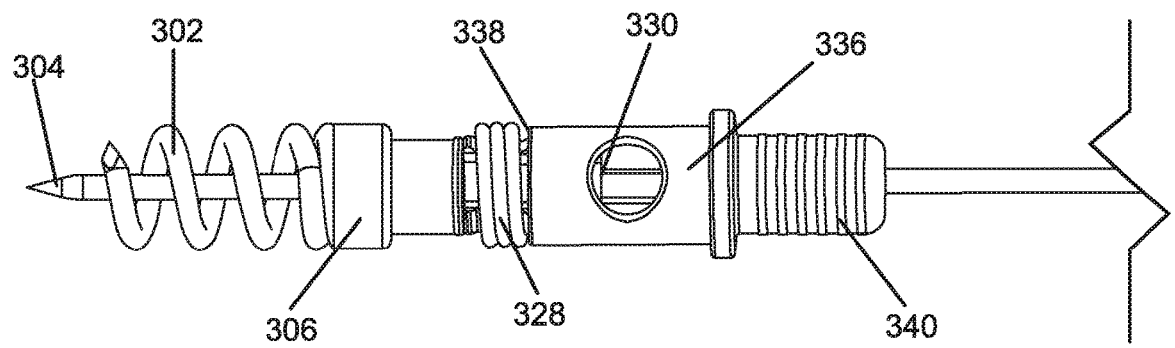

As noted above, anchor hub 306 includes internal threading in a distal portion of anchor hub to releasably secure needle 304 therein. Anchor hub 306 also provides a proximally facing suture clamping surface 318 extending around anchor hub 306. Anchor driver 320 includes a drive end 322 that mates with corresponding internal geometry in the proximal portion of anchor hub 306 to enable rotation of anchor hub 306 with anchor driver 320. Anchor driver 320 can further includes a helical hollow strand (HHS) 324 that extends out of the body and is twisted to provide the torque necessary to drive the anchor coil 302 into the tissue. As can be seen in FIG. 8B, tether 310 extends through anchor driver HHS 324 and anchor driver 320 to a connection within anchor hub 306 to an aperture in the proximal end of stabilizing needle 304. A stiffening tube 326 can be threaded over tether 310 within anchor hub 306 to stiffen a small portion of the tether 310 to provide better alignment to component that need to mate within the anchor hub 306. In embodiments that do not utilize a stabilizing needle 304 as part of the anchor assembly, the tether 310 can attach to the anchor hub 306.

Suture lock assembly 303 includes a suture lock configured as a spring 328 that locks the suture by compressing the suture against the suture capture surface 318 of the anchor hub 306. Suture lock spring 328 can be delivered to the anchor on a spring carrier 330. Spring carrier 330 can include a pair of upwardly raised ledges 348 defining a suture channel 344 therebetween. Each ledge 348 can include a lock depression 350 in which suture lock spring 328 is seated for delivery and a retention lip 352 projecting upwardly from lock depression 350 to prevent inadvertent dislodgement of suture lock spring 328. Spring carrier 330 includes a distal portion that mates with the anchor hub 306 to provide a tensioning point that is near the final point of suture lock to ensure proper tension is maintained. Tubing 334 extends from spring carrier 330 back out of the body to provide a hollow pathway for the tether 310 to enable advancement of the spring carrier 330 guided to the anchor hub 306. In embodiments, tubing 334 can be comprised of PEEK and can be bonded to the spring carrier. A pusher 336 can be advanced over tubing 334 and spring carrier 330 and includes a distal surface 338 configured to engage the suture spring lock 328 to push the suture lock 328 over the retention lips 352 and off of the spring carrier 330, onto the anchor hub 306 and against the suture clamping surface 318 of the anchor hub 306. A pusher connector 340 can be employed to connect the pusher to a catheter 342 used to move the suture lock assembly 303.

Figure 8G:
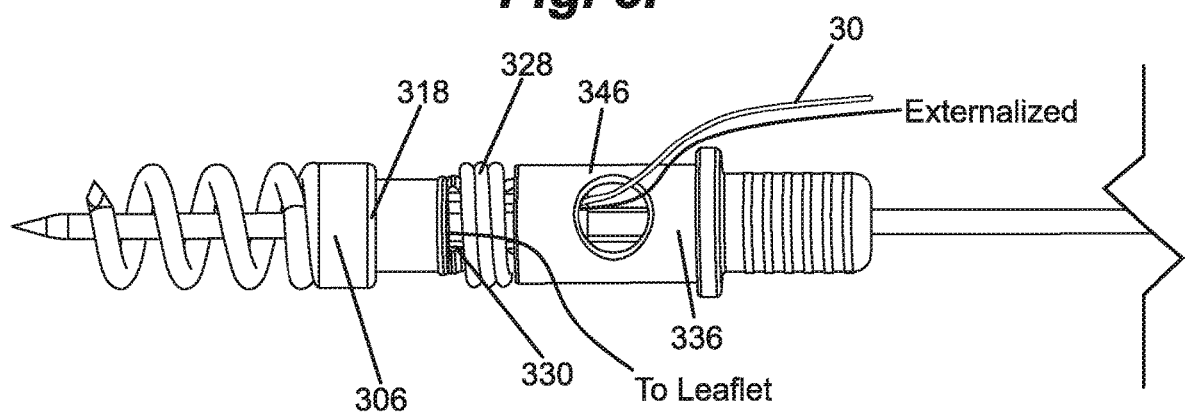
Figure 8H:
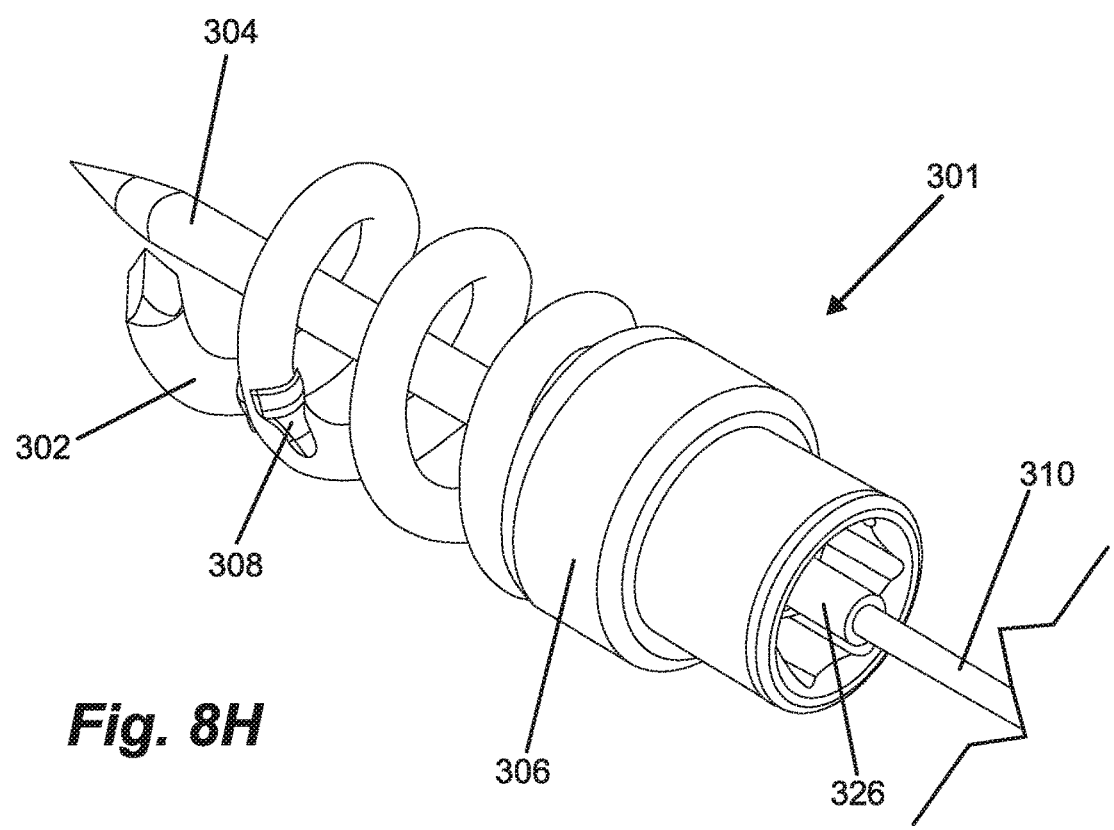
Figure 8I:
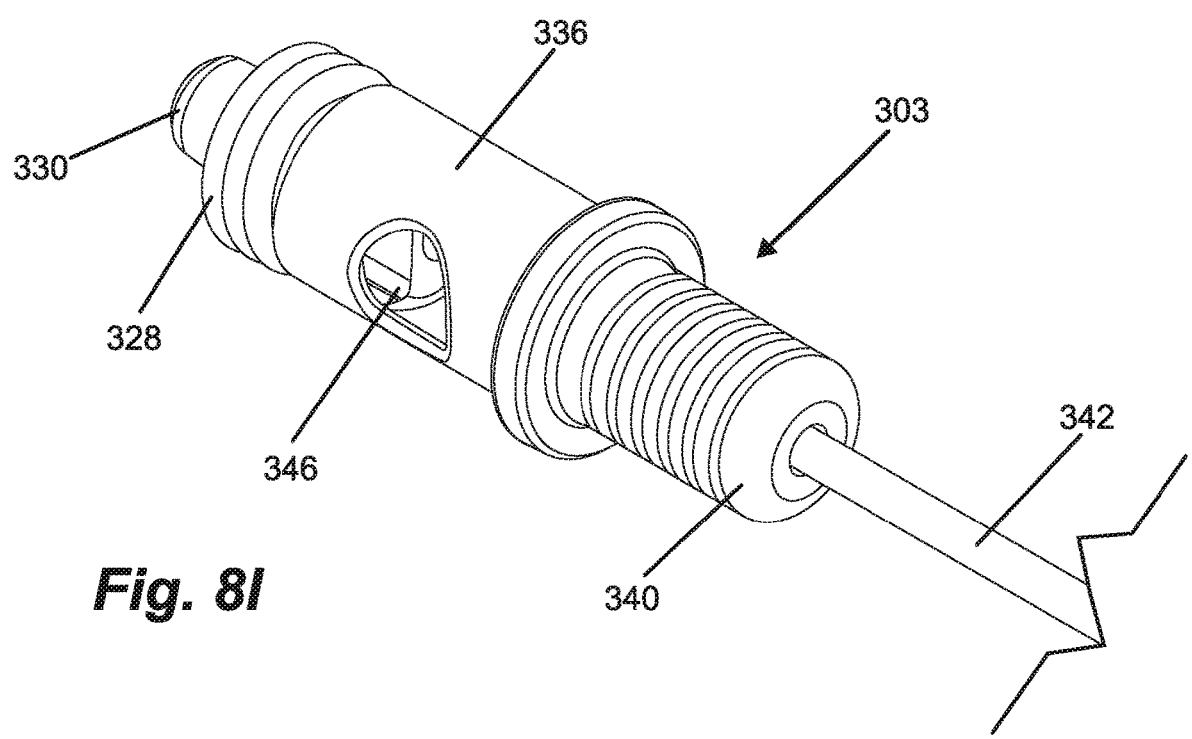

The routing of a suture 30 through suture lock assembly 303 can be seen with respect to FIG. 8G. Outside of the body the suture 30 extending from the leaflet is threaded through the suture channel 344 of the spring carrier 330 beneath the suture lock spring 328, into the pusher 336 and out a suture aperture 346 in the pusher. The suture 30 can then extend back through the anchor catheter out of the body for suture tensioning. When the suture lock spring 328 is deployed with the pusher 336, the suture 30 is crimped under tension between the suture lock spring 328 and the suture capture surface 318 of the anchor base 306.

Figure 10C:
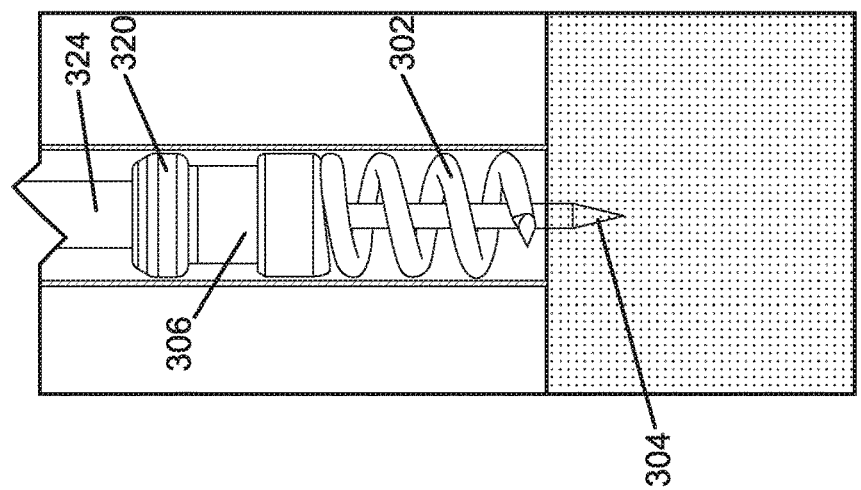
Figure 10B:
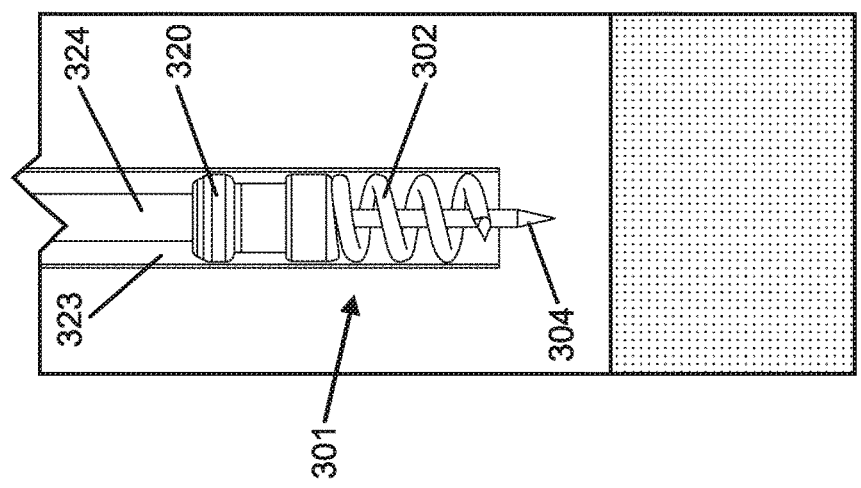
Figure 10A:
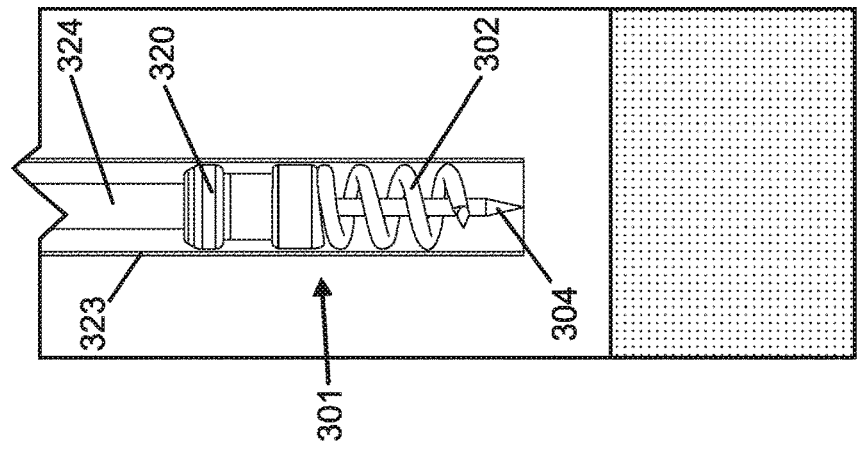
Figure 10F:
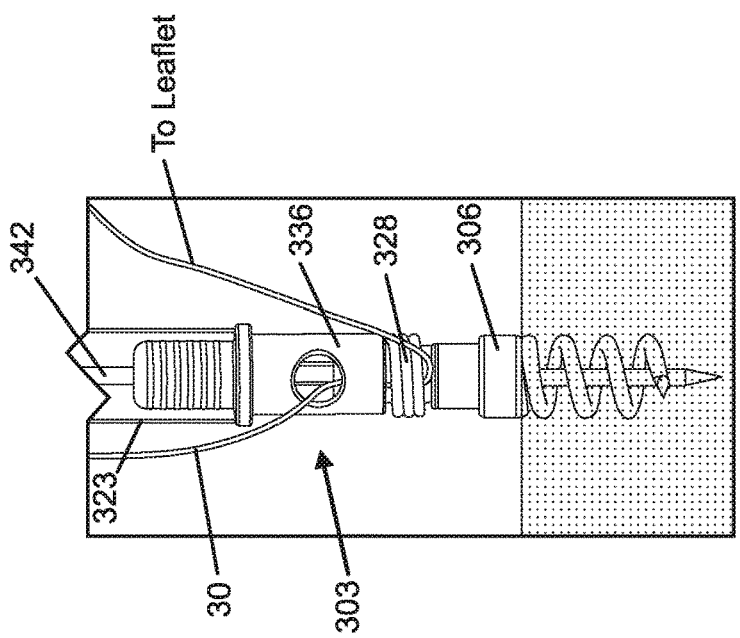
Figure 10E:
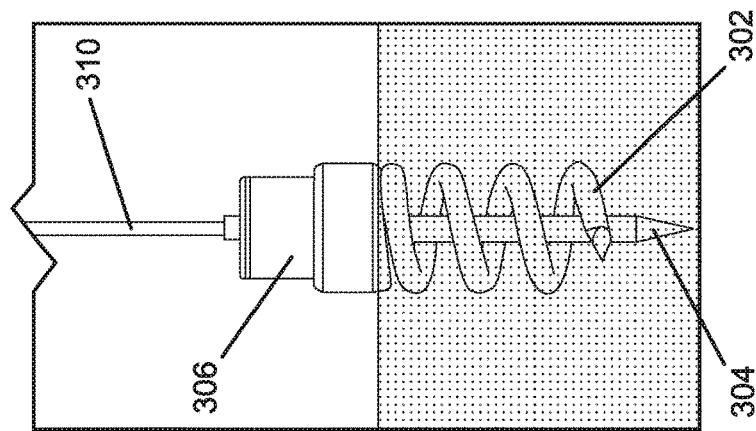
Figure 10D:
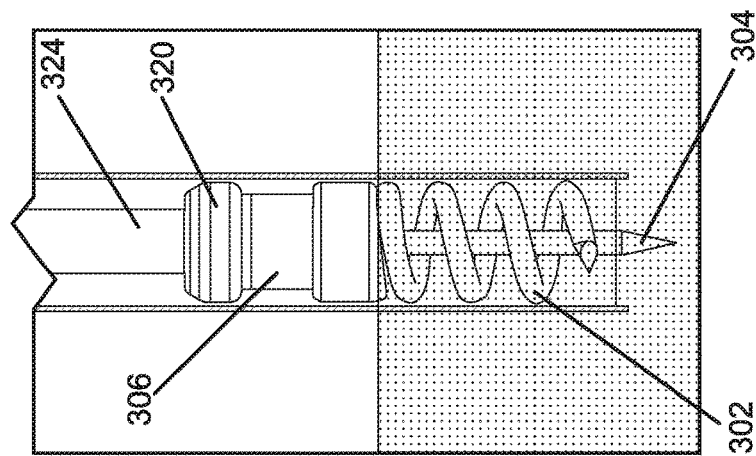

FIGS. 10A-10J depict schematic representations of various steps of a method of repairing a heart valve with an anchor system including anchor delivery assembly 301 and suture locking assembly 303. An anchor delivery catheter 323 delivers the anchor delivery assembly 301 into the heart and the anchor is partially rotated out of the catheter 323 by twisting anchor driver HHS 324 to rotate anchor driver 320 to expose the stabilizing needle 304 to enable insertion of the needle 304 into the heart wall without exposing the anchor coil 302. The anchor hub 306 is then further rotated to insert the anchor coil 302 into the heart tissue and the anchor catheter 323 and anchor driver 320 withdrawn as depicted in FIGS. 10D-10E, leaving a tether 310 in place extending from an anchor hub 306 back out of the heart. Suture lock delivery system 303 is then loaded into anchor catheter 323 and threaded over tether 310 to bring one or more sutures to the anchor as depicted in FIGS. 10F-10J. The suture locking assembly 303 is then primarily withdrawn, leaving the spring carrier 330 that holds a locking spring 328 attached to anchor hub 806 as depicted in FIG. 10G. The sutures 30 can then be appropriately tensioned and then the suture lock delivery system 303 brought back to the anchor as depicted in FIG. 10H with pusher 336 deploying the locking spring 328 off of the spring carrier 330 and onto the anchor hub 306 to clamp the sutures 30 between the locking spring 328 and the anchor hub 306 at the adjusted tension. The suture lock delivery system 303 can then be removed, followed by removal of the tether 310 and attached stabilizing needle 804 and the sutures 30 cut to complete the procedure.

Figure 11A:
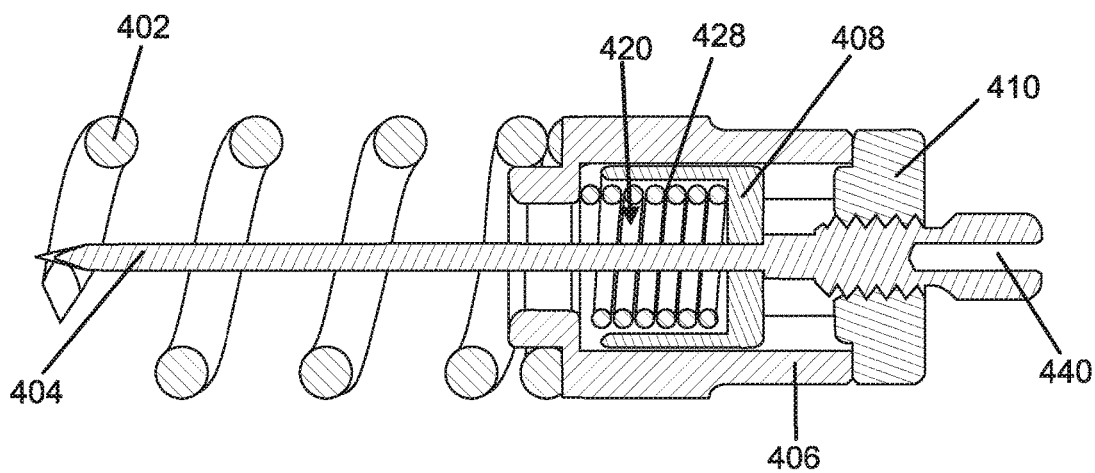
FIGS. 11A-11C depict various views of an anchor system for an artificial chordae according to an embodiment.
Figure 11B:
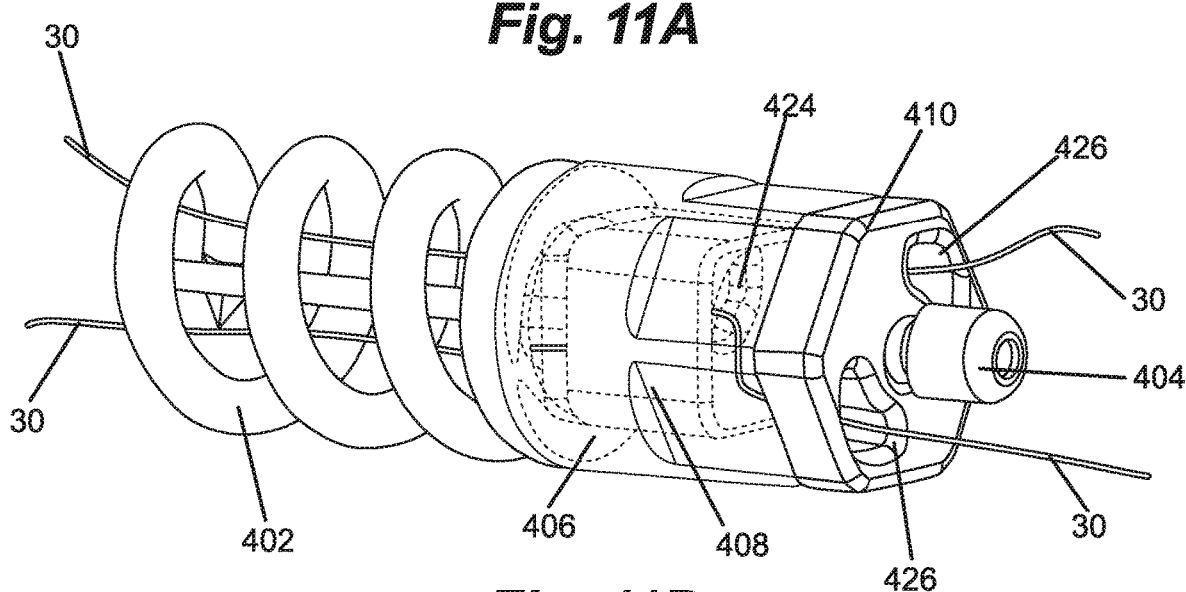
Figure 11C:
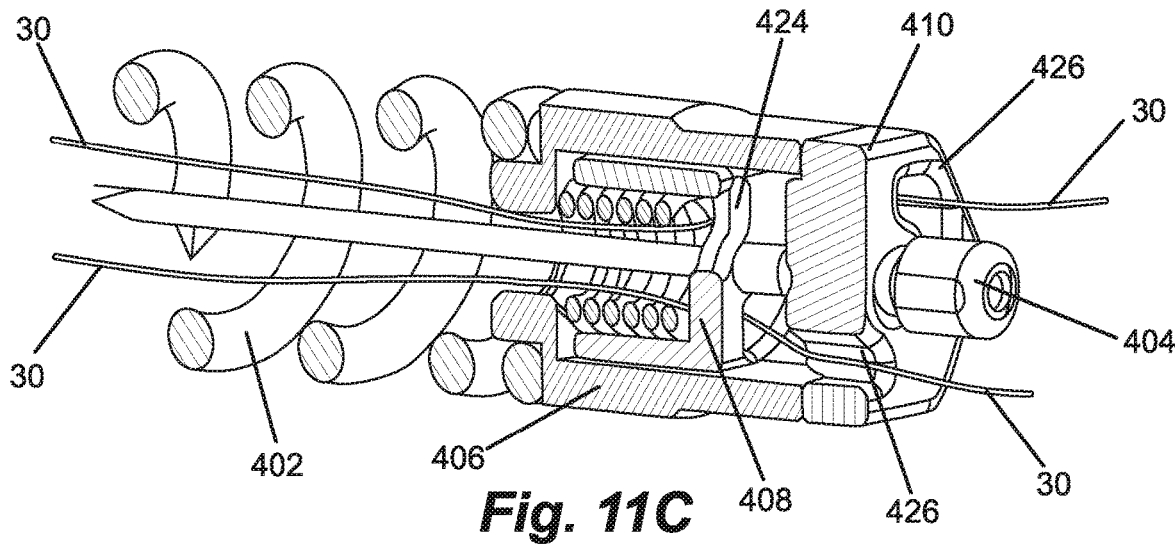

FIGS. 11A-11C depict various views of an anchor assembly for anchoring a suture as an artificial chordae in a heart wall of a patient and FIGS. 12A-12F depict the various components thereof. As with the previous embodiment, anchor assembly includes an anchor coil 402 and, in some embodiments, a stabilizing needle 404 as well as a suture lock configured as a locking spring 428 for locking the sutures at an adjusted tension.

Anchor coil 402 includes a sharpened distal tip 412 for penetrating tissue and, in some embodiments, can be include anti-backout features as described herein. Anchor coil 402 can be attached to anchor hub 406, such as, for example, by laser welding. The proximal portion of anchor hub 406 can comprise a drive end 414 having, e.g., a hex geometry for mating with an anchor driver such as those disclosed above. A suture aperture 416 can be disposed in a distal end of anchor hub 406 to enable a suture to pass from coil 402 through anchor hub 406. Anchor hub 406 can further define an internal piston opening 418 matching an outer diameter of a piston chamber 408 and that enables the piston chamber to slide distally and proximally within the piston opening 418. Suture locking spring 428 can be disposed between the distal end of anchor hub 406 and a proximal end of piston chamber 408 to bias the piston chamber 408 proximally. The piston chamber 408 includes a distally facing spring opening 420 (see FIG. 11A) that constrains the spring 428 and enables the spring 428 expand and contract as piston chamber 408 moves proximally and distally. Piston chamber 408 can further include a central needle opening 422 and a pair of suture openings 424 that enable passage of the needle 404 and one or more sutures therethrough, respectively.

An end cap 410 can be connected to anchor hub 406 such as, for example, by welding after the piston chamber 408 and spring 428 are loaded into the anchor hub 406. The outer geometry 410 of the end cap can include a matching, e.g., hex geometry to the anchor hub 406. End cap 410 can also include a pair of suture openings 426 to enable ends of a suture to pass through the end cap 410. A needle opening 430 through end cap 410 can be threaded to receive a threaded portion 432 of the needle 404. Needle shaft 434 and needle shoulder 436 can be inserted through the needle opening 430 of end cap 410 to enable threaded portion 432 of needle 404 to be screwed into needle opening 430. A tether (not pictured) such as those described herein can be secured within tether aperture 440 in needle cap 438 and twisted to provide the torque necessary to turn the needle 404, with needle cap 438 further preventing the needle 404 from being screwed distally through needle opening 430 of end cap 410. Needle shaft 434 can fit through needle opening 422 in piston chamber 408, but needle shoulder 436 cannot, such that needle shoulder 436 abuts piston chamber 408, such that distal movement of needle 404 presses down on piston chamber 408 to move the chamber distally and compresses the spring 428. Conversely, proximal movement of needle 404 releases the pressure on the piston chamber 408 enabling the spring 428 to move the chamber 408 proximally within the anchor hub 406. In other embodiments, anchor assembly can be provided without stabilizing needle 404. In some such embodiments, a stabilizing needle can alternatively be provided with an anchor delivery catheter, as described below with respect to FIGS. 15A-15H. In such embodiments, the tether can be connected to components similar to the needle cap 438, threaded portion 432, and needle shoulder 436 (without the needle shaft 434) to control movement of the end cap 410.

FIGS. 11B-11C depict the manner in which a suture 30 is routed through anchor assembly. Following insertion of the suture into the leaflet, the suture is threaded through the anchor assembly outside of the body by passing the suture ends through the coil 402 and suture aperture 416 of the anchor hub 406 and then separately through the suture openings 424 of the piston chamber 408 and the suture openings 426 of the end cap 410 such that the suture ends extend back through the anchor catheter out of the body to enabling suture tensioning. As the needle 404 is moved distally, the needle shoulder 436 pushing on the piston chamber 408 to compress the spring 428 causes the suture 30 to be able to slide freely for tensioning. When proper tension is achieved, the needle can be moved back proximally to release the pressure on the spring 428 and move the piston chamber 408 upward to lock the suture by crimping the suture between the piston chamber 408 and the end cap 410. Note that the suture openings 424 is the piston chamber 408 are not longitudinally aligned with the suture openings 426 in the end cap 410, which enables the suture to be crimped between the piston chamber 408 and the end cap 410 when the two components are abutting one another under the force of the spring.

Figure 14C:
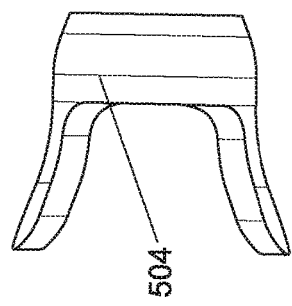
FIGS. 14A-14V depict the various components of the anchor system of FIGS. 13A-13B.
Figure 14F:
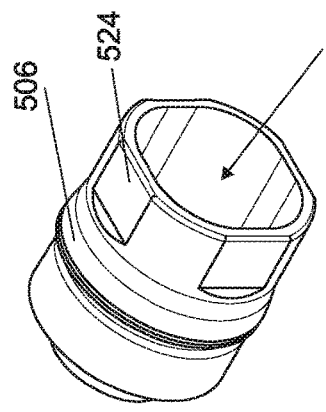
Figure 14H:
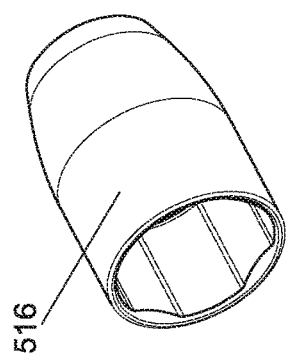
Figure 14B:
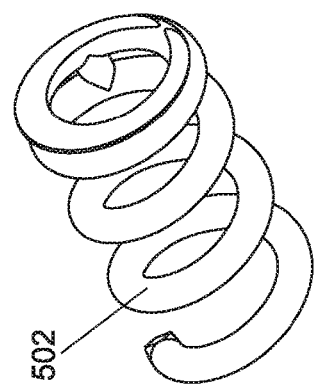
Figure 14E:
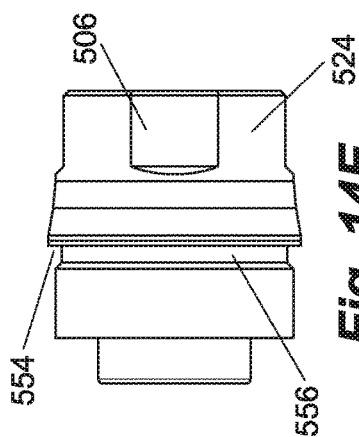
Figure 14G:
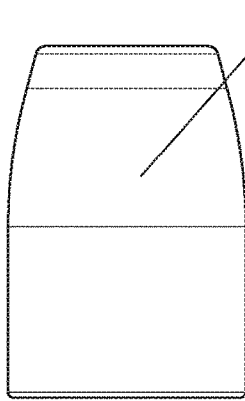
Figure 14A:
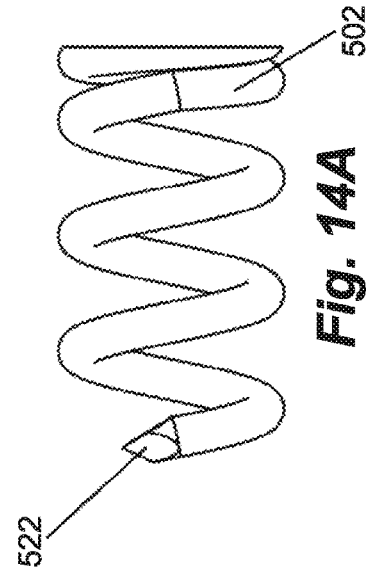
Figure 14D:
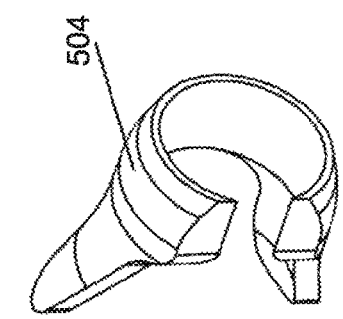

FIGS. 13A-13B depict various views of an anchor assembly 500 for anchoring a suture as an artificial chordae in a heart wall of a patient and FIGS. 14A-14V depict the various components thereof. Anchor assembly 500 includes an anchor coil 502 that embeds the anchor assembly 500 into heart tissue. Anchor coil 502 includes a sharpened distal tip 522 to enable the coil to penetrate the tissue. Anchor coil 502 can also include an anti-backout feature such as a barb 504 that prevents the motion of the heart from twisting the anchor coil 502 out of the tissue. In embodiments, barb 504 can be welded onto the coil 502.

Anchor assembly 500 can also include an anchor hub 506 that can be connected to anchor coil 502, such as, for example, by welding. Anchor hub 506 includes a drive end 524 having a shape, e.g., hexagonal, to mate with an anchor driver 516. Anchor hub 506 can also include a hollow hub chamber 526 within which a suture locking spring 528 and suture clamp plate 510 are contained. An end cap 514 can attach to the proximal end of the anchor hub 506 and can include internal threading 534 that can rotatably receive a threaded tether crimp 512 having a hollow interior portion configured to receive a tether 530 that can be torqued to rotate the tether crimp 512. End cap 514 can further include a proximal drive end 535 configured to mate with the anchor driver 516.

The suture clamp plate 510 can include a pair of suture windows 536 that enable the pair of free ends of the suture 30 to pass through the suture clamp plate 510 (one suture end through each window). The distal surface of the suture clamp plate 510 interfaces with the proximal end of the suture locking spring 528 and the proximal surface of the suture clamp plate (between the suture windows 536) interfaces with a drive end 538 of the tether crimp 512. The end cap 514 can also include a pair of suture windows 540. In embodiments, the suture windows 536 of the suture clamp plate can be offset about 90 degrees from the suture windows 540 of end cap 514. The anchor driver 516 can have an internal geometry matching that of the anchor hub 506 drive end 524 and/or the end cap 514 drive end 535 such that rotation of the anchor driver 516 with driver hypotube 518 extending back to the control handle outside of the body rotates anchor assembly. In embodiments, driver hypotube 518 can be cut, e.g., by laser cutting, with a special pattern 542 at a plurality of locations along its length to make the driver hypotube 518 torqueable yet flexible.

It should be noted that although FIGS. 13A-13B appear to show only a single strand of suture 30, typically a pair of free ends of a suture 30 extending from a leaflet will extend through anchor assembly 500. Referring primarily to FIG. 13B, in operation the free ends of the suture 30 are threaded through the anchor coil 502, into the anchor hub 506 and through the suture locking spring 528, through the suture windows 536, 540 of the suture clamp plate 510 and the end cap 514 and the through the hollow interior of the driver hypotube 518 out of the body. In the initial configuration, the tether crimp 512 can be in a distally advanced position that drives the suture clamp plate 510 down to compress the suture locking spring 528 to create open space 513 between the suture clamp plate 510 and the end cap 514 to create a low friction path for the suture 30 to move generally freely before and during suture tensioning, as depicted in FIG. 13B. To crimp the suture 30 under tension after anchor deployment and suture tensioning, the tether 530 is rotated with the control handle to unscrew the tether crimp 512 and pull the tether crimp 512 proximally through the threading 534 of the end cap 514. As the tether crimp 512 moves proximally, the force of the tether crimp 512 on the suture clamp plate 510 compressing the suture locking spring 528 is released, which causes the spring 528 to expand to push the suture clamp plate 510 against end cap 514 to compress the suture 30 across a tortuous path defined by the offset suture locking windows 536, 540 of the suture clamp plate 510 and the end cap 514. The suture 30 is then locked in place at a set tension with respect to the leaflet. Thus, in this embodiment the natural force of the spring provides the clamping force rather than providing by a component that requires a rotational torque force to clamp the suture.

After the suture 30 is locked, an anchor cap 532 to can be advanced over the tether 530 along a cap aperture 548 to anchor hub 506. The end cap 514 can include a conical or otherwise tapered proximal end 550 to aid in guiding the anchor cap 532 onto the anchor. Anchor cap 532 can further include an internal retention ring 544 having a plurality of retention projections 546 configured to snap onto anchor hub 506 to hold the anchor cap 532 in place on the anchor hub 532. In embodiments, the retention projections 546 can be flexible to be flexed across a circumferential retention lip 554 on anchor hub 506 at the distal and of a tapered region and snap into a circumferential retention recess 556 to hold the anchor cap 532 on the anchor hub 506 via interference between the retention projections 546 and the retention lip 554.

Figure 15F:
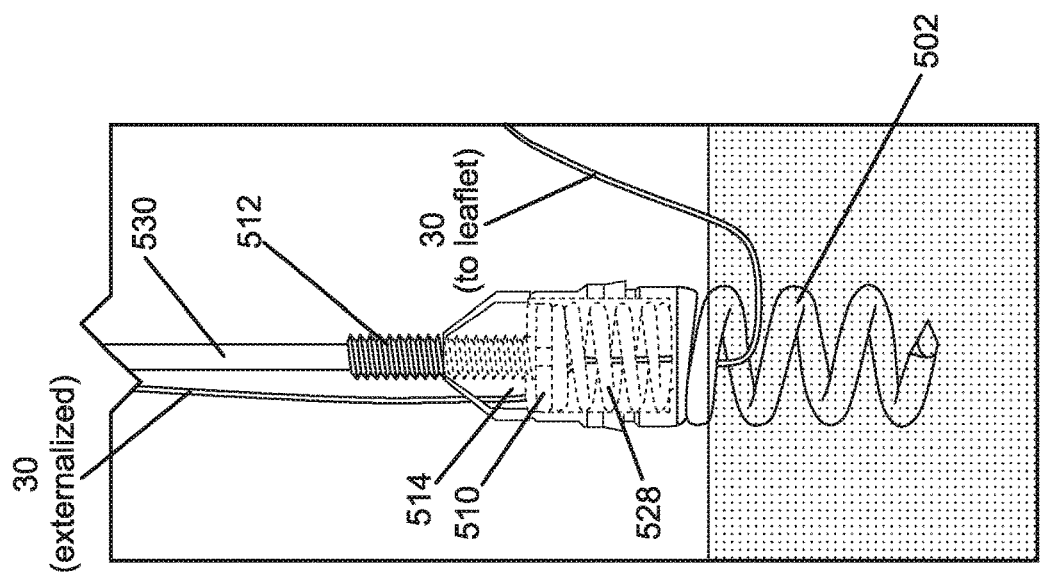

FIGS. 15A-15H depict schematic representations of various steps of a method of repairing a heart valve according to an embodiment that utilizes anchor system 500. After sutures 30 are inserted into a leaflet, the free ends of the suture 30 can be threaded through the anchor assembly 500 as described above exterior to the body such that the suture 30 extend distally out of anchor coil 502 to the leaflet. Anchor catheter 560 can then be used to deliver the anchor system 500 to the heart wall. In this embodiment, the anchor catheter 560 can include a stabilizing needle 564 extendable from a hollow channel 562 or a lumen within anchor catheter. As the anchor catheter 560 is delivered into the heart and near the heart wall, in some embodiments a stabilizing needle 564 can remain within the channel 562 as depicted in FIG. 15A. When the anchor catheter 560 nears the heart wall, the stabilizing needle 564 can be actuated to extend distally of the catheter 560 to penetrate the heart tissue to stabilize the anchor assembly 500 within the anchor catheter 560 when the anchor assembly is subsequently rotated. Although specifically described with respect to the depicted embodiment, such a stabilizing needle provided as part of the anchor catheter could be used with any of the embodiments described herein or a stabilizing needle may not be used with any of those embodiments.

Figure 15E:
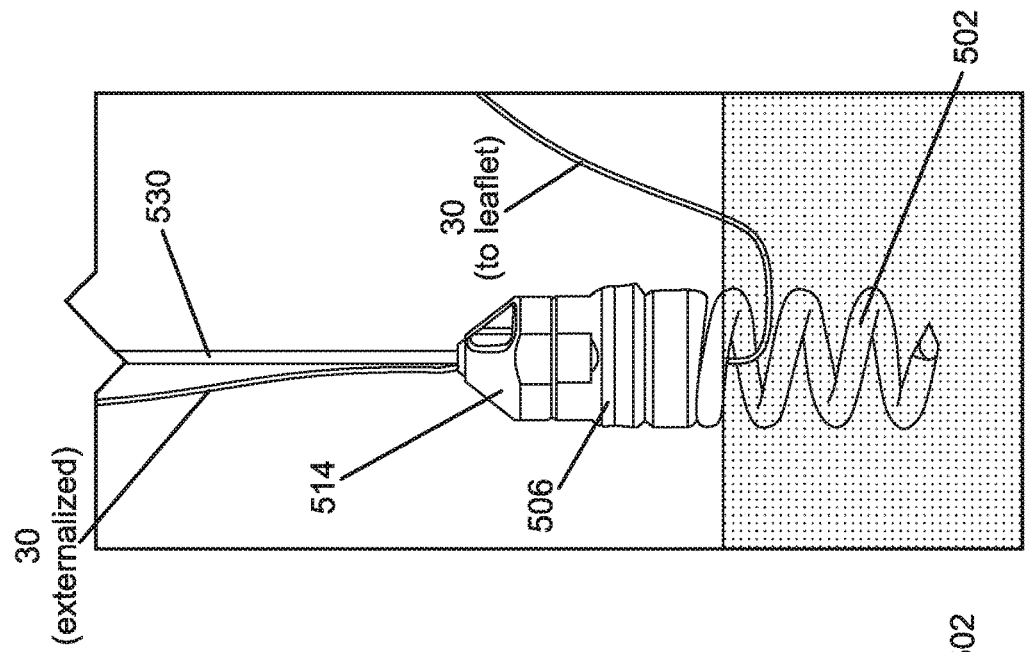
Figure 15D:
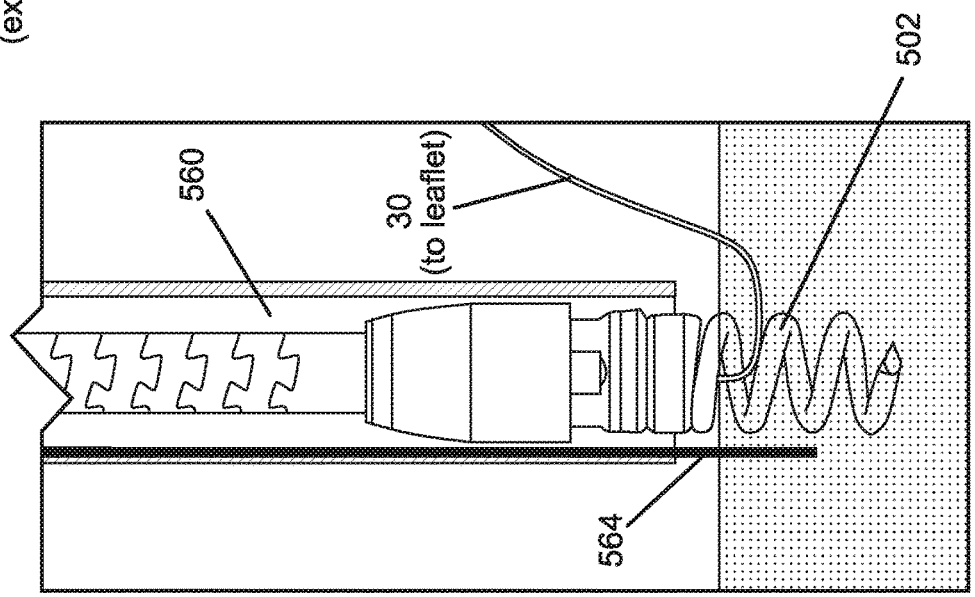

Referring to FIG. 15C, the anchor catheter 560 can be advanced to contact the heart wall with the stabilizing needle 564 embedded in the wall and the anchor coil 502 rotated via the anchor driver 516 and driver hypotube 518 as described above. The anchor catheter 560 and stabilizing needle 564 can then be withdrawn. As depicted in FIG. 15E, the anchor driver 516 can be disengaged from the anchor assembly 500 and the anchor driver 516 and driver hypotube 518 withdrawn. After the suture 30 has been tensioned, the tether 530 is actuated to unscrew the tether crimp 512 which, as described above, releases the distal pressure on the suture locking spring 528 to enable the spring 528 to expand to compress the suture ends 30 between the suture clamp plate 510 and the end cap 514. The anchor cap 532 can then be advanced along the tether 530 to the anchor assembly and interfaced with the anchor hub 506. The tether 530 and tether crimp 512 can then be removed and the excess suture extending up from the anchor assembly and out of the anchor cap 532 can be cut.

Figure 15H:
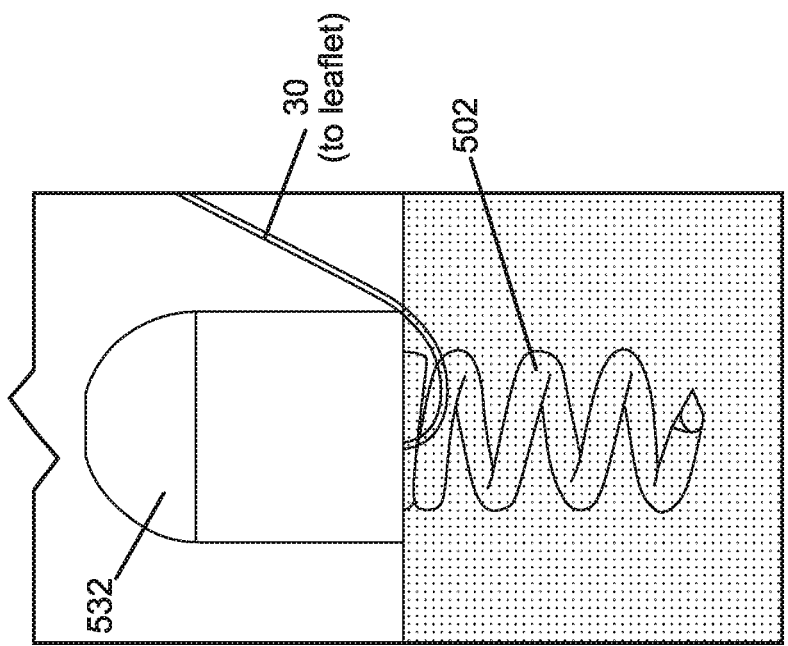
Figure 15G:
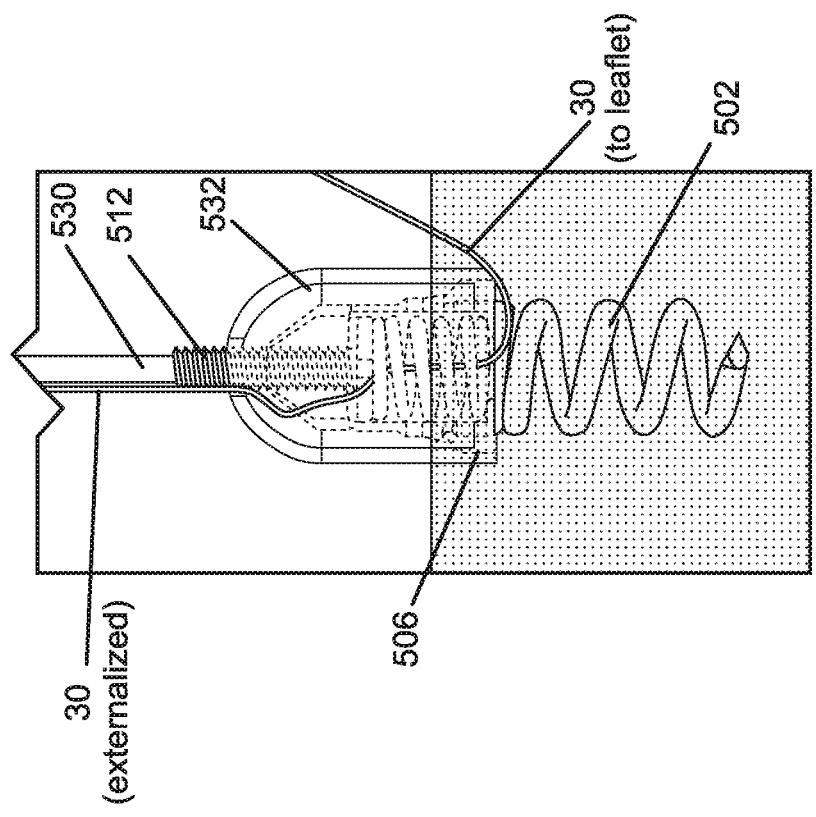

Referring to FIG. 15H, the suture 30 now extends from the anchor assembly 500 to the leaflet as an artificial chordae. Although the suture 30 is clamped within the anchor assembly by the force of the suture locking spring 528 the suture 30 is also captured between the anchor coil 502 and/or anchor hub 506 and the tissue and/or partially embedded within the tissue. As opposed to anchor configurations in which the suture extends out of a more upward portion of the anchor (e.g., out of the top of the end cap 532), this reduces the torque on the anchor from the naturally forces of the leaflet pulling on the suture 30 because the forces act at the very bottom of the anchor at the level of the tissue. This significantly reduces the potential for an anchor failure causing the artificial chordae to fail.

Figure 16E:
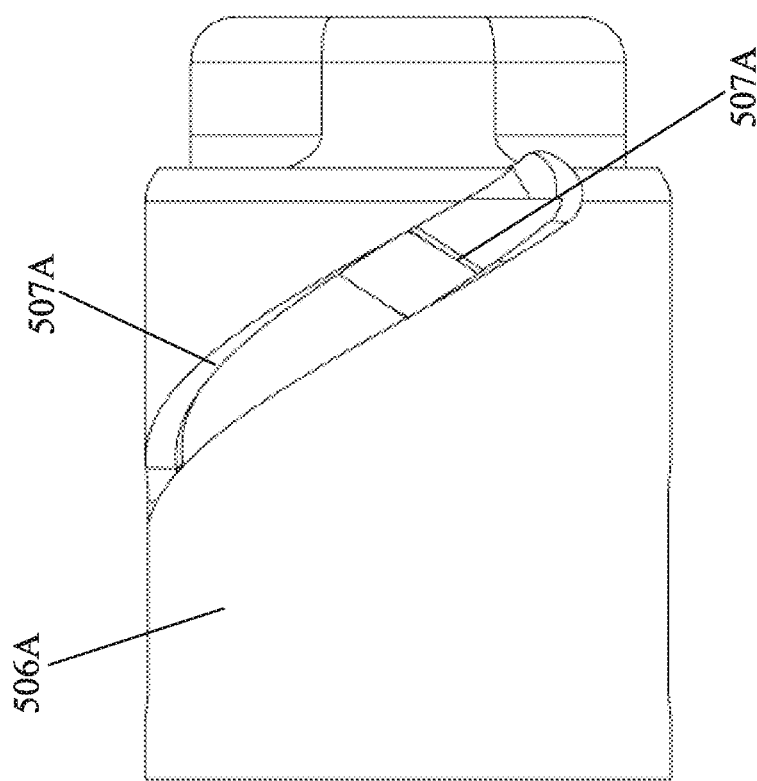

FIGS. 16A-16C depict an anchor assembly 500A that is similar to anchor assembly 500. Anchor assembly 500A also includes an anchor coil 502A with a sharpened distal tip 522A that embeds the anchor assembly 500A into heart tissue and can also include an anti-backout feature such as a barb 504B that prevents the motion of the heart from twisting the anchor coil 502 out of the tissue. Anchor assembly 500A can also include an anchor hub 506A that can contain a suture locking spring 528A and suture clamp plate 510A. In this embodiment, the proximal end of the anchor hub 506A is unitarily formed with the anchor body and an end cap 514A is positioned at a distal end of the anchor hub 506A to retain the suture locking spring 528A and suture clamp plate 510A within the anchor hub 506A. Proximal end of anchor hub 506A can include a proximal drive end 535A configured to mate with an anchor driver. Although not depicted in these figures, anchor assembly 500A would also include a tether crimp such as tether crimp 512 of anchor assembly 500 (as shown, for example, in FIGS. 15F and 15G) extending through threaded opening 534A in anchor hub 506A.

Figure 16D:
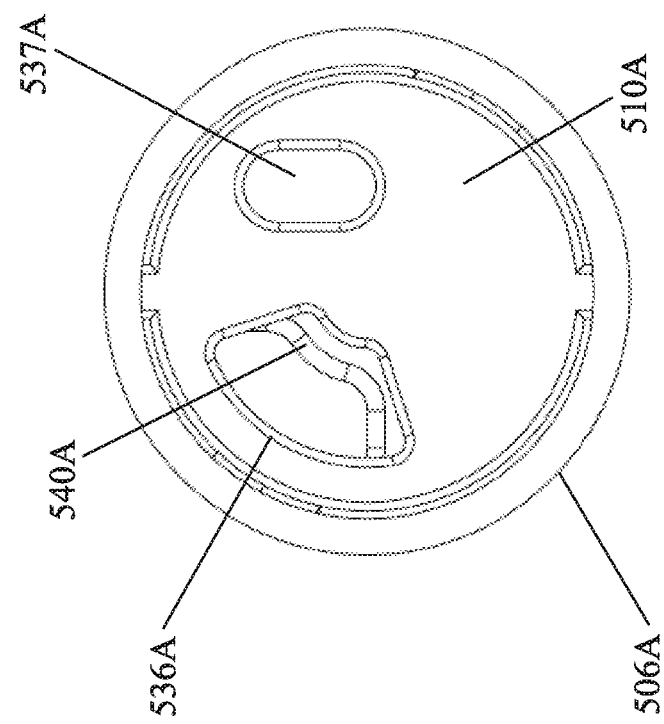

In this embodiment, the anchor hub 506A further includes a helical slot 507A extending around anchor body and the suture clamp plate 510A can include a pair of corresponding outwardly projecting tabs 511A configured to interface with slot 507A. As will be described in more detail below, as the suture clamp plate 510A moves along the helical slot 507A, the suture clamp plate 510A rotates within the anchor hub 506A. Suture clamp plate 510A can further include a suture window 536A and the proximal end of the anchor hub 506A can also include a suture window 540A. Referring to FIG. 16D, when the suture clamp plate 510A is initially inserted into the anchor hub 506A by inserting the tabs 511A into the helical slot 507A, the suture windows 536A, 540A of the two components can be aligned with each other. Suture clamp plate 510A can also include an opening 537A that enables the plate to be held with a forceps for proper positioning within anchor hub 506A as described herein during assembly.

Similar to anchor assembly 500, in operation the free ends of the suture(s) are threaded through the anchor coil 502A of anchor assembly 500A, through the end cap 514A into the anchor hub 506A and through the suture locking spring 528A, through the aligned suture windows 536A, 540A of the suture clamp plate 510A the anchor hub 506A and out of the body. In this initial configuration, the suture clamp plate 510A can be distally positioned with the tether crimp (not pictured) to compress the suture locking spring 528A to create open space between the suture clamp plate 510A and the proximal end of the anchor hub 506A. This creates a generally straight, low friction path through the anchor to enable free movement of the suture for suture length adjustment for tensioning of the suture for proper valve function. The suture can be crimped under tension as described above by unscrewing the tether crimp proximally to release the compression on the suture locking spring 528A to cause the spring 528A to expand to push the suture clamp plate 510A against the proximal end of the anchor hub 506A. As the suture clamp plate 510A moves upward, the projecting tabs 511A in helical slot 507A cause the suture clamp plate 510A to rotate within the anchor hub 506A. This causes the suture window 536A in the suture clamp plate 510A to rotate out of alignment with the suture window 540A in the proximal end of the anchor hub 506A to enable the suture to be crimped between a solid proximally facing surface of the suture clamp plate 510A and a solid distally facing surface of the proximal end of the anchor hub 506A. In various embodiments, the suture window 536A can be rotated approximately, for example, between 50 degrees and 90 degrees offset from the suture window 540A of the anchor hub 506A when in the locked position. After the suture is locked, the anchor assembly 500A can be capped in a similar manner to anchor assembly 500 described above.

Figure 17B:
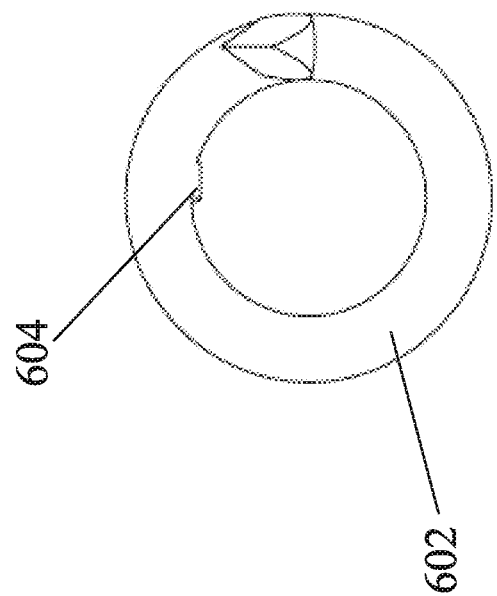
FIGS. 17A-17B depict components of an anchor system for an artificial chordae in an embodiment.
Figure 17A:
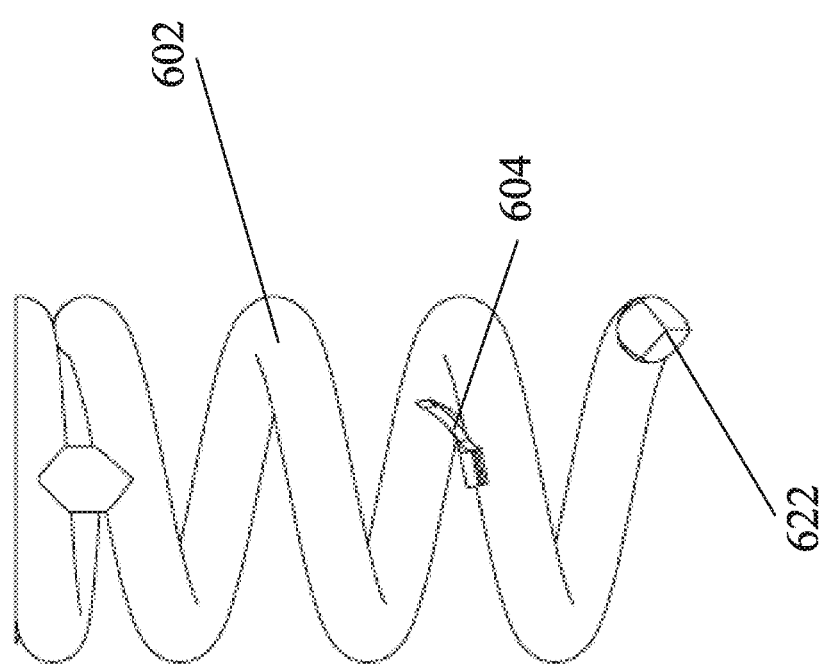

FIGS. 17A-17B depict a coil 602 and a barb 604 for an anchor assembly that can be used with embodiments described herein. In the depicted embodiment, barb 604 is positioned approximately ¾ to 1 revolution of the coil 602 from the tip 622 of the coil. Barb 604 is further sized such that it does not protrude beyond the outer diameter of coil 602 so that it does not interfere with insertion of the coil 602 into the heart tissue. To prevent the coil 602 from backing out of the heart tissue, the barb 604 is positioned at an angle out of the angle of coil 602. In the depicted embodiment, the barb 604 is positioned at an angle of 30 degrees, plus or minus 5 degrees, relative to the coil 602. While a body portion of the barb 604 is welded to the coil to be smooth and free of any burrs or sharp edges, the prong of the barb 604 that extends at an angle from the coil 602 is not welded to the coil.

The anchor assemblies described herein generally each include one or more of an anchor body, anchor hub, anchor cap, dome etc. In embodiments, such components may be comprised of a rigid material such as, for example, stainless steel. In order to limit wear and abrasion on portions of a suture that may repeatedly contact such components due to natural forces of the heart, any such components or combination of components may be provided with a thin cover or jacket over the component or a portion thereof. In embodiments, the cover or jacket can be comprised of a polymer material, such as, for example, ePTFE. In some embodiments, the cover or jacket can have a length greater than the components it is covering such that the polymer or other material extends beyond the components to create a compressible "skirt" to provide additional anchor coverage and/or softening of the tissue interface at the point of contact with the anchor.

It should be noted that in some embodiments, anchor coils are larger in diameter and length and require a greater number of turns that known anchor coils used to anchor other devices such as pacing leads in the heart. This is because unlike pacing leads, anchor coils that serve to anchor sutures as artificial chordae are under immediate and constant forces from the moving valve leaflets that could potentially pull the anchors back out of the heart wall. As such, a more robust fixation provided by a larger and/or longer coil may be desirable to more reliably embed the anchor in the heart wall. In some embodiments, the coil can be inserted generally perpendicularly to the interior surface of the heart wall. In other embodiments, due to the interior geometry of the hard the coil may be inserted at a non-perpendicular angle to the heart wall. In addition, in some embodiments the sharpened distal end of the coil and the sharpened distal end of the stabilizing needle can be oriented generally orthogonal to each other.

Various other anchors can be interchangeably employed in each of the above-described systems. Such anchors can include those disclosed in U.S. Patent Application Publication Nos. 2019/0343626; 2019/0343633; 2019/0343634; and 2020/0330228, which are hereby incorporated by reference.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An anchor assembly configured to be implanted into a heart wall of a heart of a patient to anchor a suture that is configured to extend from a valve leaflet of the heart as an artificial chordae, the anchor assembly comprising:
   an anchor hub defining an open interior and a proximal end covering the open interior;
   a helical coil extending distally from the anchor hub and having a sharpened tip configured to embed the helical coil into the heart wall upon rotation of the helical coil;
   a spring disposed within the open interior of the anchor hub selectively configured to be in one of a compressed state or a released state; and
   a suture clamp plate disposed and movable within the open interior of the anchor hub;
   wherein when the spring is in the compressed state the spring distally creates an open space within the open interior of the anchor hub for the suture to be extended through the anchor hub so as to slide freely within the open interior of the anchor hub, and wherein when the spring is in the released state the spring expands in a proximal direction to clamp the suture across a tortuous path between the suture clamp plate and the anchor hub within the open interior of the anchor hub, and
   wherein the suture clamp plate is configured to rotate within the open interior about a longitudinal axis of the anchor hub relative to the anchor hub as the suture clamp plate moves within the anchor hub.

2. The anchor assembly of claim 1, wherein the anchor hub includes a slot extending around an exterior of the anchor hub and the suture clamp plate includes a pair of projections configured to interface with the slot to cause the suture clamp plate to rotate as the suture clamp plate moves along the slot.

3. The anchor assembly of claim 1, wherein the anchor hub includes a suture window and the suture clamp plate includes a suture window configured to enable the suture to pass therethrough, and wherein when the spring is in the compressed state the suture window of the anchor hub and the suture window of the suture clamp plate are generally aligned with each other and when the spring is in the released state the suture window of the anchor hub is generally offset from the suture window of the suture clamp plate.

4. The anchor assembly of claim 1, further comprising a tether crimp threadedly received through an opening in the anchor hub.

5. The anchor assembly of claim 4, wherein the spring is configured to move from the compressed state to the released state via rotation of the tether crimp.

6. The anchor assembly of claim 4, wherein the suture clamp plate is disposed between the spring and the tether crimp.

7. The anchor assembly of claim 6, wherein in the compressed state, the spring is compressed by the suture clamp plate and the spring is released to the released state by rotation of the tether crimp to move the suture clamp plate to release the spring.

8. An anchor assembly configured to be implanted into a heart wall of a heart of a patient to anchor a suture that is configured to extend from a valve leaflet of the heart as an artificial chordae, the anchor assembly comprising:

an anchor hub defining an open interior and a proximal end covering the open interior;

a helical coil extending distally from the anchor hub and having a sharpened tip configured to embed the helical coil into the heart wall upon rotation of the helical coil;

a suture clamp plate disposed within the open interior of the anchor hub and movable within the anchor hub;

wherein when the suture clamp plate is in a distal state an open space is created within the open interior of the anchor hub for the suture to be extended through the anchor hub so as to slide freely within the open interior of the anchor hub, and wherein when the suture clamp plate is moved to a proximal state the suture clamp plate rotates about a longitudinal axis of the anchor hub to clamp the suture across a tortuous path against the anchor hub.

9. The anchor assembly of claim 8, wherein the anchor hub includes a slot extending around an exterior of the anchor hub and the suture clamp plate includes a pair of projections configured to interface with the slot to cause the suture clamp plate to rotate as the suture clamp plate moves along the slot.

10. The anchor assembly of claim 8, wherein the anchor hub includes a suture window and the suture clamp plate includes a suture window configured to enable the suture to pass therethrough, and wherein when the suture clamp plate is in the distal state the suture window of the anchor hub and the suture window of the suture clamp plate are generally aligned with each other and when the suture clamp plate is in the proximal state the suture window of the anchor hub is generally offset from the suture window of the suture clamp plate.

11. The anchor assembly of claim 8, further comprising a tether crimp threadedly received through an opening in the anchor hub and interfacing with the suture clamp plate.

12. The anchor assembly of claim 11, wherein the suture clamp plate is configured to move from the distal state to the proximal state via rotation of the tether crimp.

13. The anchor assembly of claim 12, further comprising a spring disposed on an opposite side of the suture clamp plate from the tether crimp and wherein rotation of the tether crimp when the suture clamp plate is in the distal state releases pressure on the spring to cause the spring to hold the suture clamp plate in the proximal state.

14. The anchor assembly of claim 12, wherein the tether crimp is configured to be rotated from outside of a body of the patient with a tether extending from the tether crimp, through a vasculature of the patient, and out of the patient.

15. The anchor assembly of claim 8, further comprising a spring disposed within the open interior of the anchor hub selectively configured to be in one of a compressed state or a released state.

16. The anchor assembly of claim 15, wherein when the suture clamp plate is in the distal state the suture clamp plate applies a force that compresses the spring into the compressed state.

17. The anchor assembly of claim 16, wherein when the force is removed from the suture clamp plate, the spring expands to the released state to hold the suture clamp plate in the proximal state.

\* \* \* \* \*